US008318899B2

(12) United States Patent
Leuschner et al.

(10) Patent No.: US 8,318,899 B2
(45) Date of Patent: Nov. 27, 2012

(54) LYTIC DOMAIN FUSION CONSTRUCTS AND METHODS OF MAKING AND USING SAME

(75) Inventors: Carola Leuschner, Baton Rouge, LA (US); Hector Alila, Baton Rouge, LA (US)

(73) Assignees: Board of Supervisors of Louisiana State University and Agricultural and Mechanical College, Baton Rouge, LA (US); Esperance Pharmaceuticals, Baton Rouge, LA (US)

( * ) Notice: Subject to any disclaimer, the term of this patent is extended or adjusted under 35 U.S.C. 154(b) by 264 days.

(21) Appl. No.: 12/359,906

(22) Filed: Jan. 26, 2009

(65) Prior Publication Data

US 2009/0269341 A1 Oct. 29, 2009

Related U.S. Application Data

(60) Provisional application No. 61/023,377, filed on Jan. 24, 2008.

(51) Int. Cl.
*C07K 14/00* (2006.01)
*A61K 38/16* (2006.01)
(52) U.S. Cl. .................. 530/350; 530/300; 424/198.1
(58) Field of Classification Search .................. None
See application file for complete search history.

(56) References Cited

U.S. PATENT DOCUMENTS

| | | | |
|---|---|---|---|
| 5,459,237 A | 10/1995 | Berkowitz et al. | |
| 5,561,107 A | 10/1996 | Jaynes et al. | |
| 5,635,479 A | 6/1997 | Jacob et al. | |
| 5,717,064 A | 2/1998 | Julian et al. | |
| 5,744,445 A | 4/1998 | Jaynes et al. | |
| 5,773,413 A | 6/1998 | Janes et al. | |
| 5,789,542 A * | 8/1998 | McLaughlin et al. | 530/326 |
| 5,792,831 A | 8/1998 | Maloy | |
| 5,861,478 A | 1/1999 | Jaynes | |
| 5,968,904 A | 10/1999 | Julian et al. | |
| 6,001,805 A | 12/1999 | Jaynes et al. | |
| 6,018,102 A | 1/2000 | Garbarino et al. | |
| 6,084,156 A | 7/2000 | Garbabino et al. | |
| 6,191,110 B1 | 2/2001 | Jaynes et al. | |
| 6,255,282 B1 | 7/2001 | Jaynes | |
| 6,303,568 B1 | 10/2001 | Jaynes et al. | |
| 6,348,445 B1 | 2/2002 | Kari et al. | |
| 6,440,935 B1 | 8/2002 | Jaynes et al. | |
| 6,448,391 B1 | 9/2002 | Garbarino et al. | |
| 6,514,692 B2 | 2/2003 | Jaynes | |
| 6,559,281 B1 | 5/2003 | Jaynes | |
| 6,566,334 B1 | 5/2003 | McLaughlin et al. | |
| 6,635,740 B1 | 10/2003 | Enright et al. | |
| 6,656,906 B1 * | 12/2003 | Barney et al. | 530/300 |
| 6,680,058 B1 | 1/2004 | Enright et al. | |
| 6,875,744 B2 | 4/2005 | Owen | |
| 7,091,185 B2 | 8/2006 | Strom et al. | |
| 7,262,163 B2 | 8/2007 | McLaughlin et al. | |
| 7,288,622 B1 | 10/2007 | Jaynes et al. | |
| 7,803,755 B2 | 9/2010 | Jaynes | |
| 2001/0003042 A1 * | 6/2001 | Lorens | 435/6 |
| 2004/0018967 A1 * | 1/2004 | Enright et al. | 514/8 |
| 2005/0187151 A1 | 8/2005 | Strom et al. | |

FOREIGN PATENT DOCUMENTS

| | | |
|---|---|---|
| WO | 91/12015 A1 | 8/1991 |
| WO | 92/22317 A1 | 12/1992 |
| WO | 93/11783 A1 | 6/1993 |
| WO | 93/24138 A1 | 12/1993 |
| WO | 94/12206 A1 | 6/1994 |
| WO | 94/13697 A1 | 6/1994 |
| WO | 94/19369 A1 | 9/1994 |
| WO | 94/25616 | 11/1994 |
| WO | 96/03522 A1 | 2/1996 |
| WO | 98/42364 A1 | 10/1998 |
| WO | 99/03488 A2 | 1/1999 |
| WO | 99/03488 A3 | 1/1999 |
| WO | 00/53755 A2 | 9/2000 |
| WO | 00/53755 A3 | 9/2000 |
| WO | 01/19852 A2 | 3/2001 |
| WO | 01/21194 A2 | 3/2001 |
| WO | 01/68676 A2 | 9/2001 |
| WO | 03/041741 A1 | 5/2003 |
| WO | 03/089455 A2 | 10/2003 |
| WO | 2004/030650 A2 | 4/2004 |
| WO | 2004/087215 A1 | 10/2004 |
| WO | 2004/094462 A2 | 11/2004 |
| WO | 2005/014639 A2 | 2/2005 |
| WO | 2005/023264 A1 | 3/2005 |
| WO | 2005/062881 A2 | 7/2005 |
| WO | 2006/106311 A2 | 10/2006 |
| WO | 2007/115033 A2 | 10/2007 |

OTHER PUBLICATIONS

Leuschner et al, Current Pharm 10:2299-2310, 2004, item VVR, iDS filed on Aug. 21, 2009.*
Boman, H.G., Antibacterial Peptides: Basic Facts and Emerging Concepts, Journal of Internal Medicine, 2003, 254:197-215.
Cavicchioni, G., et al., Biological Variation Responses in fMLP-OMe Analogs, Introducing Bulky Protecting Groups on the Side-Chain of Hydrophilic Residues at Position 2, J.Peptide Res., 2002, 60:223-231.
Dharap, S.S., et al., Tumor-Specific Targeting of an Anticancer Drug Delivery System by LHRH Peptide, PNAS, 2005, 102(36):12962-12967.
Ellerby, H.M., et al., Anti-Cancer Activity of Targeted Pro-Apoptotic Peptides, Nature Medicine, 1999, 5(9):1032-1038.
Javadpour, M.M., et al., De Novo Antimicrobial Peptides with Low Mammalian Cell Toxicity, J. Med. Chem., 1996, 39:3107-3113.
Johnstone, S.A., et al., In vitro Characterization of the Anticancer Activity of Membrane-Active Cationic Peptides. I. Peptide-Mediated Cytotoxicity and Peptide-Enhanced Cytotoxic Activity of Doxorubicin Against Wild-Type and p-Glycoprotein Over-Expressing Tumor Cell Lines, Anti-Cancer Drug Design, 2000, 15:151-160.
Lee, D.L., et al., Effects of Single $_D$-Amino Acid Substitutions on Disruption of β-Sheet Structure and Hydrophobicity in Cyclic 14-Residue Antimicrobial Peptide Analogs Related to Gramicidin S, J. Pept. Res., 2004, 63(2):69-84.

(Continued)

*Primary Examiner* — Lei Yao
(74) *Attorney, Agent, or Firm* — Pillsbury Winthrop Shaw Pittman LLP

(57) ABSTRACT

The invention relates to fusion constructs, methods of using fusion constructs and methods of treating undesirable or aberrant cell proliferation or hyperproliferative disorders, such as tumors, cancers, neoplasia and malignancies.

43 Claims, 22 Drawing Sheets

OTHER PUBLICATIONS

Lyu, P.C., et al., Side Chain Contributions to the Stability of Alpha-Helical Structure in Peptides, Science, 1990, 250:669-673.

Lyu, P.C., et al., α-Helix Stabilization by Natural and Unnatural Amino Acids With Alkyl Side Chains, Proc. Natl. Acad. Sci. USA, 1991, 88:5317-5320.

Mader, J.S., et al., Cationic Antimicrobial Peptides as Novel Cytotoxic Agents for Cancer Treatment, Expert Opin. Investig. Drugs, 2006, 15(8):933-946.

Marks, A.J., et al., Selective Apoptotic Killing of Malignant Hemopoietic Cells by Antibody-Targeted Delivery of an Amphipathic Peptide, Cancer Res., 2005, 65(6):2373-2377.

Min Chen, H., et al., Structure Stability of Lytic Peptides During Their Interactions With Lipid Bilayers, Journal of Biomolecular Structure & Dynamics, 2001, 19(2):193-199.

Min Chen, H., et al., Effects of the Anti-Bacterial Peptide Cecropin B and its Analogs, Cecropins B-1 and B-2, on Liposomes, Bacteria, and Cancer Cells, Biochimica et Biophysica Acta, 1997, 1336:171-179.

O'Neil, K.T., et al., A Thermodynamic Scale for the Helix-Forming Tendencies of the Commonly Occurring Amino Acids, Science, 1990, 250:646-651.

Oren, Z., et al., A Repertoire of Novel Antibacterial Diastereomeric Peptides with Selective Cytolytic Activity, The Journal of Biological Chemistry, 1997, 272(23):14643-14649.

Oren, Z., et al., Structures and Mode of Membrane Interaction of a Short α Helical Lyctic Peptide and its Diastereomer Determined by NMR, FTIR, and Fluorescence Spectroscopy, Eur. J. Biochem., 2002, 269:3869-3880.

Papo, N., et al., A Novel Lytic Peptide Composed of $_{DL}$-Amino Acids Selectively Kills Cancer Cells in Culture and in Mice, The Journal of Biological Chemistry, 2003, 278(23):21018-21023.

Papo, N., et al., Effect of Drastic Sequence Alteration and $_D$-Amino Acid Incorporation on the Membrane Binding Behavior of Lytic Peptides, Biochemistry, 2004, 43:6393-6403.

Rivett, D.E., et al., Dimerization of Truncated Melittin Analogues Results in Cytolytic Peptides, Biochem. J., 1996, 316:525-529.

Shai, Y., From Innate Immunity to de-Novo Designed Antimicrobial Peptides, Current Pharmaceutical Design, 2002, 8:715-725.

Shin, S.Y., et al., Antibacterial, Antitumor and Hemolytic Activities of α-Helical Antibiotic Peptide, P18 and its Analogs, J. Peptide Res., 2001, 58:504-514.

Wade, D., et al., All-$_D$ Amino Acid-Containing Channel-Forming Antibiotic Peptides, Proc. Natl. Acad. Sci. USA, 1990, 87:4761-4765.

Werkmeister, J.A., et al., Sequence Requirements for the Activity of Membrane-Active Peptides, J. Peptide. Res., 2002, 60:232-238.

Bodek, G., et al., A Novel Approach of Targeted Ablation of Mammary Carcinoma Cells Through Luteinizing Hormone Receptors Using Hecate-CGβ Conjugate, Breast Cancer Research and Treatment, 2003, 79:1-10.

Bodek, G., et al., A Novel Targeted Therapy of Leydig and Granulosa Cell Tumors through the Luteinizing Hormone Receptor Using a Hecate-Chorionic Gonadotropin β Conjugate in Transgenic Mice, Neoplasia, 2005, 7(5):497-508.

Bodek, G., et al., Targeted Ablation of Prostate Carcinoma Cells Through LH Receptor Using Hecate-CGβ Conjugate: Functional Characteristic and Molecular Mechanism of Cell Death Pathway, Exp. Biol. Med. 2005, 230:421-428.

Gawronska, B., et al., Effects of Lytic Peptide Conjugated to β hCG on Ovarian Cancer: Studies in Vitro and in Vivo, Gynecologic Oncology, 2002, 85:45-52.

Gawronska, B., et al., Effect of Lytic Peptide Conjugated to β LH on Ovarian Cancer: Studies in Vivo Study, Biology of Reproduction, 2001, 64 (Supp. 1):228, #311.

Hansel, W., et al., Conjugates of Lytic Peptides and LHRH or βCG Target and Cause Necrosis of Prostate Cancers and Metastases, Molecular and Cellular Endocrinology [in press], Mol. Cell. Endocrinol. (2007), doi:10.1016/j.mce.2006.06.017.

Hansel, W., et al., Destruction of Breast Cancers and Their Metastases by Lytic Peptide Conjugates in vitro and in vivo, 2007, Molecular and Cellular Endocrinology, 260-262:183-189.

Hansel, W., et al., Targeted Destruction of Prostate Cancer Cells and Xenografts by Lytic Peptide-βLH Conjugates, Reproductive Biology, 2001, 1(1):20-32.

Isaacs, C.E., et al., A Lipid-Peptide Microbicide Inactivates Herpes Simplex Virus, Antimicrobial Agents and Chemotherapy, 2004, 48(8):3182-3184.

Javadpour, M.M., et al., Self-Assembly of Designed Antimicrobial Peptides in Solution and Micelles, 1997, 36:9540-9549.

Kalia, V., et al., Rational Site-Directed Mutations of the LLP-1 and LLP-2 Lentivirus Lytic Peptide Domains in the Intracytoplasmic Tail of Human Immunodeficiency virus Type 1 gp41 Indicate Common Functions in Cell-Cell Fusion but Distinct Roles in Virion Envelop Incorporation, Journal of Virology, 2003, 77(6):3634-3646.

Leuschner, C., et al., Human Prostate Cancer Cells and Xenografts are Targeted and Destroyed Through Luteinizing Hormone Receptors, The Prostate, 2003, 56:239-249.

Leuschner, C., et al., LHRH-Conjugated Magnetic Iron Oxide Nanoparticles for Detection of Breast Cancer Metastases, Breast Cancer Research and Treatment, 2006, DOI 10.1007/s10549-006-9199-7.

Leuschner, C., et al., Lytic Peptide Conjugated to Gonadotropin Releasing Hormone Kills Prostate Cancer Cells, 2000, Proc. Am. Assoc. Cancer Res., 3:45, #287.

Leuschner, C., et al., Lytic Peptide Conjugated to Luteinizing Hormone (LH) Kills Prostate Cancer Cells in vivo: Increased Toxicity by Pretreatment with Folicle Stimulating Hormone (FSH) or Estradiol, Proc. Am. Assoc. Cancer Res. (Supplement), 2000, 6:4500s, #172.

Leuschner, C., et al., Lytic Peptide Conjugates Destroy Hormone-Dependent and Independent Breast Cancer Cells, Proc. Am. Assoc. Cancer Res. (Supplement), 2001, 7:3752s, #489.

Leuschner, C., et al., Lytic Peptide-CG Conjugate Destroys Breast Cancer Metastases, Proc. Am. Assoc. Cancer Res., 2003, 44:1352, #LB-138.

Leuschner, C., et al., Membrane Disrupting Lytic Peptide Conjugates Destroy Hormone Dependent and Independent Breast Cancer Cells in vitro and in vivo, Breast Cancer Research and Treatment, 2003, 78:17-27.

Leuschner, C., et al., Membrane Disrupting Lytic Peptides for Cancer Treatments, Current Pharmaceutical Design, 2004, 10:2299-2310.

Leuschner, C., et al., Targeted Destruction of Androgen-Sensitive and—Insensitive Prostate Cancer Cells and Xenografts Through Luteinizing Hormone Receptors, The Prostate, 2006, 46:116-125.

Leuschner, C., et al., Targeting Breast and Prostate Cancers Through Their Hormone Receptors, Biology of Reproduction, 2005, 73:860-865.

Leuschner, C., et al., Targeting Breast Cancer and Metastases with a Combination of LHRH and Lytic Peptide, Hecate, Bound to Iron Oxide Nanoparticles, Clin. Cancer Res., 2005, 11(24 Suppl.):9097s, #B262.

Ma, J., et al., Inhibitory Activity of Synthetic Peptide Antibodies on Feline Immunodeficiency Virus Infectivity In Vitro, Journal of Virology, 2002, 76(19):9952-9961.

McLaughlin, M.L., et al., Structure-function Studies of De Novo Lytic Peptides, Peptides: Chemistry, Structure and Biology, Pravin T.P. Kaumaya and Robert S. Hodges (Eds.), Mayflower Scientific Ltd., 1996, pp. 569-570.

Melrose, P.A., et al., Selectivity and Synergy of Lytic Peptide Conjugated Mammalian (M) and Lamprey III (L) Gonadotropin-Releasing Hormone (GnRH) on Primary Prostatic Cancer, Pituitary, and GnRH Neuronal Cell Lines, Proc. Am. Assoc. Cancer Res., 2001, 42:778, #4174.

Robertson, C.N., et al., Peptidyl Membrane-Interactive Molecules are Cytotoxic to Prostatic Cancer Cells in vitro, World J. Urol., 1998, 16:405-409.

Yokum, T.S., et al., Antimicrobial Peptides with Activity Against an Intracellular Pathogen, Peptides, Frontiers of Peptide Science, Proceeding of the Fifteenth American Peptide Symposium, Jun. 14-19, 1997, Nashville, Tennessee, U.S.A., pp. 652-653.

Yokum, T.S., et al., Lytic Peptide-Calixarene Conjugates, Abstracts of Papers, Part 2, 211th ACS National Meeting 0-8412-3397-7, American Chemical Soc., New Orleans, LA, Mar. 24-28, 1996, #262.

Yokum, T.S., et al., Peptides With Indirect in vivo Activity Against an Intracellular Pathogen: Selective Lysis of Infected Macrophages, J. Peptide Res., 2002, 59:9-17.

Zaleska, M., et al., Growth Repression in Diethylstilbestrol/Dimethylbenz[a]anthracene-Induced Rat Mammary Gland Tumor Using Hecate-CGβ Conjugate, Exp. Biol. Med., 2004, 229:335-344.

Zaleska, M., et al., Targeted Destruction of Normal and Cancer Cells Through Lutropin/Choriogonadotropin Receptors Using Hecate-βCG Congugate, Exp. Clin. Endocrinol Diabetes, 2003, 111:146-153.

* cited by examiner

Timeline in vivo to test efficacy of Phor21-βCG-ala, Phor18-βCG-ala, Phor21, Phor18 and ML-βCG-ala inactive peptide

FIG. 8
I) Tumor Volume During Efficacy Study
FIG. 8A
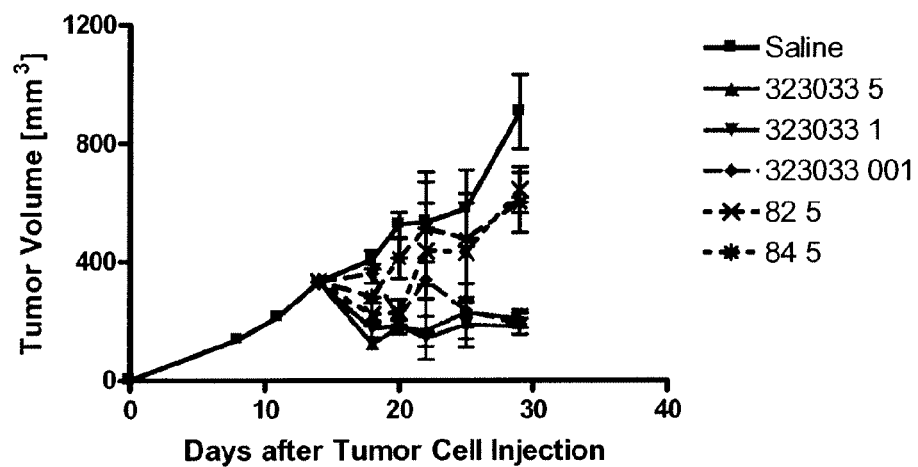
FIG. 8B
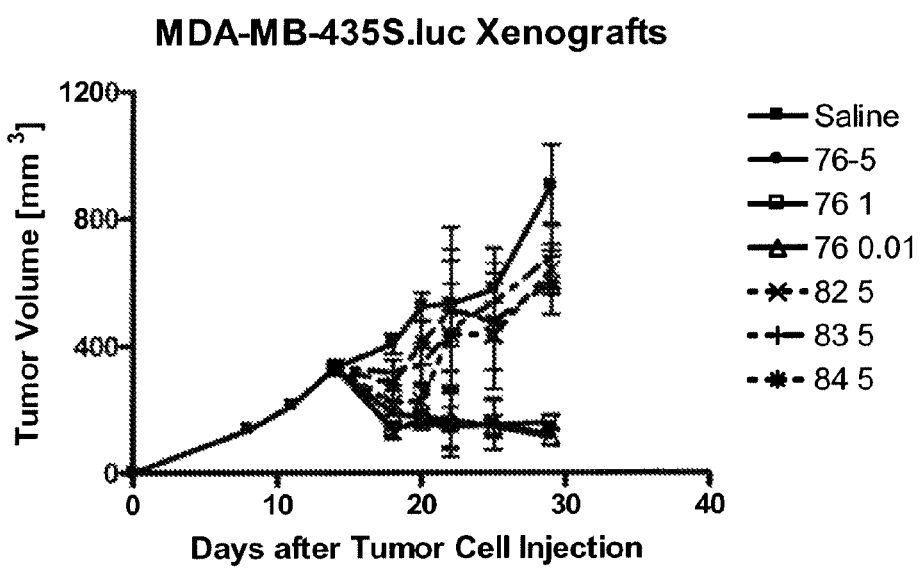

II) Tumor Volume, Weight, Tumor cell Numbers, Tumor Conditions and Body weights at Necropsy.

323033 Phor21-β-CG-ala
337476 Phor18-βCG-ala
337481 D-ala-Phor21-βCG-ala
338982 Phor21
338983 Phor18
338984 (KKKFAFA)$_3$-βCG-ala

Tumor Volume Efficacy Study E 4

Day 30 T vol p < 0.01 compared to baseline

Efficacy Study - LHRH-conjugated Cytolytic Peptides

*p<0.05 compared to 33 0.02 mg/kg

*p<0.04 compared to 33 2 mg/kg

323033 = Phor21-βCG-ala
338611 = D-ala-Phor21-LHRH
338612 = Phor18-ASAAS-LHRH
338613 = Phor18 LHRH
339347 = Phor18 Lupron
339385 = D-ala-Phor18-LHRH IC$_{50}$ Phor21-βCG-ala

- ■ 0 μg/mL Doxorubicin   10.67 μM
- ▲ 0.5 μg/mL Doxorubicin   0.87 μM
- ▼ 2 μg/mL Doxorubicin   0.37 μM
- ◆ 10 μg/mL Doxorubicin   0.05 μM

SEQUENCE LISTING

```
<160> NUMBER OF SEQ ID NOS: 16

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 1

Lys Phe Ala Lys Phe Ala Lys Lys Phe Ala Lys Phe Ala Lys Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 2

Lys Phe Ala Lys Phe Ala Lys Lys Phe Ala Lys Phe Ala Lys Lys Phe
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 3

Lys Phe Ala Lys Phe Ala Lys Lys Phe Ala Lys Phe Ala Lys Lys Phe
1               5                   10                  15

Ala

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 4

Lys Phe Ala Lys Phe Ala Lys Lys Phe Ala Lys Phe Ala Lys Lys Phe
1               5                   10                  15

Ala Lys

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 5

Lys Phe Ala Lys Phe Ala Lys Lys Phe Ala Lys Phe Ala Lys Lys Phe
1               5                   10                  15

Ala Lys Phe
```

```
<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 6

Lys Phe Ala Lys Phe Ala Lys Lys Phe Ala Lys Phe Ala Lys Lys Phe
1               5                   10                  15

Ala Lys Phe Ala
            20

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 7

Lys Phe Ala Lys Phe Ala Lys Lys Phe Ala Lys Phe Ala Lys Lys Phe
1               5                   10                  15

Ala Lys Phe Ala Lys Lys Phe Ala Lys Phe Ala Lys
            20                  25

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Fragment
      of beta-CG Hormone Peptide

<400> SEQUENCE: 8

Ser Tyr Ala Val Ala Leu Ser Ala Gln Ala Ala Leu Ala Arg Arg
1               5                   10                  15

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: LHRH
      Peptide

<400> SEQUENCE: 9

Gln His Trp Ser Tyr Gly Leu Arg Pro Gly
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Linker
      Peptide

<400> SEQUENCE: 10

Gly Ser Gly Gly Ser
1               5

<210> SEQ ID NO 11
<211> LENGTH: 5
<212> TYPE: PRT
```

-continued

```
<213> ORGANISM: Artificial Sequence
<220> FEATURE:
<223> OTHER INFORMATION: Description of Artificial Sequence: Linker
      Peptide

<400> SEQUENCE: 11

Ala Ser Ala Ala Ser
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Fragment
      of beta-CG Hormone Peptide

<400> SEQUENCE: 12

Ser Tyr Ala Val Ala Leu Ser Ala Gln Ala Ala Leu Ala Arg Arg Ala
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Lytic
      Peptide

<400> SEQUENCE: 13

Pro Asn Asn Pro Asn Asn Pro
1               5

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence:
      Phor18-LHRH Peptide

<400> SEQUENCE: 14

Lys Phe Ala Lys Phe Ala Lys Lys Phe Ala Lys Phe Ala Lys Lys Phe
1               5                   10                  15

Ala Lys Gln His Trp Ser Tyr Gly Leu Arg Pro Gly
            20                  25

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence:
      Linker Peptide

<400> SEQUENCE: 15

Lys Lys Lys Phe Ala Phe Ala Lys Lys Lys Phe Ala Phe Ala Lys Lys
1               5                   10                  15

Lys Phe Ala Phe Ala
            20

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:
      LHRH Peptide
```

```
<400> SEQUENCE: 16

Gln His Trp Ser Tyr
1               5
```

LYTIC DOMAIN FUSION CONSTRUCTS AND METHODS OF MAKING AND USING SAME

RELATED APPLICATIONS

This application claims priority to application Ser. No. 61/023,377, filed Jan. 24, 2008, which is expressly incorporated by reference herein in its entirety.

TECHNICAL FIELD

The invention relates to fusion constructs, methods of using fusion constructs and methods of treating undesirable or aberrant cell proliferation or hyperproliferative disorders, such as non-metastatic and metastatic neoplasias, cancers, tumors and malignancies.

INTRODUCTION

The need to develop new therapeutics for treatment of primary tumors and metastases is clearly evident when the five year survival rate of cancer patients is considered: Only 10-40% for patients with lung, colorectal, breast and prostate cancer survive if diagnosed with distant metastatic disease.

SUMMARY

The invention is based, at least in part on lytic domains fused or conjugated to a binding moiety, referred to herein as fusion constructs. Contact of a cell with a lytic domain is believed to cause disruption of the cell membrane which results in cell death. The binding moiety targets cells for destruction by the lytic domain, including undesirable or aberrant proliferating cells or hyperproliferating cells, such as non-metastatic and metastatic neoplasias, cancers, tumors and malignancies. A number of non-metastatic and metastatic neoplastic, cancer, tumor and malignant cells overexpress receptors or ligands. For example, many non-metastatic and metastatic neoplasias, cancers, tumors and malignancies, express receptors for hormones (for example, luteinizing hormone/chorionic gonadotropin (LH/CG), or luteinizing hormone releasing hormone (LHRH etc.), growth factors, cytokines, antibodies etc., that can be used as binding moiety of the fusion construct.

Fusion constructs can be designed to target any cell or cell population that expresses the binding site for the binding moiety. Binding moieties such as ligands, antibodies and fragments thereof, growth factors, cytokines, etc., can be linked to a lytic domain to provide targeted killing of cells that express or contain receptors, antigens, antibodies, ligands etc. thereby reducing or inhibiting cell proliferation or growth.

Fusion constructs do not require cells to divide in order to kill the target cells. Furthermore, the fusion constructs are not likely to be immunogenic because they can be made to be relatively small in size. In addition, the fusion constructs kill multi-drug resistant cells.

Moreover, the fusion constructs can have greater cytotoxic activity (low $IC_{50}$) in terms of anti-cell proliferative activity or killing activity and low hemolytic activity ($HA_{50}$), such that the ratio of $IC_{50}$:$HA_{50}$ ($IC_{50}/HA_{50}$) is lower than other compounds with such activities. For example, fusion constructs can have greater anti-cell proliferative activity than Phor21-βCG-ala, Phor21-GSGGS-βCG-ala, Phor21-ASAAS(SEQ. ID NOs. 10 and 11)-βCG-ala, or Phor 14-βCG-ala, as ascertained by a lower $IC_{50}$ value; have a lower $IC_{50}/HA_{50}$ ratio than Phor21-βCG-ala, Phor21-GSGGS-βCG-ala, Phor21-ASAAS(SEQ. ID NOs. 10 and 11)-βCG-ala, or Phor 14-βCG-ala; or have an $IC_{50}/HA_{50}$ ratio of less than about 0.02, 0.01, or 0.005.

In accordance with the invention, there are provided fusion constructs that include a first and a second domain. In one embodiment, a fusion construct includes or consists of a first domain consisting of a 12, 13, 15, 16, 17, 18, 19, 20, 22, 23, 24, 25, 26, 27 or 28 residue L- or D-amino acid sequence that includes a peptide sequence selected from for example, KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7), and a second domain that includes or consists of a targeting or binding moiety. In another embodiment, a fusion construct includes or consists of a first domain consisting of an L- or D-amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7), and a second domain that includes or consist of a targeting or binding moiety. In a further embodiment, a fusion construct includes or consists of a first domain consisting of an L- or D-amino acid sequence selected from, KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7), and a second domain consisting of a 1-25 L- or D-amino acid sequence (e.g., targeting or binding moiety) distinct from said first domain.

In accordance with the invention, there are also provided isolated and purified peptides that include or consist of a first domain. In various embodiments, an isolated or purified peptide is KFAKFAKKFAKFAKK, KFAKFAKKFAKFAKKF, KFAKFAKKFAKFAKKFA, KFAKFAKKFAKFAKKFAK, KFAKFAKKFAKFAKKFAKF or KFAKFAKKFAKFAKKFAKFA (SEQ. ID NOs. 1 to 6). In additional embodiments, an isolated or purified peptide is KFAKFAKKFAKFAKK, KFAKFAKKFAKFAKKF, KFAKFAKKFAKFAKKFA, KFAKFAKKFAKFAKKFAK, KFAKFAKKFAKFAKKFAKF or KFAKFAKKFAKFAKKFAKFA (SEQ. ID NOs. 1 to 6) having one or more of the K residues substituted with any of an F or L residue, one or more of the F residues substituted with any of a K, A or L residue, or one or more of the A residues substituted with any of a K, F or L residue.

Fusion constructs include a binding moiety that binds to a receptor, ligand, or an antigen. A binding moiety also includes a ligand, antigen or an antibody. Ligands include or consist of a molecule that binds to a receptor, such as a receptor agonist or antagonist. A binding moiety can include or consist of a linear or cyclic structure.

Specific non-limiting examples of binding moieties include one or more amino acids (e.g., peptides, polypeptides, proteins), nucleic acids and carbohydrates. Specific non-limiting classes of binding moieties include hormones, hormone analogues, and fragments of hormones and hormone analogs, growth factors, cytokines, antibodies etc. that bind to a receptor. Specific non-limiting examples of hormones include a gonadotropin-releasing hormone or its analogs, luteinizing hormone beta chain, luteinizing hormone, chorionic gonadotropin, chorionic gonadotropin beta subunit, melanocyte stimulating hormone, estradiol, diethylstilbestrol, lactoferrin, dopamine, somatostatin or its analogs, follicle-stimulating hormone (FSH), glucocorticoid, estrogen, testosterone, adrostenedione, dihydrotestosterone, dehydroepiandrosterone, androgens, progesterone, thyroid stimulating hormone (TSH), insulin, catecholamines, adrenocorticotropic hormone (ACTH), angiotensin, antidiuretic hormone, calcitonin, cholecystokinin, bombesin, corticotrophin-releasing hormone, gastrin, ghrelin, glucagon, Growth Hormone Releasing Hormone and its analogs, inhibin, orexin, KiSS peptide (GPR54), kisspeptin, Prolactin, Prolactin Releasing Hormone, Growth Hormone, Her2/neu, folate, vitamin H, ferritin, Parathyroid Hormone, Relaxin, Secretin, Thyrotropin Releasing Hormone, Endothelin, Renin, Lipotropin, melatonin etc. Specific non-limiting examples of growth factors are epidermal growth factor (EGF), insulin-like growth factor-1 and 2 (IGF-1, IGF-2), vascular endothelial growth factor (VEGF), Nerve Growth Factor (NGF), Fibroblast Growth Factor (FGF), Transforming Growth Factor alpha and beta (TGFα, TGFβ), Platelet Derived Growth Factor (PDGF), Hepatocyte Growth Factor (HGF), ceruloplasmin etc. Specific non-limiting classes of cytokines or ligands are interleukins (for example interleukin 2, interleukin 17, CD154, Fas Ligand etc), Tumor Necrosis Factors (TNFs), interferons, etc.

Binding moieties can be optionally expressed on a cell. Cells that express a binding moiety (e.g., receptor, ligand, antigen, antibody) or that can be targeted in accordance with methods of the invention include hyperproliferative cells. Cells that express a receptor, ligand, or antigen, or that can be targeted in accordance with methods of the invention also include breast, ovarian, uterine, cervical, prostate, testicular, pancreatic, skin, blood cells, adrenal, pituitary and endometrial cells. Specific non-limiting classes of binding moieties expressed on a cell are receptors for hormones, cytokines, growth factors (for example EGF receptors, Her2/neu, ROR1), ferritin, transferrin receptors, cell adhesion molecules, etc. Specific non-limiting examples of antigens expressed on proliferating cells that can be targeted with antibodies or their fragments are CD19, CD20, CD23, CD27, CD28, CD30, CD33, CD40, CD52, CD56, CD70, CD154, immunoglobulin-like receptors etc). Further antigens, include, for example, prostate specific antigen (PSA), prostate specific membrane antigen (PSMA), carcinoembryonic antigen (CEA), alpha-fetoprotein (AFP), prostate specific antigen (PSA), cancer antigen 125 (CA-125) and other receptor molecules that bind to ligands disclosed herein.

First and second domains can include or consist of an amino acid, or an amino acid sequence. In particular aspects, a first or second domain has about 1 to 10, 10 to 20, 15 to 20 (i.e., 15, 16, 17, 18, 19 or 20 amino acids), 20 to 30, 30 to 40, 40 to 50, 60 to 70, 70 to 80, 80 to 90, 90 to 100 or more amino acid residues.

In a particular aspect, a first domain includes or consists of an amphipathic alpha-helical structure. In further particular aspects, a second domain includes or consists of an amino acid sequence set forth as SYAVALSAQAALARR or QHWSYGLRPG (SEQ. ID NOs. 8 to 9).

First and second domains can be positioned at either the NH-terminus or the C-terminus relative to$_{[A1]}$ each other. Thus, in one embodiment the first (lytic peptide) domain is positioned at the NH-terminus relative to the second (binding moiety or ligand) domain, and in another embodiment, the second (binding moiety or ligand) domain is positioned at the C-terminus relative to the first (lytic peptide) domain.

First and second domains can include or consist of one or more D-amino acids. In particular aspects, a first domain has a D-amino acid, for example, at any K, F or A residue.

First and second domains can be joined by a covalent bond. For example, a first and a second domain can be joined by a peptide or a non-peptide linker. In particular aspects, first and second domains are joined by a peptide sequence having from about 1 to 25 amino acid residues, or having a linear carbon chain. In more particular aspects, first and second domains are joined by a peptide sequence that includes or consist of one or more A, S or G amino acid residues. In further particular aspects, first and second domains are joined by a peptide sequence a first and second domain is joined by peptide sequence including or consisting of GSGGS (SEQ. ID NO.10), ASAAS(SEQ. ID NO.11), or CCCCCC.

First and second domains can further include or consist of additional domains. Thus, in various aspects, a fusion construct includes a third, fourth, fifth, sixth, seventh domain, etc.

Fusion constructs include or consist of isolated and purified forms. Fusion constructs also include or consist of a mixture. Such mixtures include compositions, such as a mixture of fusion construct and a pharmaceutically acceptable carrier or excipient appropriate for administration to or in vivo contact with a subject, or a mixture of fusion construct and an anti-cell proliferative or immune stimulating agent.

Fusion constructs include or consist of a unit dosage form. In one embodiment, a fusion construct is a unit dosage in an amount effective to treat a subject having undesirable cell proliferation or a hyperproliferative disorder. In another embodiment, a fusion construct is a unit dosage in an amount effective to treat a subject having a neoplasia, tumor or cancer. In an additional embodiment, a fusion construct is a unit dosage in an amount effective to reduce fertility of a subject.

Fusion constructs can be included within kits, optionally with instructions for practicing a method. In one embodiment, a kit includes a fusion construct and instructions for reducing or inhibiting proliferation of a cell, reducing or inhibiting proliferation of a hyperproliferating cell, reducing or inhibiting proliferation of a neoplastic, tumor or cancer cell, treating a subject having a hyperproliferative disorder, treating a subject having a neoplasia, tumor or cancer, or reducing fertility of an animal.

In accordance with the invention, there are also provided nucleic acids that encodes fusion constructs. In one embodiment, a nucleic acid encodes a fusion construct including or consisting of a first domain consisting of a 12, 13, 15, 16, 17, 18, 19, 20, 22, 23, 24, 25, 26, 27 or 28 residue L- or D-amino acid sequence that includes a peptide sequence selected from KFAKFAKKFAKFAKK, KFAKFAKKFAKFAKKF, KFAK-FAKKFAKFAKKFA, KFAKFAKKFAKFAKKFAK, KFAKFAKKFAKFAKKFAKF, KFAKFAKKFAK-FAKKFAKFA and KFAKFAKKFAKFAKKFAK-FAKKFAKFAK (SEQ. ID NOs. 1 to 7), and a second domain including or consists of a targeting or binding moiety. In another embodiment, a nucleic acid encodes a fusion construct including or consisting of a first domain consisting of an L- or D-amino acid sequence selected from KFAK-FAKKFAKFAKK, KFAKFAKKFAKFAKKF, KFAK-FAKKFAKFAKKFA, KFAKFAKKFAKFAKKFAK, KFAKFAKKFAKFAKKFAKF, KFAKFAKKFAK-FAKKFAKFA and KFAKFAKKFAKFAKKFAK-FAKKFAKFAK (SEQ. ID NOs. 1 to 7), and a second domain that includes or consist of a targeting or binding moiety. In a further embodiment, a nucleic acid encodes a fusion construct including a first domain consisting of an L- or D-amino acid sequence selected from KFAKFAKKFAKFAKK, KFAK-FAKKFAKFAKKF, KFAKFAKKFAKFAKKFA, KFAK-FAKKFAKFAKKFAK, KFAKFAKKFAKFAKKFAKF, KFAKFAKKFAKFAKKFAKFA and KFAKFAKKFAK-FAKKFAKFAKKFAKFAK (SEQ. ID NOs. 1 to 7), and a second domain including or consisting of a 1-25 L- or D-amino acid sequence (e.g., targeting or binding moiety) distinct from said first domain.

Nucleic acids can be included in a vector, such as an expression vector that when expressed in a cell encodes a fusion construct. Host cells can be transformed with a nucleic acid in a vector, such that the cell expresses a fusion construct encoded by the nucleic acid.

Fusion constructs are useful for, among other things, reducing or inhibiting proliferation of a cell, reducing or inhibiting cell proliferation, reducing or inhibiting proliferation of a hyperproliferating cell, reducing or inhibiting proliferation of a neoplastic, tumor, cancer or malignant cell and treating undesirable or aberrant cell proliferation, such as hyperproliferating cells or hyperproliferative disorders. Non-limiting examples of hyperproliferative disorders include benign hyperplasia, non-metastatic and metastatic neoplasias, cancers tumors and malignancies (e.g., a solid or liquid tumor, myeloma, lymphoma, leukemia, carcinoma, sarcoma, melanoma, neural, reticuloendothelial and haematopoietic).

In accordance with the invention, there are further provided methods of reducing or inhibiting proliferation of a cell; methods of reducing or inhibiting cell proliferation; methods of reducing or inhibiting proliferation of a hyperproliferating cell; and methods of reducing or inhibiting proliferation of a neoplastic, tumor, cancer or malignant cell. In various embodiments, a method includes contacting a cell with a fusion construct in an amount sufficient to reduce or inhibit proliferation of the cell; contacting a cell with a fusion construct in an amount sufficient to reduce or inhibit cell proliferation; contacting a cell with a fusion construct in an amount sufficient to reduce or inhibit proliferation of the hyperproliferating cell; and contacting a cell with a fusion construct in an amount sufficient to reduce or inhibit proliferation of the neoplastic, tumor, cancer or malignant cell.

In accordance with the invention, there are moreover provided methods of selectively reducing or inhibiting proliferation of a cell that expresses a receptor or antigen; selectively reducing or inhibiting proliferation of a hyperproliferating cell that expresses a receptor or antigen; and selectively reducing or inhibiting proliferation of a neoplastic, tumor, cancer or malignant cell that expresses a receptor or antigen. In various embodiments, a method includes contacting a cell with the fusion construct in an amount sufficient to reduce or inhibit proliferation of the cell, wherein the binding moiety of said peptide binds to the receptor, ligand, or antigen expressed by the cell; contacting a cell with the fusion construct in an amount sufficient to reduce or inhibit proliferation of the hyperproliferating cell, wherein the binding moiety of said peptide binds to the receptor, ligand, or antigen expressed by the hyperproliferating cell; and contacting a cell with the fusion construct in an amount sufficient to reduce or inhibit proliferation of the neoplastic, tumor, cancer or malignant cell, wherein the binding moiety of said fusion construct binds to the receptor, ligand, or antigen expressed by the cell.

Cells targeted in accordance with the invention methods include cells that express a receptor, or an antigen, such as a hormone receptor, for example, a sex or gonadal steroid hormone or a sex or gonadal steroid hormone receptor. Cells targeted in accordance with the invention methods also include cells that express a receptor that binds to gonadotropin-releasing hormone I, gonadotropin-releasing hormone II, lamprey III luteinizing hormone releasing hormone, luteinizing hormone beta chain, luteinizing hormone, chorionic gonadotropin, chorionic gonadotropin beta subunit, melanocyte stimulating hormone, estradiol, diethylstilbestrol, dopamine, somatostatin, follicle-stimulating hormone (FSH), glucocorticoid, estrogen, testosterone, adrostenedione, dihydrotestosterone, dehydroepiandrosterone, progesterone, androgen, prolactin, prolactin releasing hormone, antidiuretic hormone, angiotensin, catecholaimes, epidermal growth factor (EGF), insulin like growth factor-1 and 2 (IGF-1, IGF-2), growth hormone (GH), Her2/neu, vitamin H, folate, transferrin, thyroid stimulating hormone (TSH), parathyroid hormone (PTH), endothelin, bombesin, Renin, Lipotropin, melatonin hormone, relaxin, secretin, growth hormone, vascular endothelial growth factor (VEGF), vasoactive intestinal peptide, lactoferrin, an integrin (e.g., alpha-5 beta 3 or alpha-5 beta 1 integrin), nerve growth factor, transforming growth factor alpha and beta (TGF-α and β), hepatocyte growth factor (HGF), fibroblast growth factor (FGF), CD-33, CD19, CD20, CD40, ROR1, IGF-1, carcinoembryonic antigen (CEA), alpha-fetoprotein (AFP), prostate specific antigen (PSA), prostate specific membrane antigen (PSMA), cancer antigen 125 (CA-125), interleukin 17, CD154, soluble Interleukin-2 (IL-2) receptor, tyrosinase, MAGE-1, MAGE-2, NY-ESO-1, Melan-A/MART-1, glycoprotein (gp) 75, gp100, beta-catenin, PRAME, MUM-1, ZFP161, Ubiquitin-1, HOX-B6, YB-1, Osteonectin, ILF3, folic acid or a derivative thereof, a tumor necrosis factor (TNF) family member, TNF-alpha, TNF-beta (lymphotoxin, LT), TRAIL, Fas, LIGHT, 41BB, transforming growth factor alpha, transforming growth factor beta, insulin, ceruloplasmin, HIV-tat, a peptide or protein comprising an RGD sequence motif, a mono-saccharide, di-saccharide, oligo-saccharide, sialic acid, galactose, mannose, fucose, or acetyl-neuraminic acid.

Methods performed include, among others, contacting a subject in need of inhibiting, reducing or preventing proliferation, survival, differentiation, death, or activity of a cells, such as a hyperproliferative cell or an undesirably proliferating cell. Exemplary subjects include a subject having or at risk of having undesirable or aberrant cell proliferation; a subject having or at risk of having a benign hyperplasia; or a non-metastatic or metastatic neoplasia, cancer, tumor or malignancy (e.g., a solid or liquid tumor, myeloma, lymphoma, leukemia, carcinoma, sarcoma, melanoma, neural, reticuloendothelial and haematopoietic neoplasia).

In accordance with the invention, there are additionally provided methods of treating a subject having a hyperproliferative disorder and methods of treating a subject having a neoplasia, tumor, cancer or malignancy (metastatic, non-metastatic or benign). In various embodiments, a method includes, administering to a subject an amount of the fusion construct sufficient to treat the hyperproliferative disorder; and administering to a subject an amount of the fusion construct sufficient to reduce or inhibit proliferation of the neoplasia, tumor, cancer or malignancy.

Methods include treating a subject having or at risk of having a metastasis. For example, an amount of a fusion construct effective to reduce or inhibit spread or dissemination of a tumor, cancer or neoplasia to other sites, locations or regions within the subject. In various embodiments, a method reduces or inhibits metastasis of a primary tumor or cancer to one or more other sites, formation or establishment of a metastasis at one or more other sites, locations or regions thereby reducing or inhibiting tumor or cancer relapse or tumor or cancer progression. In further embodiments, a method reduces or inhibits growth, proliferation, mobility or invasiveness of tumor or cancer cells that potentially or do develop metastases (e.g., disseminated tumor cells); reduces or inhibits formation or establishment of metastases arising from a primary tumor or cancer to one or more other sites, locations or regions distinct from the primary tumor or cancer; reduces or inhibits growth or proliferation of a metastasis at one or more other sites, locations or regions distinct from the primary tumor or cancer after the metastasis has formed or has been established; or reduces or inhibits formation or establishment of additional metastasis after the metastasis has been formed or established. In yet another embodiment, a method reduces or inhibits relapse or progression of the neoplasia, tumor, cancer or malignancy.

In accordance with the invention, there are still further provided methods of reducing or inhibiting metastasis of a neoplasia, tumor, cancer or malignancy to other sites, or formation or establishment of metastatic neoplasia, tumor, cancer or malignancy at other sites distal from a primary neoplasia, tumor, cancer or malignancy. In various embodiments, a method includes administering to a subject an amount of the fusion construct sufficient to reduce or inhibit metastasis of the neoplasia, tumor, cancer or malignancy to other sites, or formation or establishment of metastatic neoplasia, tumor, cancer or malignancy at other sites distal from the primary neoplasia, tumor, cancer or malignancy.

Neoplasia, tumor, cancer and malignancy treatable in accordance with the invention include solid cellular mass, hematopoietic cells, or a carcinoma, sarcoma (e.g. lymphosarcoma, liposarcoma, osteosarcoma, chondrosarcoma, leiomyosarcoma, rhabdomyosarcoma or fibrosarcoma), lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic (e.g., myeloma, lymphoma or leukemia) neoplasia, tumor, cancer or malignancy.

Neoplasia, tumor, cancer and malignancy treatable in accordance with the invention can be present in or affect a lung (small cell lung or non-small cell lung cancer), thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, skin or stem cell neoplasia, tumor, cancer, or malignancy.

Methods may be practiced with other treatments or therapies (e.g., surgical resection, radiotherapy, ionizing or chemical radiation therapy, chemotherapy, immunotherapy, local or regional thermal (hyperthermia) therapy, or vaccination). Such treatments or therapies can be administered prior to, substantially contemporaneously with (separately or in a mixture), or following administration of a fusion construct. In one embodiment, a method includes administering an anti-cell proliferative, anti-neoplastic, anti-tumor, anti-cancer or immune-enhancing treatment or therapy. In further embodiments, a method includes administering an alkylating agent, anti-metabolite, plant extract, plant alkaloid, nitrosourea, hormone, nucleoside or nucleotide analog; cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, 5-azacytidine (5-AZC) and 5-azacytidine related compounds, bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol, vinblastine, vincristine, doxorubicin or dibromomannitol, topoisomerase inhibitors, (irinotecan, topotecan, etoposide, teniposide), gemcitabine, pemetrexed etc. Cell or immunotherapies include a lymphocytes, plasma cells, macrophages, dendritic cells, T-cells, NK cells or B-cells; an antibody, a cell growth factor, a cell survival factor, a cell differentiative factor, a cytokine or a chemokine (examples are interleukins IL-2, IL-1α, IL-1β, IL-3, IL-6, IL-7, granulocyte-macrophage-colony stimulating factor (GMCSF), IFN-γ, IL-12, TNF-α, TNFβ, MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAPIIIβ-TG/NAP-2, Mig, PBSF/SDF-1, or lymphotactin) etc.

Additional agents that are applicable with fusion constructs are targeted drugs or biological such as antibodies or small molecules. Non-limiting examples of monoclonal antibodies include rituximab (Rituxan®), trastuzumab (Herceptin), bevacizumab (Avastin), cetuximab (Erbitux), alemtuzumab (Campath), panitumumab (Vectibix), ibritumomab tiuxetan (Zevalin), tositumomab (Bexxar) etc. which can be used in combination with, inter alia, a fusion construct in accordance with the invention. Other targeted drugs that are applicable for use with the fusion constructs are imatinib (Gleevec), gefitinib (Iressa), bortzomib (Velcade), lapatinib (Tykerb), sunitinib (Sutent), sorafenib (Nevaxar), nilotinib (Tasigna) etc.

Methods of the invention include providing a subject with a benefit. In particular embodiments, a method of treatment results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan; results in reducing or decreasing severity, duration or frequency of an adverse symptom or complication associated with or caused by the neoplasia, tumor, cancer or malignancy; results in reducing or decreasing pain, discomfort, nausea, weakness or lethargy; or results in increased energy, appetite, improved mobility or psychological well being.

In accordance with the invention, there are still additionally provided methods of reducing fertility of an animal; methods treating or reducing endometriosis, benign prostate hyperplasia, a fibroid or polyp. In various embodiments, a method includes administering to an animal (e.g., mammal, such as a human) an amount of a fusion construct sufficient to reduce fertility; administering to an animal (e.g., mammal, such as a human) an amount of a fusion construct sufficient to treat or reduce endometriosis; administering to an animal (e.g., mammal, such as a human) an amount of a fusion construct sufficient to treat or reduce benign prostate hyperplasia; and administering to an animal (e.g., mammal, such as a human) an amount of a fusion construct sufficient to treat or reduce a fibroid or polyp.

Subjects treatable in accordance with the methods include mammals. In particular embodiments, a subject is a human.

Fusion constructs more toxic to MDA-MB-435S.luc cells than Phor21-βCG-ala are listed to the right of the figure.

Figure 4:
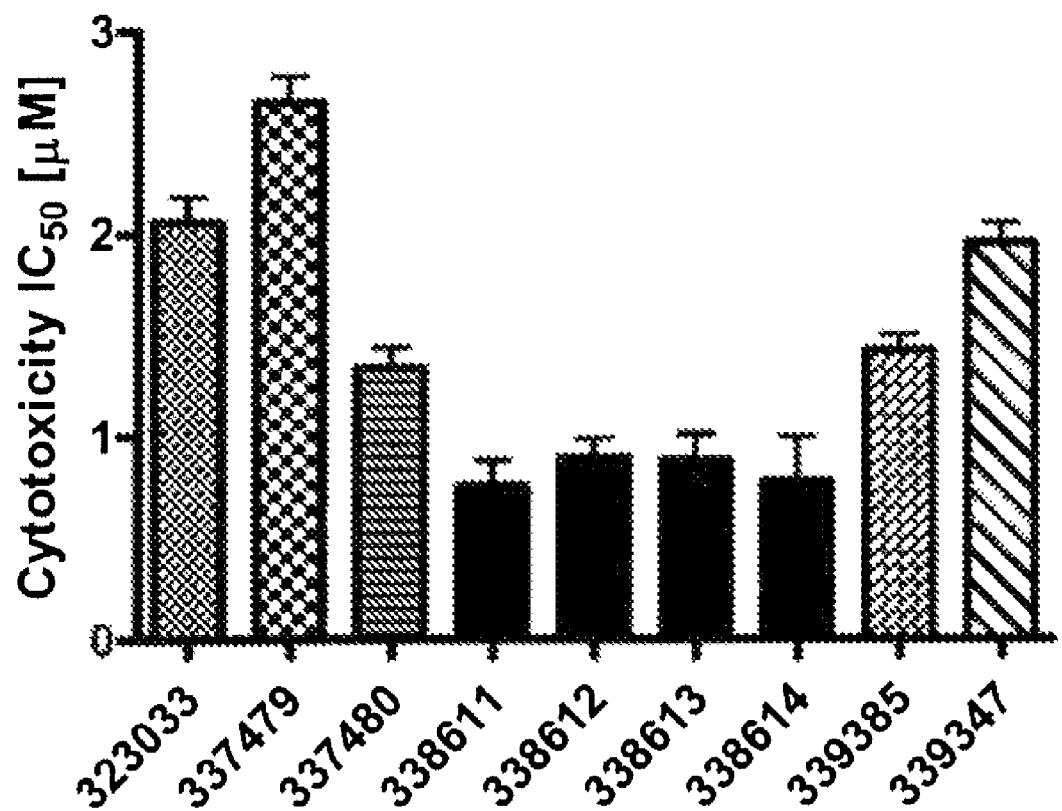

FIG. 4 shows cytotoxicity to MDA-MB-435S.luc cell (micromolar IC$_{50}$) of LHRH fusion constructs. The fusion constructs are: 323033=Phor21-βCG-ala, 337479=LHRH-Phor21, 337480=Phor21-LHRH, 338611=D-ala-Phor21-LHRH, 338612=Phor18-ASAAS(SEQ. ID NO. 11)-LHRH, 338613=Phor18-LHRH, 339385=D-ala-Phor18-LHRH, and 339347=Phor18-Lupron.

Figure 5:
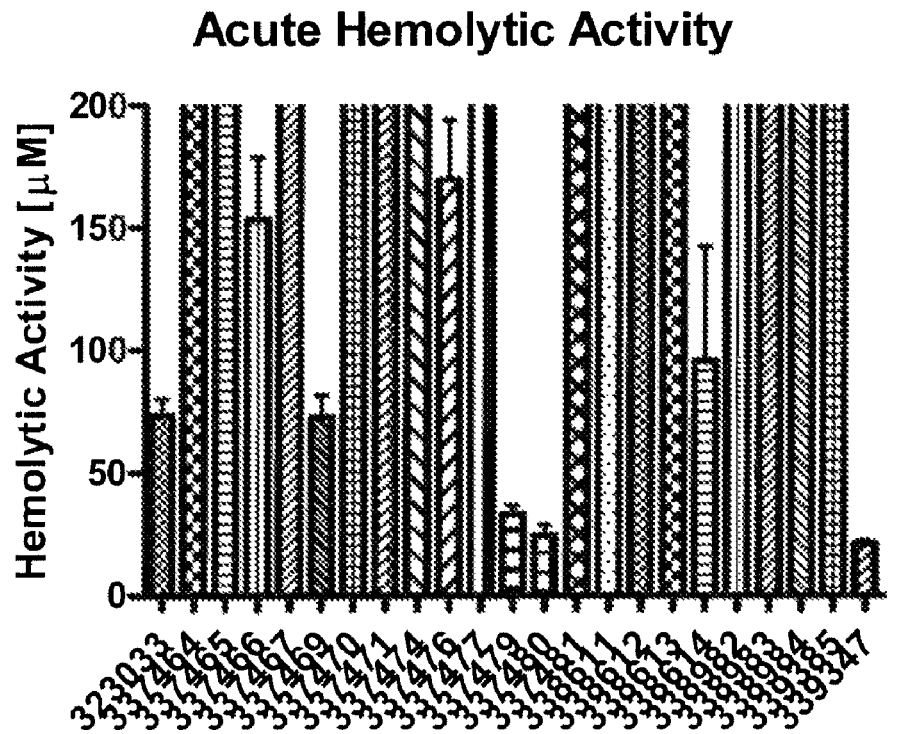
Figure 5:
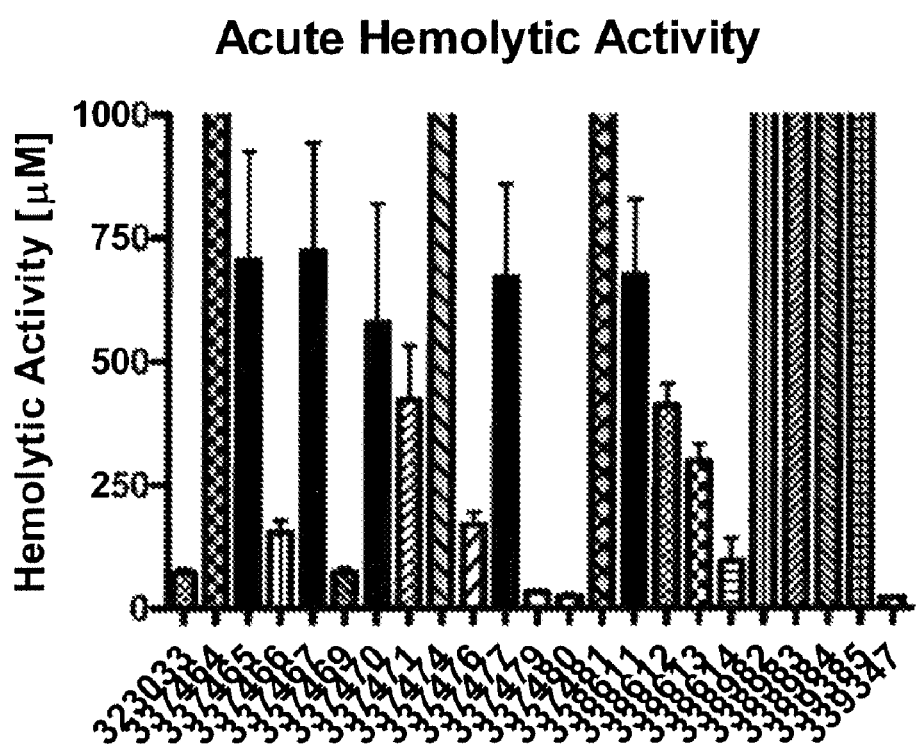

FIG. 5 shows acute hemolytic activity (micromolar HA$_{50}$) of βCG-ala and LHRH fusion constructs to human red blood cells compared to Phor21-βCG-ala. All fusion constructs had significantly lower hemolytic activity than Phor21-βCG-ala, except for LHRH-Phor21, Phor21-LHRH and Phor18-Lupron (QHWSY(D-Leu)LRPNEt=Lupron (SEQ. ID NO. 17).

Figure 6:
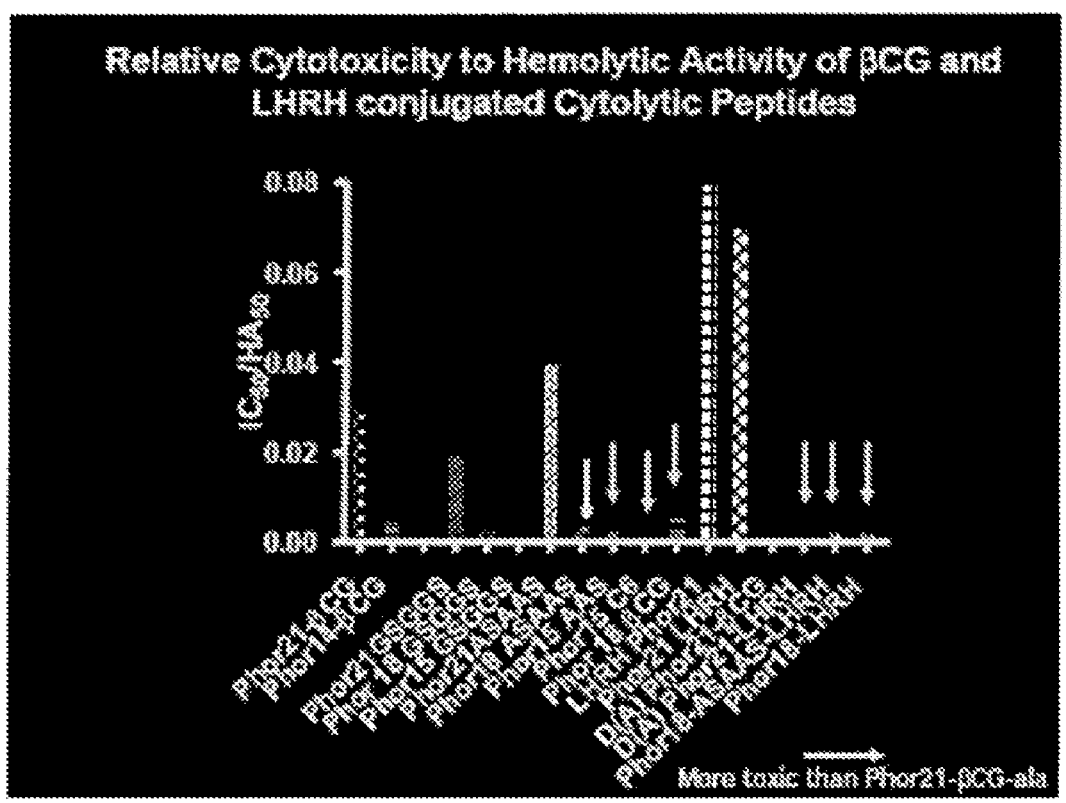

FIG. 6 shows a comparison of cytotoxicity and hemolytic activity. Peptides indicated with arrows are more toxic to cells than Phor21-βCG-ala.

Figure 7:
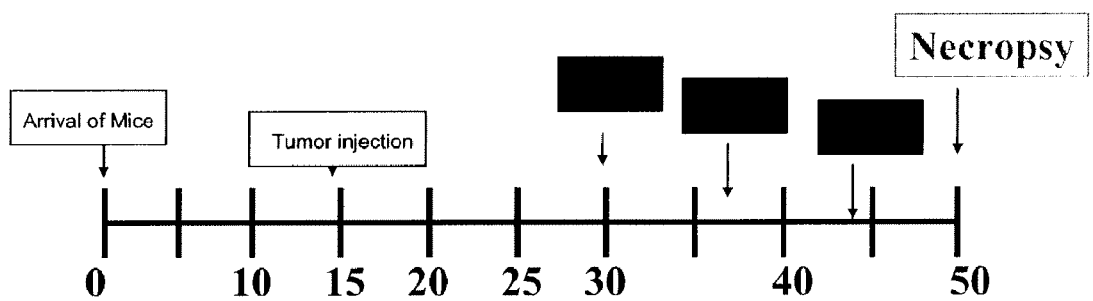

FIG. 7 is a treatment schedule outline.

FIGS. 8A-8J is a summary of tumor conditions during treatment and at study endpoint with 3 βCG conjugates in comparison to unconjugated Phor21, unconjugated Phor18 (338983)=(CLIP71) and an (KKKFAFA)$_3$ (SEQ. ID NO. 16) conjugate (338984). Fusion construct codes, 33=Phor21β-CG-ala; 76=Phor18-βCG-a1a; 81=D-ala-Phor21-βCG-a1a; 85=D-ala-Phor18-LHRH; 47=Phor18-Lupron; 13=Phor18-LHRH; 11=D-ala-Phor21-LHRH; 12=Phor18-ASAAS (SEQ. ID NO. 11)-LHRH; 12=Phor18-ASAAS-LHRH; 71=Phor15-βCG-ala; and 74=Phor15-C6-βCG-ala are followed by amounts of the construct used in the study.

FIGS. 9A-9H show tumor volume of treatment groups compared to saline and baseline values for A) Phor21-βCG-ala (33); B) D-ala-Phor21-LHRH (11); C) Phor18-Lupron (47); D) Phor18-ASAAS—(SEQ. ID NO. 11) LHRH (12); E) Phor18-LHRH (13); F) (KKKFAFA)$_3$ (SEQ. ID NO. 16)-LHRH; G) D-ala-Phor18-LHRH (85) at the indicated time periods up to 30 days; and H) compared to baseline.

FIGS. 10A-10E show a summary of tumor conditions at study endpoint with 5 LHRH conjugates in comparison to Phor21-βCG-ala for A) Tumor weights, B) Tumor weight change compared to baseline, C) Total number of live tumor cells, D) changes of total number of live tumor cells compared to baseline, and E) bodyweights. 338614=(KKKFAFA)$_3$ (SEQ. ID NO. 16) LHRH, 338612=Phor18-ASAAS—(SEQ. ID NO. 11)-LHRH, 338613=Phor18-LHRH, and 339385=D-ala-Phor18-LHRH.

Figure 11:
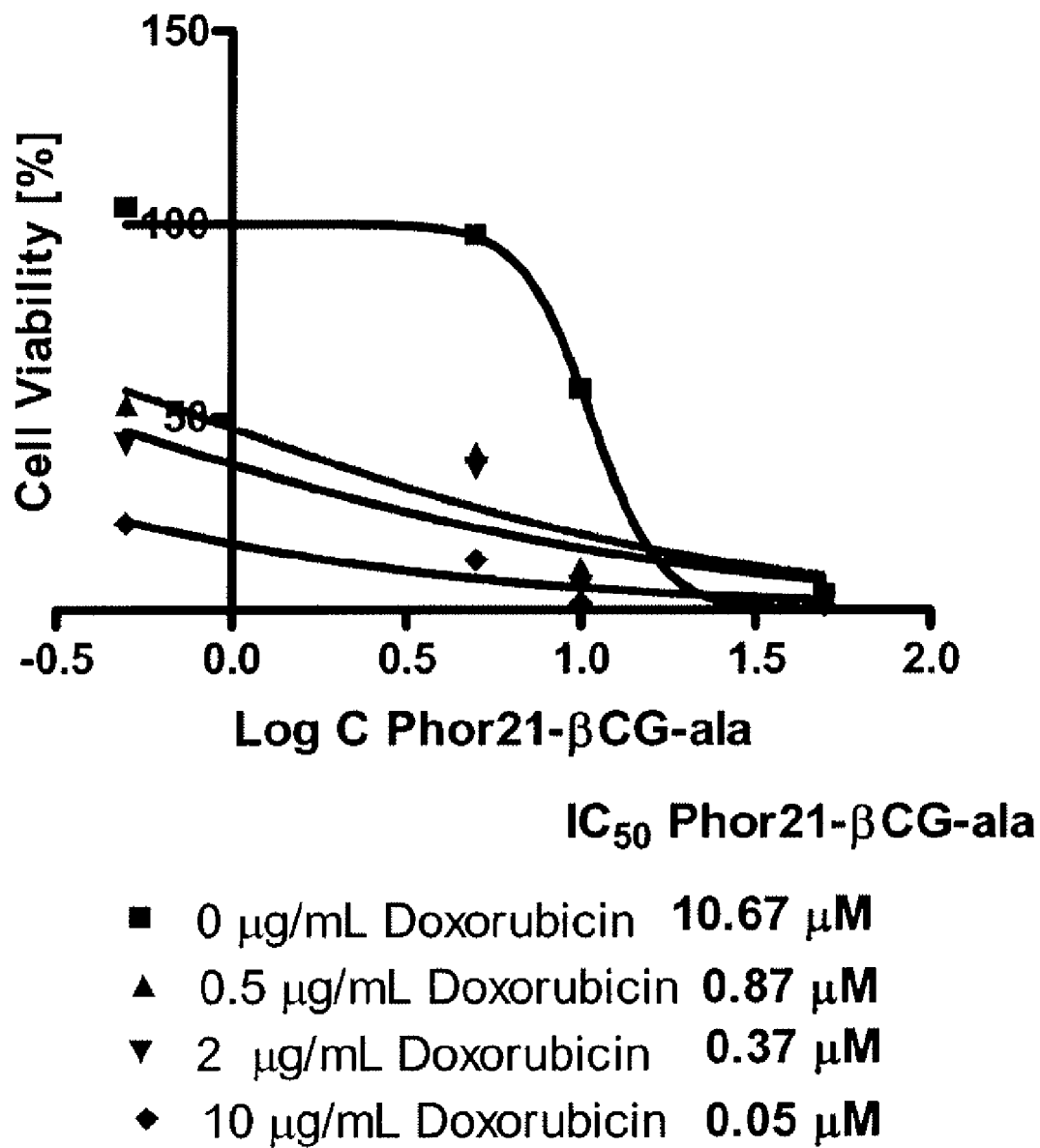

FIG. 11 shows ovarian cancer cells (OVCAR 3), which are multi-drug resistant, incubated with increasing concentrations of Phor21-βCG-ala in the presence of Doxorubicin at the indicated amounts, and potentiation of cell killing by a factor of 200 at the highest doxorubicin concentration by the combination.

Figure 12:
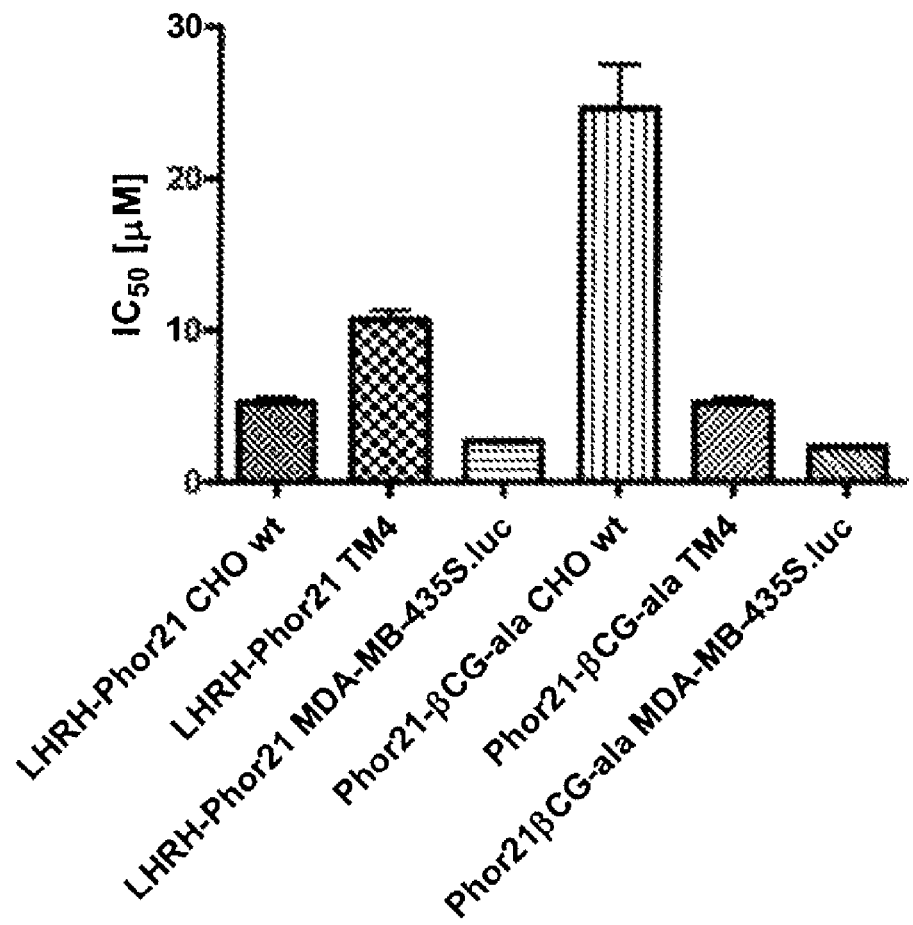

FIG. 12 shows CHO (Chinese Hamster Ovary) and TM4 cell cytotoxicity in comparison to MDA-MB-435S.luc cells with LHRH and Phor21 and βCG and Phor21 fusion constructs. TM4 cells are LHRH receptor negative, CHO cells are CG receptor negative, and MDA-MB-435S.luc cells express both LHRH and CG receptors.

DETAILED DESCRIPTION

The invention is based at least in part on a fusion construct that includes a first domain lytic portion joined or fused to a second domain binding portion. In a typical configuration, a fusion construct first domain includes a lytic portion, which is directly or indirectly toxic to a cell, which can thereby reduce cell proliferation or survival, or stimulate, induce, increase or enhance cell death, killing or apoptosis; and a fusion construct second domain includes a portion that targets a cell, referred to as a binding moiety entity.

In accordance with the invention, there are provided fusion constructs that include or consist of a first "lytic" domain and include or consist of a second "targeting" or "binding" domain. In one embodiment, a fusion construct includes a first domain consisting of a 12, 13, 15, 16, 17, 18, 19, 20, 22, 23, 24, 25, 26, 27 or 28 residue L- or D-amino acid sequence that includes a peptide sequence (selected from amino acids such as Lysine=K, Phenylalanine=F and Alanine=A), for example, KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAKKFAKFAK (SEQ. ID NOs. 1 to 7), and a second domain that includes or consists of a targeting or binding moiety. In another embodiment, a fusion construct includes a first domain consisting of an L- or D-amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAKKFAKFAK (SEQ. ID NOs. 1 to 7), and a second domain that includes or consist of a targeting or binding moiety. In a further embodiment, a fusion construct includes or consists of a first domain consisting of an L- or D-amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAKKFAKFAK (SEQ. ID NOs. 1 to 7), and a second domain consisting of a 1-25 L- or D-amino acid sequence (e.g., targeting or binding moiety) distinct from said first domain.

As used herein, the term "fusion" or "chimeric" and grammatical variations thereof, when used in reference to a construct, means that the construct contains portions or sections that are derived from, obtained or isolated from, or are based upon or modeled after two different molecular entities that are distinct from each other and do not typically exist together in nature. That is, for example, one portion of the fusion construct includes or consists of a lytic portion and a second portion of the construct includes or consists of a targeting portion, such as a moiety that has binding capability, each of first and second domains structurally distinct. A fusion construct can also be referred to as a "conjugate," wherein the conjugate includes or consists of a first domain lytic portion and a second domain targeting or binding moiety.

First domains and or second domains of fusion constructs include or consist of amino acid sequences (peptides, polypeptides, proteins, lectins), nucleic acids (DNA, RNA) and carbohydrates (saccharides, sialic acid, galactose, mannose, fucose, acetylneuraminic acid, etc.). The terms "amino acid sequence," "protein," "polypeptide" and "peptide" are used interchangeably herein to refer to two or more amino acids, or "residues," covalently linked by an amide bond or equivalent. Amino acid sequences can be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, N.Y.).

First and second domains of a fusion construct or chimera include L-amino acid sequences, D-amino acid sequences and amino acid sequences with mixtures of L-amino acids and D-amino acids. Amino acid sequences of first and second domains can be a linear or a cyclic structure, conjugated to a distinct moiety (e.g., third, fourth, fifth, sixth, seventh, etc. domains), form intra or intermolecular disulfide bonds, and also form higher order multimers or oligomers with the same or different amino acid sequence, or other molecules.

Exemplary lengths of fusion constructs are from about 5 to 15, 20 to 25, 25 to 50, 50 to 100, 100 to 150, 150 to 200, or 200 to 300 or more amino acid residues in length. In particular embodiments, a first or second domain includes or consists of an amino acid sequence of about 1 to 10, 10 to 20, 15 to 20, 20 to 30, 30 to 40, 40 to 50, 60 to 70, 70 to 80, 80 to 90, 90 to 100 or more residues. In more particular embodiments, a first domain consists of a 15, 16, 17, 18, 19, 20, 28 or more residue amino acid sequence.

Fusion construct first domains, alone or in combination with a second domain, optionally form an amphipathic alpha-helix. An amphipathic alpha-helix contains mostly hydrophilic amino acids on one side of the alpha-helix and the other side contains mostly hydrophobic amino acids. Since the alpha helix makes a complete turn for every 3.6 residues, the amino acid sequence of an amphipathic alpha helix alternates between hydrophilic and hydrophobic residues every 3 to 4 residues. A PNNPNNP repeat pattern or motif is predicted to form an amphipathic alpha-helix where P represents a positively charged amino acid residue and N a neutral amino acid residue. A PNNPNNP (SEQ. ID NO. 14) repeat pattern or motif is predicted to form an amphipathic alpha-helix where P represents a positively charged amino acid residue and N a neutral amino acid residue. A PNNPNNP (SEQ. ID NO. 14) repeat pattern provides a cationic binding site for the lytic peptide to a negatively charged cell membrane and a hydrophobic site for membrane interaction/penetration. Fusion constructus therefore include first domains with one or more uninterrupted PNNPNNP (SEQ. ID NO. 14) repeat patterns or motifs, or one or more interrupted PNNPNNP (SEQ. ID NO. 14) repeat patterns or motifs, which can form an amphipathic alpha-helix. For example, a 15 or 18 residue amino acid sequence, such as KFAKFAKKFAKFAKK and KFAKFAKKFAKFAKKFAK (SEQ. ID NOs. 1 and 4), has uninterrupted and interrupted PNNPNNP repeat motifs.

A fusion construct second domain, such as a targeting or binding moiety, includes or consists of a ligand, antibody (or an antigen-binding fragment thereof), antigen, integrin, integrin receptor (e.g., proteins or peptides containing "RGD" sequence motif, and components that may be present in extracellular matrix (ECM), such as mono-, di- or oligo-saccharides, sialic acid, galactose, mannose, fucose, acetylneuraminic acid), growth factor, cytokine, chemokine, and targeting and binding moieties that bind to receptors, antibodies, antigens, integrins, integrin receptors (e.g., proteins or peptides containing "RGD" sequence motif, and components that may be present in extracellular matrix (ECM), such as mono-, di- or oligo-saccharides, sialic acid, galactose, mannose, fucose, acetylneuraminic acid), growth factor receptors, cytokine receptors, and chemokine receptors.

A "receptor" is typically present on (e.g., a membrane receptor) or within a cell. A receptor may associate with the cell membrane surface or traverse the cell membrane. For example, a receptor protein can have a transmembrane domain that traverses the cell membrane, optionally with a portion that is cytoplasmic or extracellular, or both. Receptors therefore include full length intact native receptors containing an extracellular, transmembrane or cytoplasmic portion, as well as truncated forms or fragments thereof (e.g., an extracellular, transmembrane or cytoplasmic portion or subsequence of the receptor alone, or in combination). For example, a soluble receptor typically lacks a transmembrane and may optionally also lack all or a part of the native extracellular or cytoplasmic region (if present in native receptor). Such truncated receptor forms and fragments can retain at least partial binding to a ligand.

Targeting and binding moiety domains of fusion constructs include or consist of any entity that binds to a receptor, denoted a receptor ligand, specifically or non-specifically. Non-limiting examples of targeting and binding moieties therefore include hormone, a hormone analogue, a fragment of a hormone or hormone analogue that binds to a hormone receptor, a growth factor, growth factor analog, a fragment of a growth factor or growth factor analogue that binds to a receptor, a hormone receptor or a ligand that binds to a hormone or to a hormone receptor, and targeting and binding moieties that bind to a hormone, a hormone analogue, a fragment of a hormone or hormone analogue that binds to a hormone receptor, a hormone receptor or a ligand that binds to a hormone or to a hormone receptor, growth factor, growth factor analogue, a fragment of a growth factor or growth factor analogue that binds to a receptor, a growth factor receptor or a ligand that binds to a growth factor or to a growth factor receptor, etc.

Exemplary hormones useful as binding moieties include gonadotropin-releasing hormone I, gonadotropin-releasing hormone II, lamprey III luteinizing hormone releasing hormone, luteinizing hormone beta chain, luteinizing hormone (LH), chorionic gonadotropin (CG), chorionic gonadotropin beta subunit (β- or beta-CG), melanocyte stimulating hormone, estradiol, diethylstilbestrol, dopamine, somatostatin, follicle-stimulating hormone (FSH), glucocorticoids, estrogens, testosterone, adrostenedione, dihydrotestosterone, dehydroepiandrosterone, progesterones, androgens and derivatives thereof. Exemplary hormone receptors useful as binding moieties include gonadotropin-releasing hormone I receptor, gonadotropin-releasing hormone II receptor, lamprey III luteinizing hormone releasing hormone receptor, luteinizing hormone receptor, chorionic gonadotropin receptor, melanocyte stimulating hormone receptor, estradiol receptor, dopamine receptor, somatostatin receptor, follicle-stimulating hormone (FSH) receptor, epidermal growth factor (EGF) receptor, growth hormone (GH) receptor, Her2-neu receptor, glucocorticoid hormone receptor, estrogen receptor, testosterone receptor, progesterone receptor and androgen receptor.

Exemplary growth factors include epidermal growth factor (EGF), growth hormone (GH), and Her2-neu. Exemplary growth factor receptors include epidermal growth factor (EGF) receptor, growth hormone (GH) receptor, and Her2-neu receptor, IGF-1.

Specific non-limiting examples of targeting or binding moieties include LHRH, LHRH functional (binding) fragments thereof, LHRH analogues, and βCG, βCG functional (binding) fragments thereof and βCG analogs. LHRH is a fully functional ligand and can elicit pharmacological effects through ligand receptor interaction, such as activation of signal transduction pathways. βCG-ala is a fragment of hCG that can bind to the cell membrane without eliciting any pharmacological effect. Specific non-limiting examples of targeting or binding moieties include or consist of an amino acid sequence within or set forth as: (SEQ. ID NO. 8, SEQ. ID NO. 13, and SEQ. ID NO. 9) SYAVALSAQAALARR; SYAVALSAQAALARRA, which are fragments of βCG, and QHWSYGLRPG, which is an LHRH sequence.

Targeting and binding moities further include antigens for ligands expressed exclusively or preferentially in neoplastic, tumor or cancer cells, and lymphatic or blood vessels associated with neoplastic, tumor or cancer cells. Such antigens can be conveniently referred to as "tumor associated antigens," or "TAA", and include carcinoembryonic antigen (CEA), alpha-fetoprotein (AFP), prostate specific antigen (PSA), prostate specific membrane antigen (PSMA), CA-125 (residual epithelial ovarian cancer), soluble Interleukin-2 (IL-2) receptor, RAGE-1, tyrosinase, MAGE-1, MAGE-2, NY-ESO-1, Melan-A/MART-1, glycoprotein (gp) 75, gp100, beta-catenin, PRAME, MUM-1, ZFP161, Ubiquilin-1, HOX-B6, YB-1, Osteonectin, and ILF3, IGF-1, to name a few. Other antigens that can be targeted are CD19, CD20, CD23, CD27, CD28, CD30, CD33, CD40, CD52, CD56, CD70, CD154, immunoglobulin-like receptors etc).

Targeting and binding moities additionally include transferrin, folic acid and derivatives thereof (e.g., folate), and tumor necrosis factor (TNF) family members and TNF receptors, such as TNF-alpha, TNF-beta (lymphotoxin, LT), TRAIL, Fas, LIGHT, 41BB.

Fusion constructs in which a second domain includes or consists of a targeting or binding domain can bind to a cell that produces or expresses an antigen, receptor or ligand, integrin, antibody or antigen, or TAA to which the second domain binds. Non-limiting examples of cells include hyperproliferative cells and cells that exhibit aberrant or undesirable hyperproliferation. In particular non-limiting examples, such cells include non-metastatic and metastatic neoplastic, cancer, tumor and malignant cells, as well as disseminated neoplastic, cancer, tumor and malignant cells and dormant neoplastic, cancer, tumor and malignant cells. Cells that express an antigen, receptor, ligand, integrin, TAA, etc., at elevated levels relative to normal or non-hyperproliferating cells provide selectivity for such cells. Thus, a targeting or binding moiety can bind to an antigen, receptor, ligand, integrin or TAA that is expressed in or produced by a hyperproliferative cell (e.g., non-metastatic and metastatic neoplasias, cancers, tumors and malignancies, and disseminated and dormant neoplastic, cancer, tumor and malignant cells), but not detectably expressed or is produced or expressed at relatively lower levels by a normal or non-hyperproliferative cell, thereby preferentially targeting hyperproliferative cells. Exemplary non-limiting cell and tissue types that express an antigen, receptor, ligand, integrin or TAA include a breast, ovarian, uterine, cervical, prostate, testicular, adrenal, pituitary, pancreatic, hepatic, gastrointestinal, skin, muscle or endometrial cell.

Additional examples of binding moieties include antibodies and antibody fragments. An "antibody" refers to any monoclonal or polyclonal immunoglobulin molecule, such as IgM, IgG, IgA, IgE, IgD, and any subclass thereof. Exemplary subclasses for IgG are $IgG_1$, $IgG_2$, $IgG_3$ and $IgG_4$. Antibodies include those produced by or expressed on cells, such as B cells. An antibody fragment or subsequence refers to a portion of a full length antibody that retains at least partial antigen binding capability of a comparison full length antibody. Exemplary antibody fragments include Fab, Fab', $F(ab')_2$, Fv, Fd, single-chain Fv (scFv), disulfide-linked Fvs (sdFv), $V_L$, $V_H$, trispecific ($Fab_3$), bispecific ($Fab_2$), diabody (($V_L$-$V_H$)$_2$ or ($V_H$-$V_L$)$_2$), triabody (trivalent), tetrabody (tetravalent), minibody (($scF_V$-$C_H3$)$_2$), bispecific single-chain Fv (Bis-scFv), IgGdeltaCH2, scFv-Fc, (scFv)$_2$-Fc, or other antigen binding fragment of an intact immunoglobulin.

Fusion constructs include those with a first domain at the amino-terminus and a second domain at the carboxyl-terminus. Fusion constructs also include those with a first domain at the carboxyl-terminus and a second domain at the amino-terminus. Where additional domains are present (e.g., third, fourth, fifth, sixth, seventh, etc. domains), a first domain is positioned at the $NH_2$-terminus relative to a second domain, or a second domain is positioned at the $NH_2$-terminus relative to a first domain.

Subsequences and amino acid substitutions of the various sequences set forth herein, such as, KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAKKFAKFAK (SEQ. ID NOs. 1 to 7), or a binding moiety, are also included. In particular embodiments, a subsequence of a first or second domain has at least 5 to 10, 10 to 15, 15 to 20, 20 to 25, 25 to 30, 30 to 35 or more amino acid residues.

The invention therefore includes modifications or variations, such as substitutions, additions or deletions of a first or second domain, or both first and second domains. Thus, a fusion construct that includes a peptide sequence first or second domain can incorporate any number of conservative or non-conservative amino acid substitutions, as long as such substitutions do not destroy activity (lytic or binding) of first or second domains. Thus, for example, a modified lytic portion (first domain) can retain at least partial lytic activity, such as cell killing or apoptosis, of an unmodified first domain, and a modified binding moiety or mimetic thereof can retain at least a partial binding activity of an unmodified binding moiety.

A "conservative substitution" is a replacement of one amino acid by a biologically, chemically or structurally similar residue. Biologically similar means that the substitution is compatible with a biological activity, e.g., lytic activity. Structurally similar means that the amino acids have side chains with similar length, such as alanine, glycine and serine, or having similar size, or the structure of a first, second or additional domain is maintained, such as an amphipathic alph helix. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc. Routine assays can be used to determine whether a fusion construct variant has activity, e.g., lytic activity or binding activity.

Specific examples include a substitution or deletion of one or more amino acid (e.g., 1-3, 3-5, 5-10, 10-20, or more) residues of a peptide first or second domain. A modified fusion construct can have a peptide sequence with 50%, 60%, 70%, 75%, 80%, 85%, 90%, 95%, 96%, 97%, 98%, or more identity to a reference sequence (e.g., a first domain, such as KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAKKFAKFAK (SEQ. ID NOs. 1 to 7), or a second domain such as a binding moiety).

In a particular embodiment, a fusion construct includes a peptide first domain that includes or consists of a 12, 13, 15, 16, 17, 18, 19, 20, 22, 23, 24, 25, 26, 27 or 28 residue L- or D-amino acid sequence that includes a peptide selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAK- FAKKFAKFAK (SEQ. ID NOs. 1 to 7) having one or more of the K residues substituted with an F or L residue, one or more of the F residues substituted with a K, A or L residue, or one or more of the A residues substituted with a K, F or L residue. In another particular embodiment, a fusion construct includes a peptide first domain consisting of an L- or D-amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7) having one or more of the K residues substituted with an F or L residue, one or more of the F residues substituted with a K, A or L residue, or one or more of the A residues substituted with a K, F or L residue; and a peptide second domain that includes or consists of a binding moiety. In further particular embodiment, a fusion construct includes or consists of a peptide first domain consisting of an L- or D-amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7) having one or more of the K residues substituted with any of an F or L residue, one or more of the F residues substituted with any of a K, A or L residue, or one or more of the A residues substituted with any of a K, F or L residue, and a peptide second domain consisting of a 1-25 L- or D-amino acid sequence (e.g., binding moiety) distinct from the first domain.

The term "identity" and "homology" and grammatical variations thereof mean that two or more referenced entities are the same. Thus, where two amino acid sequences are identical, they have the same amino acid sequence. "Areas, regions or domains of identity" mean that a portion of two or more referenced entities are the same. Thus, where two amino acid sequences are identical or homologous over one or more sequence regions, they share identity in these regions. The term "complementary," when used in reference to a nucleic acid sequence means the referenced regions are 100% complementary, i.e., exhibit 100% base pairing with no mismatches.

Due to variation in the amount of sequence conservation between structurally and functionally related proteins, the amount of sequence identity required to retain a function or activity (e.g., lytic or binding) depends upon the protein, the region and the function or activity of that region. For example, for a lytic peptide sequence multiple PNNPNNP (SEQ. ID NO. 14) sequence repeat patterns or motifs can be present, but one or more interrupted or non-interrupted PNNPNNP (SEQ. ID NO. 14) sequence repeat patterns or motifs need not be present.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Nat. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Individual residues and first, second and additional domains can be joined by a covalent or a non-covalent bond. Non-limiting examples of covalent bonds are amide bonds, non-natural and non-amide chemical bonds, which include, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to amide bonds include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, N.Y.).

First and second domains can be fused or joined immediately adjacent to each other by a covalent or a non-covalent bond. First and second domains can be separated by an intervening region, such as a hinge, spacer or linker positioned between a first and a second domain. In one embodiment, a first and second domain are joined by a carbon chain. Multi-carbon chains include carboxylic acids (e.g., dicarboxylic acids) such as glutaric acid, succinic acid and adipic acid.

In another embodiment, a first and second domain are joined by an amino acid, peptide or a non-peptide hinge, spacer or linker positioned between the first and second domains. Peptide hinge, spacer or linker sequences can be any length, but typically range from about 1-10, 10-20, 20-30, 30-40, or 40-50 amino acid residues. In particular embodiments, a peptide hinge, spacer or linker positioned between a first and second domain is from 1 to 25 L- or D-amino acid residues, or 1 to 6 L- or D-amino acid residues. Particular amino acid residues that are included in sequences positioned between the first and second domains include one or more of or C, A, S or G amino acid residues. Specific non-limiting examples of peptides positioned between the first and second domains include a sequence within or set forth as: GSGGS (SEQ. ID NO.10), ASAAS(SEQ. ID NO.11), or CCCCCC (SEQ. ID NOs.10 to 12). Derivatives of amino acids and peptides can be positioned between the first and second domain. A specific non-limiting example of an amino acid derivative is a lysine derivative, or a 6 carbon linker such as α-amino-caproic acid.

Fusion constructs with or without a hinge, spacer or linker, or a third, fourth, fifth, sixth, seventh, etc. domain can be entirely composed of natural amino acids or synthetic, non-natural amino acids or amino acid analogues, or can include derivatized forms. In various embodiments, a fusion construct includes in a first or second domain one or more D-amino acids substituted for L-amino acids, mixtures of D-amino acids and L-amino acids, or a sequence composed entirely of D-amino acid residues.

Fusion constructs can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., an alpha helix conformation. Fusion constructs include cyclic structures such as an end-to-end amide bond between the amino and carboxy-terminus of the molecule or intra- or inter-molecular disulfide bond(s). Fusion constructs may be modified in vitro or in vivo, e.g., post-translationally modified to include, for example, sugar or carbohydrate residues, phosphate groups, fatty acids, lipids, etc.

Specific examples of an addition include a third, fourth, fifth, sixth or seventh domain. Fusion constructs with a first and second domain therefore include one or more additional domains (third, fourth, fifth, sixth, seventh, etc.) covalently linked thereto to impart a distinct or complementary function or activity. Exemplary additional domains include domains facilitating isolation, which include, for example, metal chelating peptides such as polyhistidine tracts and histidine-tryptophan modules that allow purification on immobilized metals; protein A domains that allow purification on immobilized immunoglobulin; and domain utilized in the FLAGS extension/affinity purification system (Immunex Corp, Seattle Wash.). Optional inclusion of a cleavable sequence such as Factor Xa or enterokinase between a purification domain and the fusion construct can be used to facilitate purification. For example, an expression vector can include a fusion construct-encoding nucleic acid sequence linked to six histidine residues followed by a thioredoxin and an enterokinase cleavage site. The histidine residues facilitate detection and purification of the fusion construct while the enterokinase cleavage site provides a means for purifying the construct from the remainder of the protein (see e.g., Kroll, *DNA Cell. Biol.* 12:441 (1993)).

Fusion construct activity can be affected by various factors and therefore fusion constructs can be designed or optimized by taking into consideration one or more of these factors. Such factors include, for example, length of a fusion construct, which can affect toxicity to cells. In particular, increased cytotoxicity was observed when Phor21-βCG-ala and Phor21 were compared to Phor14-βCG-ala. Cell killing activity of alpha helix forming lytic peptide domains can also depend on the stability of the helix. Hinge and spacers can affect membrane interaction of a first domain and the helical structure of a peptide lytic domain. For example, shorter fusion constructs, such as constructs less than 21 amino acids that optionally include a spacer or hinge, can exhibit increased cytotoxicity due to increased helix stability. In particular, spacers such as ASAAS(SEQ. ID NO. 11) and 6 aminocaproic acid tend to increase toxicity of shorter fusion constructs. The charge of lytic peptide domains, which is determined in part by the particular amino acid residues present in the domain, also affects cell killing potency.

The positioning of the binding moiety relative to the lytic domain (N- or C-terminus) also can affect cell killing activity of fusion constructs. For example, a binding moiety positioned at the C-terminus relative to the lytic domain had greater cell killing activity than if positioned at the N-terminus relative to the lytic domain.

Fusion construct in vivo half-life can be increased by constructing fusion construct peptide domains with one or more non-naturally occurring amino acids or derivatives. For example, fusion constructs with D-amino acids (e.g., up to 30% or more of all residues are D-enantiomers) are resistant to serum proteolysis and therefore can be active for longer times thereby increasing in vivo potency. Furthermore, constructing fusion construct peptide domains with one or more non-naturally occurring amino acids or derivatives can reduce hemolytic activity. Such fusion constructs with D-enantiomers also have a greater tendency to be monomeric in solution—they do not significantly aggregate.

In accordance with the invention, there are provided fusion constructs that have greater anti-cell proliferative activity than one or more of Phor21-βCG-ala, Phor21-GSGGS (SEQ. ID NO. 10)-βCG-ala, Phor21-ASAAS(SEQ. ID NO. 11)-βCG-ala, or Phor 14-βCG-ala, as ascertained by a lower $IC_{50}$ value, which represents the amount of fusion construct required to achieve cell cytotoxicity. In accordance with the invention, there are also provided fusion constructs that have less hemolytic activity, as represented by $IC_{50}/HA_{50}$ (hemolytic activity) ratio, than Phor21-βCG-ala, Phor21-GSGGS(SEQ. ID NO. 10)-βCG-ala, Phor21-ASAAS(SEQ. ID NO. 11)-βCG-ala, or Phor 14-βCG-ala. In accordance with the invention, there are further provided fusion constructs that have a hemolytic activity, as represented by $IC_{50}/HA_{50}$ (hemolytic activity) ratio, of less than about 0.02, 0.01, or 0.005. Representative assay conditions for determining cell cytotoxicity and hemolytic activity are set forth in Example 1.

Peptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3 (1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

The invention further provides nucleic acids encoding the fusion constructs of the invention and vectors that include nucleic acid that encodes fusion constructs. In a particular embodiment, a nucleic acid encodes a fusion construct that includes a first domain consisting of a 12, 13, 15, 16, 17, 18, 19, 20, 22, 23, 24, 25, 26, 27 or 28 residue amino acid sequence that includes a peptide sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7), and a second domain that includes or consists of a targeting or binding moiety. In another embodiment, a nucleic acid encodes a fusion construct that includes a first domain consisting of an amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7), and a second domain that includes or consist of a targeting or binding moiety. In a further embodiment, a nucleic acid encodes a fusion construct that includes or consists of a first domain consisting of an amino acid sequence selected from KFAKFAKKFAKFAKK, KFAKFAKKFAKFAKKF, KFAKFAKKFAKFAKKFA, KFAKFAKKFAKFAKKFAK, KFAKFAKKFAKFAKKFAKF, KFAKFAKKFAKFAKKFAKFA and KFAKFAKKFAKFAKKFAKFAK (SEQ. ID NOs. 1 to 7), and a second domain consisting of a 1-25 amino acid sequence (e.g., targeting or binding moiety) distinct from said first domain.

Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA, cDNA, and antisense. RNA nucleic acid can be spliced or unspliced mRNA, rRNA, tRNA or antisense. Nucleic acids include naturally occurring, synthetic, as well as nucleotide analogues and derivatives.

As a result of the degeneracy of the genetic code, nucleic acids include sequences degenerate with respect to sequences encoding fusion constructs of the invention. Thus, degenerate nucleic acid sequences encoding fusion constructs are provided.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through sequencing, gel electrophoresis, UV spectrometry.

Nucleic acids may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

Nucleic acids may be inserted into a plasmid for propagation into a host cell and for subsequent genetic manipulation if desired. A plasmid is a nucleic acid that can be stably propagated in a host cell; plasmids may optionally contain expression control elements in order to drive expression of the nucleic acid. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of fusion construct encoding nucleic acids, producing fusion constructs or antisense nucleic acid, and expressing fusion constructs in host cells and organisms, for example.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a fusion construct in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzmology*, 153: 516 (1987), eds. Wu & Grossman; Bitter *Methods in Enzymology*, 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is cotransfected into a host cell with a first vector containing a nucleic acid encoding a fusion construct.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk-, hgprt- or aprt-cells, respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1 (1981)); puromycin; and hygromycin gene, which confers resistance to hygromycin (Santerre et al., *Gene* 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: Current Communications in Molecular Biology, Cold Spring Harbor Laboratory).

Host cells that express fusion constructs, and host cells transformed with nucleic acids encoding fusion constructs and vectors including a nucleic acid that encodes the fusion construct are also provided. In one embodiment, a host cell is a prokaryotic cell. In another embodiment, a host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded fusion construct expressed. The term also includes any progeny or subclones of the host cell. Host cells include cells that express fusion construct and cells that do not express fusion construct. Host cells that do not express a fusion construct are used to propagate nucleic acid or vector which includes a nucleic acid encoding a fusion construct or an antisense.

Host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression.

Fusion constructs, nucleic acids encoding fusion constructs, vectors and host cells expressing fusion constructs or transformed with nucleic acids encoding fusion constructs and antisense include isolated and purified forms. The term "isolated," when used as a modifier of an invention composition, means that the composition is made by the hand of man or is separated, substantially completely or at least in part, from the naturally occurring in vivo environment. Generally, an isolated composition is substantially free of one or more materials with which it normally associates with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. The term "isolated" also does not exclude forms (e.g., pharmaceutical formulations and combination compositions) in which there are combinations therein, any one of which is produced by the hand of man.

An "isolated" composition can also be "purified" when free of some, a substantial number of, most or all of the materials with which it typically associates with in nature. Thus, an isolated fusion construct that also is substantially pure does not include polypeptides or polynucleotides present among millions of other sequences, such as proteins of a protein library or nucleic acids in a genomic or cDNA library, for example. A "purified" composition can be combined with one or more other molecules.

In accordance with the invention, there are provided mixtures of fusion constructs and combination compositions. In one embodiment, a mixture includes one or more fusion constructs and a pharmaceutically acceptable carrier or excipient. In another embodiment, a mixture includes one or more fusion constructs and an anti-cell proliferative, anti-tumor, anti-cancer, or anti-neoplastic treatment or agent. In a further embodiment, a mixture includes one or more fusion constructs and an immune enhancing agent. Combinations, such as one or more fusion constructs in a pharmaceutically acceptable carrier or excipient, with one or more of an anti-cell proliferative, anti-tumor, anti-cancer, or anti-neoplastic treatment or agent, and an immune enhancing treatment or agent, are also provided.

Fusion constructs of the invention, such as polypeptides having an amino acid sequence including a first lytic domain and a second binding moiety domain, can be used to target cells for lysis, cell death or apoptosis. Such cells can be selectively targeted. For example a cell that expresses a receptor, ligand, antigen or antibody can be targeted by a fusion construct and thereby be preferentially killed compared to cells that express less of the receptor, ligand, antigen or antibody.

In accordance with the invention, there are provided methods of reducing or inhibiting proliferation of a cell, and methods of reducing or inhibiting cell proliferation. In one embodiment, a method includes contacting a cell with a fusion construct in an amount sufficient to reduce or inhibit proliferation of the cell. In another embodiment, a method includes contacting a cell with a fusion construct in an amount sufficient to reduce or inhibit cell proliferation.

Also provided are methods of reducing or inhibiting proliferation of a hyperproliferative cell, and methods of reducing or inhibiting proliferation of hyperproliferating cells. In one embodiment, a method includes contacting a hyperproliferative cell or hyperproliferating cells with a fusion construct in an amount sufficient to reduce or inhibit proliferation.

Further provided are methods of reducing or inhibiting proliferation of a non-metastatic or metastatic neoplastic, cancer, tumor and malignant cell. In one embodiment, a method includes contacting a neoplastic, cancer, tumor or malignant cell with a fusion construct in an amount sufficient to reduce or inhibit proliferation of the cell.

Still further provided are methods of reducing or inhibiting proliferation of a dormant or non-dividing non-metastatic or metastatic neoplastic, cancer, tumor and malignant cell. In one embodiment, a method includes contacting a dormant or non-dividing neoplastic, cancer, tumor or malignant cell with a fusion construct in an amount sufficient to reduce or inhibit proliferation of the dormant or non-dividing cell.

Additionally provided are methods of selectively reducing or inhibiting proliferation of a cell (e.g., a hyperproliferating cell) that expresses a receptor, ligand, antibody or antigen. In one embodiment, a method includes contacting the cell with a fusion construct in an amount sufficient to reduce or inhibit proliferation of the cell (e.g., hyperproliferating cell), wherein the binding moiety of said peptide binds to the receptor, ligand, antibody or antigen expressed by the cell.

Yet additionally provided are methods of selectively reducing or inhibiting proliferation of a neoplastic, tumor, cancer or malignant cell that expresses a receptor, ligand, antibody or antigen. In one embodiment, a method includes contacting the cell with a fusion construct in an amount sufficient to reduce or inhibit proliferation of the neoplastic, tumor, cancer or malignant cell, wherein the binding moiety of said fusion construct binds to the receptor, ligand, antibody or antigen expressed by the cell.

The term "contacting" means direct or indirect binding or interaction between two or more entities (e.g., between a fusion construct and a cell). Contacting as used herein includes in solution, in solid phase, in vitro, ex vivo, in a cell and in vivo. Contacting in vivo can be referred to as administering, or administration.

Cells to target for reducing or inhibiting proliferation, non-selectively or selectively, include cells that express any molecule to which the binding moiety of the fusion construct binds. Exemplary cells include a cell that expresses a receptor (e.g., a hormone receptor, growth factor receptor, a cytokinic receptor, a chemokine receptor), ligand (e.g., a hormone, growth factor, cytokine, chemokine) or antibody or an antigen, or an integrin or integrin receptor (peptides containing "RGD" sequence motif), or a component present in extracellular matrix (ECM), such as mono-, di- or oligo-saccharides, sialic acid, galactose, mannose, fucose, acetylneuraminic acid, peptides containing "RGD" sequence motif, etc.

Target cells include cells that express a sex or gonadal steroid hormone or a sex or gonadal steroid hormone receptor. Target cells also include cells that express a receptor that binds to gonadotropin-releasing hormone I, gonadotropin-releasing hormone II, lamprey III luteinizing hormone releasing hormone, luteinizing hormone, chorionic gonadotropin, melanocyte stimulating hormone, estradiol, diethylstilbestrol, dopamine, somatostatin, follicle-stimulating hormone (FSH), glucocorticoid, estrogen, testosterone, adrostenedione, dihydrotestosterone, dehydroepiandrosterone, progesterone, androgen, epidermal growth factor (EGF), Her2/neu, vitamin H, folic acid or a derivative thereof (e.g., folate), transferrin, thyroid stimulating hormone (TSH), endothelin, bombesin, growth hormone, vasoactive intestinal peptide, lactoferrin, an integrin (e.g., alpha-5 beta 3 or alpha-5 beta 1 integrin), nerve growth factor, CD19, CD20, CD23, CD27, CD28, CD30, CD33, CD40, CD52, CD56, CD70, CD154, immunoglobulin-like receptors, ROR1, IGF-1, carcinoembryonic antigen (CEA), prostate specific antigen (PSA), prostate specific membrane antigen (PSMA), transforming growth factor alpha, transforming growth factor beta, insulin-like growth factor, vascular endothelial growth factor, insulin, ceruloplasmin, or HIV-tat.

Target cells further include cells that express a receptor that binds to a sex or gonadal steroid hormone or a sex or gonadal steroid hormone receptor. Target cells moreover include cells that express a receptor that binds to gonadotropin-releasing hormone I, gonadotropin-releasing hormone II, lamprey III luteinizing hormone releasing hormone, luteinizing hormone beta chain, luteinizing hormone, chorionic gonadotropin, chorionic gonadotropin beta subunit, melanocyte stimulating hormone, estradiol, diethylstilbestrol, dopamine, somatostatin, follicle-stimulating hormone (FSH), glucocorticoid, glucocorticoid, estrogen, testosterone, adrostenedione, dihydrotestosterone, dehydroepiandrosterone, progesterone, androgen, epidermal growth factor (EGF), Her2/neu, vitamin H, folic acid or a derivative thereof (e.g., folate), transferrin, thyroid stimulating hormone (TSH), endothelin, bombesin, growth hormone, vasoactive intestinal peptide, lactoferrin, an integrin (e.g., alpha-5 beta 3 or alpha-5 beta 1 integrin), nerve growth factor, CD19, CD20, CD23, CD27, CD28, CD30, CD33, CD40, CD52, CD56, CD70, CD154, immunoglobulin-like receptors, ROR1, IGF-1, carcinoembryonic antigen (CEA), prostate specific antigen (PSA), prostate specific membrane antigen (PSMA), transforming growth factor alpha, transforming growth factor beta, insulin, ceruloplasmin, HIV-tat, or an analogue thereof (e.g., mifepristone, flutamide, lupron, zxoladex, supprelin, synatel triptorelin, buserelin, centrorelix, ganirelix, abarelix, antide, teverelix or degarelix (Fe200486)).

Cells to target for reducing or inhibiting proliferation, non-selectively or selectively, additionally include cells that express "tumor associated antigens," such as carcinoembryonic antigen (CEA), alpha-fetoprotein (AFP), prostate specific antigen (PSA), prostate specific membrane antigen (PSMA), CA 125 (residual epithelial ovarian cancer), soluble Interleukin-2 (IL-2) receptor, RAGE-1, tyrosinase, MAGE-1, MAGE-2, NY-ESO-1, Melan-A/MART-1, glycoprotein (gp) 75, gp100, beta-catenin, PRAME, MUM-1, ZFP161, Ubiquilin-1, HOX-B6, YB-1, Osteonectin, and ILF3. Cells to target for reducing or inhibiting proliferation, non-selectively or selectively, yet additionally include cells that express transferrin, folic acid and derivatives thereof (e.g., folate), and a tumor necrosis factor (TNF) family member or, such as TNF-alpha, TNF-beta (lymphotoxin, LT), TRAIL, Fas, LIGHT, and 41BB, and receptors therefore.

Fusion constructs and methods of the invention are also applicable to treating undesirable or aberrant cell proliferation and hyperproliferative disorders. Thus, in accordance with the invention, methods of treating undesirable or aberrant cell proliferation and hyperproliferative disorders are provided. In one embodiment, a method includes administering to a subject (in need of treatment) an amount of a fusion construct sufficient to treat the undesirable or aberrant cell proliferation or the hyperproliferative disorder.

The term "hyperproliferative disorder" refers to any undesirable or aberrant cell survival (e.g., failure to undergo programmed cell death or apoptosis), growth or proliferation. Such disorders include benign hyperplasias, non-metastatic and metastatic neoplasias, cancers, tumors and malignancies. Undesirable or aberrant cell proliferation and hyperproliferative disorders can affect any cell, tissue, organ in a subject. Undesirable or aberrant cell proliferation and hyperproliferative disorders can be present in a subject, locally, regionally or systemically. A hyperproliferative disorder can arise from a multitude of tissues and organs, including but not limited to breast, lung (e.g., small cell or non-small cell), thyroid, head and neck, brain, nasopharynx, throat, nose or sinuses, lymphoid, adrenal gland, pituitary gland, thyroid, lymph, gastrointestinal (mouth, esophagus, stomach, duodenum, ileum, jejunum (small intestine), colon, rectum), genito-urinary tract (uterus, ovary, vagina cervix, endometrium, fallopian tube, bladder, testicle, penis, prostate), kidney, pancreas, liver, bone, bone marrow, lymph, blood, muscle, skin, and stem cells, which may or may not metastasize to other secondary sites, regions or locations.

Fusion constructs and methods of the invention are also applicable to metastatic or non-metastatic tumor, cancer, malignancy or neoplasia of any cell, organ or tissue origin. Such disorders can affect virtually any cell or tissue type, e.g., carcinoma, sarcoma, melanoma, neural, and reticuloendothelial or haematopoietic neoplastic disorders (e.g., myeloma, lymphoma or leukemia).

As used herein, the terms "neoplasia" and "tumor" refer to a cell or population of cells whose growth, proliferation or survival is greater than growth, proliferation or survival of a normal counterpart cell, e.g. a cell proliferative or differentiative disorder. A tumor is a neoplasia that has formed a distinct mass or growth. A "cancer" or "malignancy" refers to a neoplasia or tumor that can invade adjacent spaces, tissues or organs. A "metastasis" refers to a neoplasia, tumor, cancer or malignancy that has disseminated or spread from its primary site to one or more secondary sites, locations or regions within the subject, in which the sites, locations or regions are distinct from the primary tumor or cancer.

Neoplastic, tumor, cancer and malignant cells (metastatic or non-metastatic) include dormant or residual neoplastic, tumor, cancer and malignant cells. Such cells typically consist of remnant tumor cells that are not dividing (G0-G1 arrest). These cells can persist in a primary site or as disseminated neoplastic, tumor, cancer or malignant cells as a minimal residual disease. These dormant neoplastic, tumor, cancer or malignant cells remain unsymptomatic, but can develop severe symptoms and death once these dormant cells proliferate. Invention methods can be used to reduce or inhibit proliferation of dormant neoplastic, tumor, cancer or malignant cells, which can in turn inhibit or reduce tumor or cancer relapse, or tumor or cancer metastasis or progression.

In accordance with the invention, methods of treating a subject having a metastatic or non-metastatic tumor, cancer, malignancy or neoplasia are provided. In one embodiment, a method includes administering to a subject (in need of treatment) an amount of a fusion construct of sufficient to treat (e.g., reduce or inhibit proliferation) the metastatic or non-metastatic tumor, cancer, malignancy or neoplasia.

The metastatic or non-metastatic tumor, cancer, malignancy or neoplasia may be in any stage, e.g., early or advanced, such as a stage I, II, III, IV or V tumor. The metastatic or non-metastatic tumor, cancer, malignancy or neoplasia may have been subject to a prior treatment or be stabilized (non-progressing) or in remission.

In terms of metastasis, invention methods can be used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression. Thus, methods of the invention include, among other things, 1) reducing or inhibiting growth, proliferation, mobility or invasiveness of tumor or cancer cells that potentially or do develop metastases (e.g., disseminated tumor cells, DTC); 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established; and 4) reducing or inhibiting formation or establishment of additional metastasis after the metastasis has been formed or established.

Cells of a metastatic or non-metastatic tumor, cancer, malignancy or neoplasia may be aggregated in a "solid" cell mass or be dispersed or diffused. A "solid" tumor refers to cancer, neoplasia or metastasis that typically aggregates together and forms a mass. Specific non-limiting examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterus, cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma and oligodendrocytoma.

A "liquid tumor," which refers to neoplasia that is dispersed or is diffuse in nature, as they do not typically form a solid mass. Particular examples include neoplasia of the reticuloendothelial or hematopoietic system, such as lymphomas, myelomas and leukemias. Non-limiting examples of leukemias include acute and chronic lymphoblastic, myeloblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As disclosed herein, undesirable or aberrant cell proliferation or hyperproliferative disorders can occur in uterus, breast, vagina, cervix and fallopian tube. Endometriosis occurs when cells of the uterus grow outside of the uterus and into other areas, such as ovaries, bladder or bowel. Fibroids and polyps can affect uterus, breast, vagina, cervix and fallopian tube.

Thus, in accordance with the invention, there are provided methods of treating endometriosis and fibroids or polyps. In one embodiment, a method includes administering to a subject an amount of a fusion construct sufficient to treat endometriosis. In another embodiment, a method includes administering to a subject an amount of a fusion construct sufficient to treat a fibroid or polyp.

Target cells include cells that participate in or a required for reproduction or fertility. Thus, in accordance with the invention, there are provided methods of reducing fertility of an animal. In one embodiment, a method includes administering to a subject an amount of a fusion construct sufficient to reduce fertility or reduce the likelihood of pregnancy or reducing sperm production in a male mammal.

As also disclosed herein, undesirable or aberrant cell proliferation or hyperproliferative disorders can occur in prostate. Thus, in accordance with the invention, there are provided methods of treating benign prostate hyperplasia or metastatic prostate neoplasia. In one embodiment, a method includes administering to a subject an amount of a fusion construct sufficient to treat benign prostate hyperplasia or metastatic prostate neoplasia.

Any composition, treatment, protocol, therapy or regimen having an anti-cell proliferative activity or effect can be combined with a fusion construct or used in combination in a method of the invention. Fusion constructs and methods of the invention therefore include anti-proliferative, anti-tumor, anti-cancer, anti-neoplastic and anti-metastatic treatments, protocols and therapies, which include any other composition, treatment, protocol or therapeutic regimen that inhibits, decreases, retards, slows, reduces or prevents a hyperproliferative disorder, such as tumor, cancer, malignant or neoplastic growth, progression, metastasis, proliferation or survival, or worsening in vitro or in vivo. Particular non-limiting examples of an anti-proliferative (e.g., tumor) therapy include chemotherapy, immunotherapy, radiotherapy (ionizing or chemical), local thermal (hyperthermia) therapy, surgical resection and vaccination. A fusion construct can be administered prior to, substantially contemporaneously with or following administration of the anti-cell proliferative, anti-neoplastic, anti-tumor, anti-cancer, anti-metastatic or immune-enhancing treatment or therapy. A fusion construct can be administered as a combination compositions with the anti-cell proliferative, anti-neoplastic, anti-tumor, anti-cancer, anti-metastatic or immune-enhancing treatment or therapy, metastatic or non-metastatic tumor, cancer, malignancy or neoplasia.

Anti-proliferative, anti-neoplastic, anti-tumor, anti-cancer and anti-metastatic compositions, therapies, protocols or treatments include those that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative, anti-neoplastic, anti-tumor, anti-cancer and anti-metastatic activities include alkylating agents, antimetabolites, plant extracts, plant alkaloids, nitrosoureas, hormones, nucleoside and nucleotide analogues. Specific examples of drugs having anti-cell proliferative, anti-neoplastic, anti-tumor, anti-cancer and anti-metastatic activities include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2'deoxycytidine), cytarabine, 1-beta-D-arabinofuranosyl-5-azacytosine and dihydro-5-azacytidine, bleomycin, actinomycin D, mithramycin, mitomycin C, carmustine, lomustine, semustine, streptozotocin, hydroxyurea, cisplatin, mitotane, procarbazine, dacarbazine, taxol, vinblastine, vincristine, doxorubicin and dibromomannitol etc.

Additional agents that are applicable with fusion constructs and methods are known in the art and can be employed. For example, biologicals such as antibodies, cell growth factors, cell survival factors, cell differentiative factors, cytokines and chemokines can be administered. Non-limiting examples of monoclonal antibodies include rituximab (Rituxan®), trastuzumab (Herceptin), bevacizumab (Avastin), cetuximab (Erbitux), alemtuzumab (Campath), panitumumab (Vectibix), ibritumomab tiuxetan (Zevalin), tositumomab (Bexxar) etc. which can be used in combination with, inter alia, a fusion construct in accordance with the invention. Other targeted drugs that are applicable for use with the fusion constructs are imatinib (Gleevec), gefitinib (Iressa), bortzomib (Velcade), lapatinib (Tykerb), sunitinib (Sutent), sorafenib (Nevaxar), nilotinib (Tasigna) etc Non-limiting examples of cell growth factors, cell survival factors, cell differentiative factors, cytokines and chemokines include L-2, IL-1α, IL-1β, IL-3, L-6, L-7, granulocyte-macrophage-colony stimulating factor (GMCSF), IN-γ, IL-12, TNF-α, TNFβ, MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAPIIIβ-TG/NAP-2, Mig, PBSF/SDF-1 and lymphotactin.

Additional non-limiting examples include immune-enhancing treatments and therapies, which include cell based therapies. In particular, immune-enhancing treatments and therapies include administering lymphocytes, plasma cells, macrophages, dendritic cells, NK cells and B-cells.

Methods of treating a metastatic or non-metastatic tumor, cancer, malignancy or neoplasia, methods of treating a subject in need of treatment due to having or at risk of having a metastatic or non-metastatic tumor, cancer, malignancy or neoplasia, and methods of increasing effectiveness or improving an anti-proliferative, anti-tumor, anti-cancer, anti-neoplasia or anti-malignancy, therapy are provided. In respective embodiments, a method includes administering to a subject with or at risk of a metastatic or non-metastatic tumor, cancer, malignancy or neoplasia, an amount of a fusion construct sufficient to treat the metastatic or non-metastatic tumor, cancer, malignancy or neoplasia; administering to the subject an amount of a fusion construct sufficient to treat the subject; and administering to a subject that is undergoing or has undergone metastatic or non-metastatic tumor, cancer, malignancy or neoplasia therapy, an amount of a fusion construct sufficient to increase effectiveness of the anti-proliferative, anti-tumor, anti-cancer, anti-neoplasia or anti-malignancy therapy.

Methods of the invention may be practiced prior to (i.e. prophylaxis), concurrently with or after evidence of the presence of undesirable or aberrant cell proliferation or a hyperproliferative disorder, disease or condition begins (e.g., one or more symptoms). Administering a fusion construct prior to, concurrently with or immediately following development of a symptom of undesirable or aberrant cell proliferation or a hyperproliferative disorder may decrease the occurrence, frequency, severity, progression, or duration of one or more symptoms of the undesirable or aberrant cell proliferation or a hyperproliferative disorder, disease or condition in the subject. In addition, administering a fusion construct prior to, concurrently with or immediately following development of one or more symptoms of the undesirable or aberrant cell proliferation or a hyperproliferative disorder, disease or condition may inhibit, decrease or prevent the spread or dissemination of hyperproliferating cells (e.g., metastasis) to other sites, regions, tissues or organs in a subject, or establishment of hyperproliferating cells (e.g., metastasis) at other sites, regions, tissues or organs in a subject.

Fusion constructs and the methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. Fusion constructs and methods of the invention therefore include providing a therapeutic benefit or improvement to a subject.

In a method of the invention in which a therapeutic benefit or improvement is a desired outcome, a fusion construct of the invention can be administered in a sufficient or effective amount to a subject in need thereof. An "amount sufficient" or "amount effective" refers to an amount that provides, in single or multiple doses, alone or in combination, with one or more other compositions (therapeutic agents such as a chemotherapeutic or immune stimulating drug), treatments, protocols, or therapeutic regimens agents, a detectable response of any duration of time (long or short term), a desired outcome in or a benefit to a subject of any measurable or detectable degree or for any duration of time (e.g., for hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is considered a satisfactory outcome.

The term "ameliorate" means a detectable objective or subjective improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatment can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods affecting one or more underlying causes of the condition, disorder, disease or symptom are therefore considered to be beneficial. Stabilizing or inhibiting progression or worsening of a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

In particular embodiments, a method of treatment results in partial or complete destruction of a metastatic or non-metastatic tumor, cancer, malignant or neoplastic cell mass, volume, size or numbers of cells; results in stimulating, inducing or increasing metastatic or non-metastatic tumor, cancer, malignant or neoplastic cell necrosis, lysis or apoptosis; results in reducing metastatic or non-metastatic tumor, cancer, malignant or neoplastic volume, size, cell mass; results in inhibiting or preventing progression or an increase in metastatic or non-metastatic tumor, cancer, malignant or neoplastic volume, mass, size or cell numbers; results in inhibiting or decreasing the spread or dissemination of hyperproliferating cells (e.g., metastasis) to other (secondary) sites, regions, tissues or organs in a subject, or establishment of hyperproliferating cells (e.g., metastasis) at other (secondary) sites, regions, tissues or organs in a subject; or results in prolonging lifespan of the subject. In additional particular embodiments, a method of treatment results in reducing or decreasing severity, duration or frequency of an adverse symptom or complication associated with or caused by the metastatic or non-metastatic tumor, cancer, malignancy or neoplasia.

An amount sufficient or an amount effective can but need not be provided in a single administration and, can but need not be, administered alone or in combination with another composition (e.g., chemotherapeutic or immune enhancing or stimulating agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., chemotherapeutic or immune stimulating agent), treatment, protocol or therapeutic regimen, since additional doses, amounts or duration above and beyond such doses, or additional compositions (e.g., chemotherapeutic or immune stimulating agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, nor a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a particular subject, not a group or the general population. Such amounts will depend in part upon the condition treated, such as the type or stage of undesirable or aberrant cell proliferation or hyperproliferative disorder (e.g., a metastatic or non-metastatic tumor, cancer, malignancy or neoplasia), the therapeutic effect desired, as well as the individual subject (e.g., the bioavailability within the subject, gender, age, etc.).

Particular non-limiting examples of therapeutic benefit or improvement for undesirable or aberrant cell proliferation, such as a hyperproliferative disorder (e.g., a metastatic or non-metastatic tumor, cancer, malignancy or neoplasia) include a reduction in cell size, mass or volume, inhibiting an increase in cell size, mass or volume, a slowing or inhibition of worsening or progression, stimulating cell necrosis, lysis or apoptosis, reducing or inhibiting neoplastic or tumor malignancy or metastasis, reducing mortality, and prolonging lifespan of a subject. Thus, inhibiting or delaying an increase in cell size, mass, volume or metastasis (stabilization) can increase lifespan (reduce mortality) even if only for a few days, weeks or months, even though complete ablation of the metastatic or non-metastatic tumor, cancer, malignancy or neoplasia has not occurred. Adverse symptoms and complications associated with a hyperproliferative disorder (e.g., a metastatic or non-metastatic tumor, cancer, malignancy or neoplasia) that can be reduced or decreased include, for example, pain, nausea, discomfort, lack of appetite, lethargy and weakness. A reduction in the occurrence, frequency, severity, progression, or duration of a symptom of undesirable or aberrant cell proliferation, such as a hyperproliferative disorder (e.g., a metastatic or non-metastatic tumor, cancer, malignancy or neoplasia), such as an improvement in subjective feeling (e.g., increased energy, appetite, reduced nausea, improved mobility or psychological well being, etc.), are therefore all examples of therapeutic benefit or improvement.

For example, a sufficient or effective amount of a fusion construct is considered as having a therapeutic effect if administration results in less chemotherapeutic drug, radiation or immunotherapy being required for treatment of undesirable or aberrant cell proliferation, such as a hyperproliferative disorder (e.g., a metastatic or non-metastatic tumor, cancer, malignancy or neoplasia).

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of undesirable or aberrant cell proliferation, such as a hyperproliferative disorder (e.g., a metastatic or non-metastatic tumor, cancer, malignancy or neoplasia) for analysis of fusion constructs in vivo.

Subjects appropriate for treatment include those having or at risk of having a metastatic or non-metastatic tumor, cancer, malignant or neoplastic cell, those undergoing as well as those who are undergoing or have undergone anti-proliferative (e.g., metastatic or non-metastatic tumor, cancer, malignancy or neoplasia) therapy, including subjects where the tumor is in remission. "At risk" subjects typically have risk factors associated with undesirable or aberrant cell proliferation, development of hyperplasia (e.g., a tumor).

Particular examples of at risk or candidate subjects include those with cells that express a receptor, ligand, antigen or antibody to which a fusion construct can bind, particularly where cells targeted for necrosis, lysis, killing or destruction express greater numbers or amounts of receptor, ligand, antigen or antibody than non-target cells. Such cells can be selectively or preferentially targeted for necrosis, lysis or killing.

At risk subjects also include those that are candidates for and those that have undergone surgical resection, chemotherapy, immunotherapy, ionizing or chemical radiotherapy, local or regional thermal (hyperthermia) therapy, or vaccination. The invention is therefore applicable to treating a subject who is at risk of a metastatic or non-metastatic tumor, cancer, malignancy or neoplasia or a complication associated with a metastatic or non-metastatic tumor, cancer, malignancy or neoplasia, for example, due to metastatic or non-metastatic tumor, cancer, malignancy or neoplasia reappearance or regrowth following a period of stability or remission.

Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brca1, for example. Subjects at risk for developing colon cancer have early age or high frequency polyp formation, or deleted or mutated tumor suppressor genes, such as adenomatous polyposis coli (APC), for example.

Subjects also include those precluded from other treatments. For example, certain subjects may not be good candidates for surgical resection, chemotherapy, immunotherapy, ionizing or chemical radiotherapy, local or regional thermal (hyperthermia) therapy, or vaccination. Thus, candidate subjects for treatment in accordance with the invention include those that are not a candidate for surgical resection, chemotherapy, immunotherapy, ionizing or chemical radiotherapy, local or regional thermal (hyperthermia) therapy, or vaccination.

Fusion constructs may be formulated in a unit dose or unit dosage form. In a particular embodiment, a fusion construct is in an amount effective to treat a subject having undesirable or aberrant cell proliferation or a hyperproliferative disorder. In an additional particular embodiment, a fusion construct is in an amount effective to treat a subject having a metastatic or non-metastatic tumor, cancer, malignancy or neoplasia. In a further particular embodiment, a fusion construct is in an amount effective to reduce fertility of a subject. Exemplary unit doses range from about 25-250, 250-500, 500-1000, 1000-2500 or 2500-5000, 5000-25,000, 5000-50,000 ng; and from about 25-250, 250-500, 500-1000, 1000-2500 or 2500-5000, 5000-25,000, 5000-50,000 µg.

Compositions and methods of the invention may be contacted or provided in vitro, ex vivo or in vivo. Compositions can be administered to provide the intended effect as a single or multiple dosages, for example, in an effective or sufficient amount. Exemplary doses range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 µg/kg, on consecutive days, or alternating days or intermittently. Single or multiple doses can be administered on consecutive days, alternating days or intermittently.

Compositions can be administered and methods may be practiced via systemic, regional or local administration, by any route. For example, a fusion construct can be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro)encapsulated delivery system or packaged into an implant for administration.

The invention further provides fusion constructs and methods wherein the fusion constructs are included in pharmaceutical compositions. A pharmaceutical composition refers to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

Additional pharmaceutical formulations and delivery systems are known in the art and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

The invention provides kits including fusion constructs of the invention, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for reducing or inhibiting proliferation of a cell, reducing or inhibiting proliferation of undesirable or aberrant cells, such as a hyperproliferating cell, reducing or inhibiting proliferation of a metastatic or non-metastatic tumor, cancer, malignant or neoplastic cell, treating a subject having a hyperproliferative disorder, treating a subject having a metastatic or non-metastatic tumor, cancer, malignancy or neoplasia, or reducing fertility of an animal.

A kit can contain a collection of such components, e.g., two or more fusion constructs alone, or in combination with another therapeutically useful composition (e.g., an anti-proliferative or immune-enhancing drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant cell proliferation, hyperproliferating cells and disorders (e.g., metastatic or non-metastatic tumor, cancer, malignancy or neoplasia). Kits of the invention therefore can additionally include labels or instructions for practicing any of the methods of the invention described herein including treatment methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain host cells expressing fusion constructs of the invention, or that contain nucleic acids encoding fusion constructs. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a fusion construct" or a "lytic domain" includes a plurality of such fusion constructs or lytic domains, and so forth.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

Initial studies included in vitro screening of 28 lytic domain peptides that contained different hinge sequences between lytic peptide moiety and ligands; that contained 30% of D amino acids (D-enantiomers), that were 18 and 15 amino acids in length for the lytic peptide moiety and contained hinge sequence or their D-enantiomers. The introduction of α-aminocaproic acid as a spacer on 21, 18 and 15 amino acid Phor21 analogs was studied. The ligands chosen for study included βCG-ala, a 15 amino acid fragment of the binding moiety of the beta chain from chorionic gonadotropin, and LHRH, a decapeptide that represents a full functioning ligand.

Example 2

This example describes screening for cell toxicity ($IC_{50}$) and hemolytic activity using a human breast cancer cell line.

Eighteen βCG-ala and eight LHRH conjugated fusion constructs were studied and compared to Phor21-βCG-ala and unconjugated Phor21 and Phor18 (338913)=CLIP71 peptides. The human breast cancer cell line MDA-MB-435S.luc, which over expresses chorionic gonadotrophin (CG) and luteinizing hormone-releasing hormone (LHRH) receptors, was used to screen at passage numbers 248-252. The MDA-MB-435S.luc cell line was constructed from the MDA-MB-435S cell line obtained from the American Type Cell Culture Collection by stable transfection with the plasmid PRC/CMV-luc containing the *Photinus pyralis* luciferase gene and an antibody resistance gene by lipofection. The stably transfected cell line was selected using G418 and the clones with the highest expression for the luciferase gene were tested for their LH and LHRH receptor expression.

MDA-MB435S.luc cells were grown in Leibovitz's L 15 medium, 10% fetal bovine serum, 0.01 mg/ml bovine insulin, 100 IU/ml penicillin, 100 microg/ml streptomycin. The cells were cultured in tight closed flasks. The incubations were conducted using 96 well plates at 10,000 cells per well. Cells were typically seeded into 96 well plates and media was replaced after 48 hours of incubation. Each assay was conducted at increasing concentrations of 0, 0.001, 0.01, 0.05, 0.1, 0.5, 1, 2, 5, 10 and 100 micromolar doses of lytic peptide-binding domain conjugate. Each lytic peptide-binding domain conjugate provided in lyophilized form and was freshly dissolved in saline and added to cells. The duration of incubation was typically 24 h, and cell viability assays were conducted using formazan conversion assays (MTT assay). Controls contained saline or 0.1% triton as reference for 0 and 100% cell death, respectively.

Data were processed and analyzed using Graph Pad Prizm 4™ software (Graph Pad Prizm, Inc). Statistical analysis for significance was determined by a two-tailed Student's T-test. Each study was conducted to achieve an N of at least 8.

The effect of increasing the length of the fusion construct was ascertained (Javadpour et al., *J Med Chem* 39:3107 (1996); Javadpour and Barkeley, *Biochemistry* 36:9540 (1997); Leuschner and Hansel, *Current Pharmaceutical Design*, 10:2299 (2004); and Leuschner and Hansel, *Biol Reprod* 73:255 (2005)). Lytic peptides conjugated at the C-terminus to βCG-ala showed increasing toxicity with increasing length of the construct. The $IC_{50}$ for peptides of various lengths were: 14 amino acids (Phor 14) 5.74, 15 amino acids (Phor15) 1.92, 18 amino acids (Phor18=CLIP71) 1.09, 21 amino acids (Phor21) 2.31 and 28 amino acids (Phor28) 1.36 μM (Table 3).

The effect of the position of the binding moiety (N- or C-terminus) was ascertained. In brief, Phor21-βCG-ala (C-terminus), βCG-ala Phor21 (N-terminus), LHRH-Phor21 (N-terminus) and Phor21-LHRH(C-terminus) fusion constructs were studied. The $IC_{50}$ of the peptides were: Phor21-βCG-ala 2.3 μM, for βCG-ala-Phor21 4.7 μM, for LHRH-Phor21 2.65 μM, and for Phor21-LHRH 1.71 μM. The data demonstrate that C-terminal positioning of βCG-ala and LHRH binding moieties showed greater toxicity than if the binding moiety was positioned at the N-terminus.

LHRH-receptor is present in many human cancers (see Table 1). The activity of LHRH as the binding moiety was compared to βCG-ala as the binding moiety.

Figure 1:
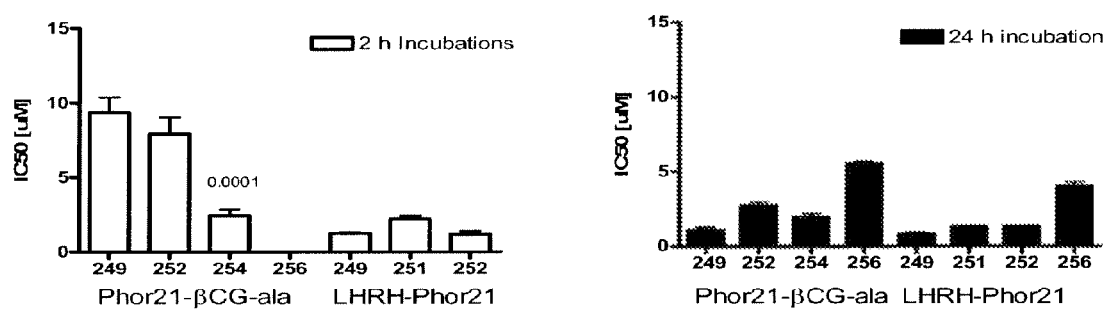
FIG. 1 shows that LHRH-Phor21 kills cancer cells faster than Phor21-βCG-ala. Human breast cancer cells (MDA-MB435 S.luc, various passage numbers) were incubated with Phor21-βCG-ala or LHRH-Phor21.

Toxicities of LHRH-Phor21 and Phor21-βCG-ala were compared in human MDA-MB435S.luc breast cancer cells in vitro, at 2 or 24 hour incubation. The data indicate that LHRH-Phor21 killed cells faster than Phor21-βCG-ala, LHRH-Phor21 eliciting cell killing within 2 hours (FIG. 1).

TABLE 1

LH and LHRH Receptors in Human Cancers

| Cancer Type | LH Receptors | LHRH-Receptors |
|---|---|---|
| Breast | 72% | 52% |
| Prostate | 100% | 86% |
| Ovarian | 40% | 80% |
| Endometrial | 17% | 80% |
| Pancreatic | N.D. | 68% |
| Lung | Yes | N.D. |
| Melanoma | 68% | Yes |
| Brain | N.D. | Yes |
| Colon | N.D. | Yes |
| Oral | N.D. | Yes |

Figure 2:
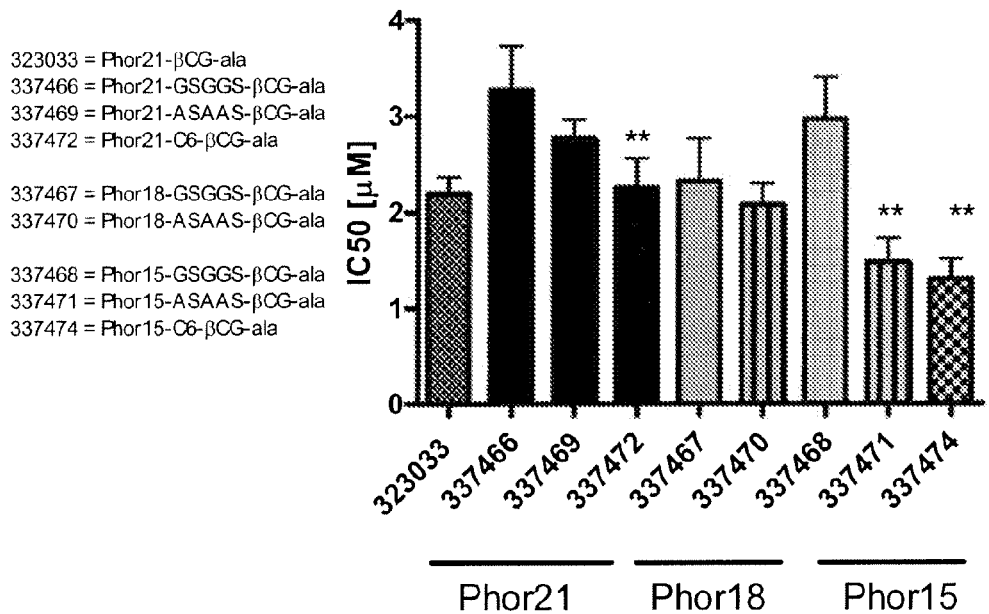
FIG. 2 shows cytotoxicity to MDA-MB-435S.luc cell (micromolar $IC_{50}$) of βCG-ala fusion constructs having 21 (Phor21), 18 (Phor18 (338983)=CLIP71) and 15 (Phor15) amino acids in their lytic domain, compared to Phor21-βCG-ala.

Introduction of hinge, spacer or linker sequences between the lytic domain and binding moiety resulted in peptides with greater potency than Phor21-βCG-ala in cell killing. (FIG. 2, Table 2). Whereas introduction of hinge sequences or spacers in the Phor21-βCG-ala fusion construct did not change cell killing activity significantly, the effect of ASAAS(SEQ. ID NO. 11) as a hinge sequence significantly increased the toxicity of lytic peptides with 15 amino acids for the βCG-conjugate; this effect was absent in the case of the βCG and LHRH conjugated peptide Phor18-LHRH and Phor18-ASAAS(SEQ. ID NO. 11)-LHRH, which were equally effective in vitro (Table 2, FIG. 4). A similar effect was observed when the hinge sequence was substituted by a 6 carbon spacer, alpha amino caproic acid (Table 2). The substitution of alanine by glycine in the second hinge sequence (GSGGS) (SEQ. ID NO. 10) resulted in significantly lower activity, suggesting that glycine may have had a helix destabilizing effect. (FIG. 2, Table 2).

TABLE 2

Effect of peptide length of βCG-ala conjugated peptides

| Peptide | None [$IC_{50}$ μM] | GSGGS [$IC_{50}$ μM] | ASAAS [$IC_{50}$ μM] | Amino-caproic acid [$IC_{50}$ μM] |
|---|---|---|---|---|
| Phor21 | 2.3 | 3.27 | 2.77 | 2.75 |
| Phor18 | 1.09* | 2.32 | 2.07 | NA |
| Phor15 | 1.92 | 2.96 | 1.48* | 1.34* |
| Phor14 | 6.72 | NA | NA | NA |
| LHRH-conjugated peptides | | | | |
| Phor21 | 1.31 | | NA | |
| Phor18 | 0.87 | | 0.89 | |

To ascertain the effect of D-amino acid substitutions, a fusion construct Phor21-βCG-ala synthesized as D enantiomer (hereinafter referred to as D-ala-Phor21-βCG-ala). This fusion construct showed comparable toxicity to MDA-MB-435S.luc breast cancer cells in vitro (Phor21-βCG-ala 2.31 μM, D-ala-Phor21-βCG-ala 2.15 μM (Table 3); D-ala-Phor18-βCG-ala was 1.4 fold more potent than Phor21-βCG-ala ($IC_{50}$ 1.6 μM), the LHRH counterpart was significantly more potent as D-enantiomer (Phor21-LHRH ($IC_{50}$ of 1.31 μM) compared to D-ala-Phor21-LHRH with $IC_{50}$ of 0.75 μM, D-Phor18-LHRH with $IC_{50}$ of 1.42 μM and Phor18-Lupron with $IC_{50}$ of 1.95 μM.

Figure 3:
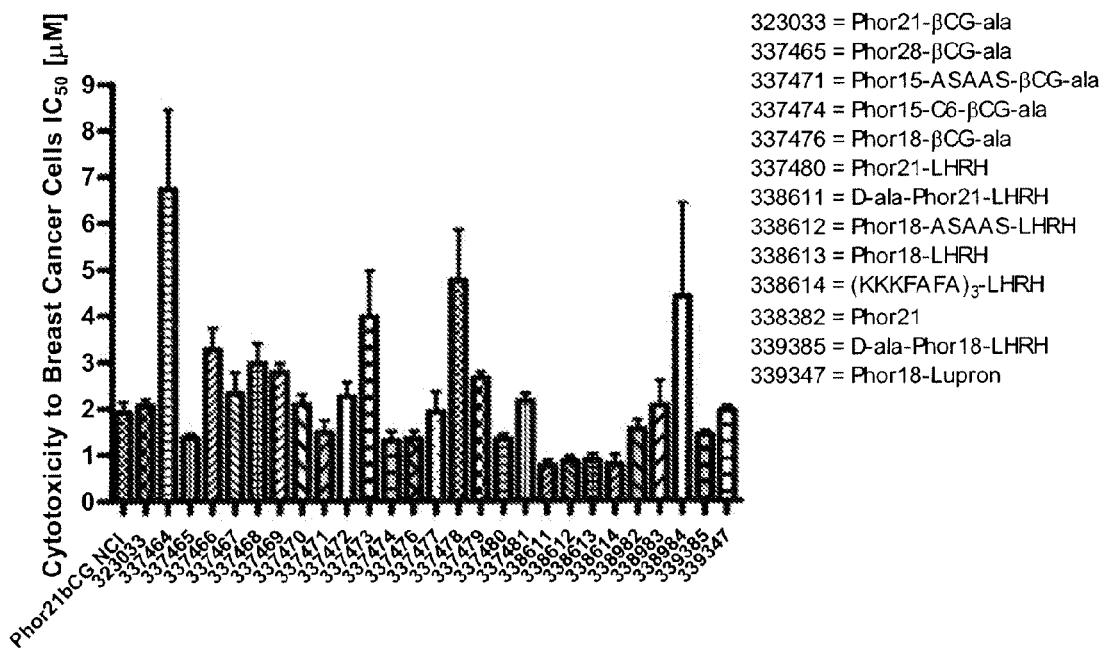
FIG. 3 shows cytotoxicity to MDA-MB-435S.luc cells (micromolar $IC_{50}$) of βCG-ala and LHRH fusion constructs.

The $IC_{50}$-values for βCG-ala and LHRH-conjugated lytic peptides in MDA-MB435S.luc breast cancer cells are summarized in Table 3 and FIG. 3. In brief, peptides with significantly lower $IC_{50}$ than Phor21-βCG-ala (2.31±0.16) were: Phor28-βCG-ala (1.36±0.09 μM; p<0.0001), Phor15-ASAAS(SEQ. ID NO. 11)-βCG-ala (1.48±0.24 μM; p<0.005), Phor15-$C_6$-βCG-ala (1.31±0.17 μM; p<0.004) ($C_6$=6 aminocaproic acid), Phor18-βCG-ala (1.09±0.17 μM; p<0.0001), Phor21-LHRH (1.31±0.1 μM; p<0.0001), D-ala-Phor21-LHRH (0.75±0.1 μM; p<0.0001), Phor18-ASAAS (SEQ. ID NO. 11)-LHRH (0.88±0.12 μM; p<0.0001), Phor18-LHRH (0.87±0.11 μM; p<0.0001), (KKKFAFA)$_3$ (SEQ. ID NO. 16)-LHRH (0.78±0.21 μM; p<0.0004), and D-ala-Phor18-LHRH (1.42±0.08 μM; p<0.004).

LHRH fusion constructs were in general more potent (more toxic and faster acting, FIG. 1) than βCG-ala fusion constructs. In brief, Phor21-LHRH, D-ala-Phor21-LHRH, Phor18-ASAAS(SEQ. ID NO. 11)-LHRH, Phor18-LHRH and peptide control 338614 ((KKKFAFA)$_3$ (SEQ. ID NO. 16)=inactive peptide) were significantly more toxic to human breast cancer cells compared to Phor21-βCG-ala (p<0.003). All LHRH fusion constructs were about equally effective, except for LHRH-Phor21 which was significantly less potent when the binding moiety was positioned at the C terminus relative to the lytic portion. D-ala-Phor18-LHRH was equally effective compared to Phor21-LHRH; Phor18-Lupron were less toxic, but comparable to Phor21-βCG-ala. (FIG. 4, Table 3; Lupron is QHWSY(D-Leu)LRPNEt).

Fusion constructs with significantly lower $IC_{50}$—values than Phor21-LHRH (1.34±0.1 μM) were: D-ala-Phor21-LHRH (0.75±0.12 μM; p<0.002), Phor18-ASAAS(SEQ. ID NO. 11)-LHRH (0.88±0.11 μM; p<0.0001), Phor18-LHRH (0.87±0.12 μM; p<0.004), and (KKKFAFA)$_3$-LHRH (0.78±0.21 μM; p<0.04). When the same fusion constructs were compared between βCG-ala and LHRH binding moieties, in all cases LHRH fusion constructs were significantly more toxic compared to their βCG-ala counterparts.

TABLE 3

Cytolytic peptides and peptide conjugates - summary of $IC_{50}$ and $HA_{50}$ characteristics in MDA-MB-435S luc cells

| Peptide ID | Description | Peptide content [%] | $IC_{50}$ [μM] | $HA_{50}$ [μM] | $IC_{50}/HA_{50}$ |
|---|---|---|---|---|---|
| 337464 | Phor14-βCG-ala | 84.9 | 6.74 ± 1.7*** | 1203 ± 586 | 0.005 |
| 323033 | Phor21-βCG-ala | 85.3 | 2.31 ± 0.16 | 73.44 ± 6.9 | 0.03 |
| 337465 | Phor28-βCG-ala | 85.1 | 1.36 ± 0.09*** | | |
| 337466 | Phor21-GSGGS-βCG-ala | 84.6 | 3.27 ± 0.45 | 153.6 ± 25 | 0.02 |
| 337467 | Phor18-GSGGS-βCG-ala | 87.6 | 2.32 ± 0.44 | 723.6 ± 219 | 0.003 |
| 337468 | Phor15-GSGGS-βCG-ala | 85.7 | 2.96 ± 0.43 | | |
| 337469 | Phor21-ASAAS-βCG-ala | 83.5 | 2.77 ± 0.18 | 72 ± 8.9 | 0.037 |
| 337470 | Phor18-ASAAS-βCG-ala | 86.6 | 2.07 ± 0.2 | 578 ± 241 | 0.0036 |
| 337471 | Phor15-ASAAS-βCG-ala | 86.2 | 1.48 ± 0.24** | 421 ± 110 | 0.0035 |
| 337472 | Phor21-$C_6$-βCG-ala | 85 | 2.25 ± 0.3 | | |
| 337473 | Phor18-$C_6$-βCG-ala | 84.3 | 3.9 ± 0.9 | | |
| 337474 | Phor15-$C_6$-βCG-ala | 87.5 | 1.31 ± 0.17*** | Not lytic | 0 |
| 323033 | Phor21-βCG-ala | 85.3 | 2.31 ± 0.16 | | |
| 337476 | Phor18-βCG-ala | 84.1 | 1.09 ± 0.17*** | 169.8 ± 24 | 0.006 |
| 337477 | Phor15-βCG-ala | 85.9 | 1.92 ± 0.43 | | |
| 337478 | βCG-ala-Phor21 | 84 | 4.75 ± 1.1 | | |
| 337479 | LHRH-Phor21 | 87.3 | 2.65 ± 0.12 | 33 ± 3.6 | 0.08 |
| 337480 | Phor21-LHRH | 82.4 | 1.31 ± 0.1*** | 25 ± 4.3 | 0.07 |
| 337481 | (D Ala)-Phor21-βCG-ala | 82.7 | 2.15 ± 0.26 | Not lytic | 0 |
| 338982 | Phor21 | 77.9 | 1.5 ± 0.2 N = 8 | Not lytic | 0 |

TABLE 3-continued

Cytolytic peptides and peptide conjugates - summary of
$IC_{50}$ and $HA_{50}$ characteristics in MDA-MB-435S luc cells

| Peptide ID | Description | Peptide content [%] | $IC_{50}$ [μM] | $HA_{50}$ [μM] | $IC_{50}/HA_{50}$ |
|---|---|---|---|---|---|
| 338983 | Phor 18 | 75.3 | 2.06 ± 0.5<br>N = 16 | Not lytic | 0 |
| 338984 | (KKKFAFA)₃-βCG-ala | 83.8 | 4.4 ± 2.0<br>N = 29 | Not lytic | 0 |
| 338611 | (D Ala)-Phor21-LHRH | 85.1 | 0.75 ± 0.1<br>N = 8** | 672.9 ± 155 | 0.001 |
| 338612 | Phor18-ASAAS-LHRH | 78.9 | 0.88 ± 0.12<br>N = 36*** | 410.1 ± 42 | 0.002 |
| 338613 | Phor18-LHRH | 81.4 | 0.87 ± 0.11<br>N = 17** | 297.9 ± 35 | 0.003 |
| 338614 | (KKKFAFA)₃-LHRH | 81.4 | 0.78 ± 0.21<br>N = 12*** | 95.7 ± 46.7 | 0.008 |
| 337476 | Phor18-βCG-ala V04099X1 | 84.2 | 1.22 ± 0.16<br>N = 16*** | 169.8 ± 24 | 0.006 |
| 339385 | D-ala-Phor18-LHRH | 65.5 | 1.42 ± 0.08<br>N = 8*** | Not lytic | 0 |
| 339347 | Phor18-Lupron | 83.2 | 1.95 ± 0.1<br>N = 8 | 21 ± 1.2 | 0.09 |

Significance compared to Phor21-βCG-ala (323033)
***p < 0.0005,
**p < 0.005,
*p < 0.05

Acute hemolytic activities for 21 fusion constructs including Phor18-Lupron and D-ala-Phor18-LHRH, were studied. The results are summarized in FIGS. 5 and 6, and Table 3.

Hemolytic activity was determined in 96 well plates using a serial dilution of peptides exposed to 0.5% human RBC. Controls were saline (no RBC death) or 0.1% Triton X 100 (100% RBC lysis). The peptide concentrations ranged from 0 to 100 μM. Incubations were conducted for 2 h.

To ascertain the $IC_{50}$ of various fusion constructs on different human cancer cell lines compared to cisplatinum, $IC_{50}$ of fusion constructs were evaluated as in Table 3. The results are shown below:

| | $IC_{50}$ [μM] values in Human Cancer Cell Lines compared to Cisplatinum | | | | |
|---|---|---|---|---|---|
| Cell Line | Cisplatinum | Phor18-LHRH | D-ala-Phor18-LHRH | Phor18-βCG | D-ala-Phor18βCG-ala |
| MDA-MB-435S.luc | Not determined | 0.86 ± 0.16 | 1.42 ± 0.08 | 1.35 ± 0.15 | 1.6 ± 0.16 |
| MDA-MB-231 | HCT | 5.5 ± 1.2 | 33.7 ± 6.7 | 6.1 ± 0.6 | 20.5 ± 7.2 |
| AN3-CA | 11.85 ± 0.16 | 3.8 ± 0.08 | 40.6 ± 0.15 | 22.15 ± 0.16 | 36.8 ± 0.16 |
| OVCAR-3 | 184 ± 0.16 | 3 ± 0.5 | 13.8 ± 0.3 | 8.8 ± 0.4 | 11.6 ± 0.3 |
| SKOV-3 | 321 ± 10 | 11.8 ± 0.3 | 19.2 ± 0.2 | 10.9 ± 0.6 | 18.9 ± 0.4 |
| LNCaP | 19.9 ± 1.4 | 1.55 ± 0.08 | 5.0 ± 0.15 | 10.05 ± 0.16 | 15.5 ± 0.16 |

Breast cancer cell lines: MDA-MB-435S.luc, MDA-MB-231
Ovarian cancer cell lines OVCAR-3, SKOV-3
Prostate Cancer cell line: LNCaP
Endometrial cancer cell line: AN3-CA The data in general indicate very low hemolytic activities for the fusion constructs studied, except for Phor21-LHRH, LHRH-Phor21 and Phor18-Lupron. Under similar conditions the following fusion constructs did not show any hemolytic activity (see FIG. 5): Phor15-aminocaproic acid-β-CG-ala (337474), D-ala-Phor21 β-CG-ala (337481)>150,000 μM, Phor21, unconjugated Phor 18=CLIP71, (KKKFAFA)₃ (SEQ. ID NO. 16)-βCG-ala, Phor 21 (338982), Phor18=CLIP71 (338983), D-ala-Phor18-LHRH (339385) and (KKKFAFA)₃ (SEQ. ID NO. 16)-LHRH (338984). D-amino acid enantiomers had no measurable hemolytic activity.

Fusion constructs with hemolytic activities <50 μM were as follows: Phor21-LHRH (25 μM), LHRH-Phor21 (33 μM) and Phor 18-Lupron (21 μM).

Fusion constructs with hemolytic activities >100 μM were as follows: Phor18-β-CG-ala (337476), and Phor18-LHRH (338613).

Fusion constructs with hemolytic activities between 50-100 μM were as follows: (KKKFAFA)₃ (SEQ. ID NO. 16)-LHRH (95 μM), Phor21-βCG-ala and Phor21-ASAAS (SEQ. ID NO. 11)-βCG-ala had similar HA50 of 70 μM.

Fusion constructs with hemolytic activities between 400-1300 μM were as follows: Phor14-βCG-ala (337464), Phor18 GSGGS (SEQ. ID NO. 10) β-CG-ala (337467), Phor18 ASAAS(SEQ. ID NO. 11) β-CG-ala, (337470), Phor15 ASAAS(SEQ. ID NO. 11) β-CG-ala (337471), D-ala-Phor21-LHRH (338611), and Phor18-ASAAS(SEQ. ID NO. 11)-LHRH (338612).

A clinically significant criterium is ratio of cell toxicity ($IC_{50}$) and Hemolytic Activity ($HA_{50}$), or $IC_{50}/HA_{50}$ (FIG. 6, Table 3). In vivo studies were performed using a maximal concentration of 10 µM fusion construct which is several factors below the $HA_{50}$ values measured for most fusion constructs.

LHRH-conjugates with D-ala-Phor21, Phor18-ASAAS (SEQ. ID NO. 11), D-ala-Phor18 and Phor18 had very low $IC_{50}/HA_{50}$ ratios of 0.001-0.006 (compare Phor21-βCG-ala 0.03). Toxicity to MDA-MB-435S.luc cells is significantly higher compared to Phor21-βCG-ala: D-ala) Phor21-LHRH is 3 times more toxic than Phor21-βCG-ala, Phor18-LHRH and Phor18-ASAAS(SEQ. ID NO. 11)-LHRH is 2 times more potent, D-ala-Phor18-LHRH is 1.5 more potent (FIG. 6).

In summary, fusion constructs evaluated by criteria of increased toxicity and less hemolytic activity ($IC_{50}/HA_{50}$ ratio) would be: Phor18-βCG-ala, Phor18-ASAAS(SEQ. ID NO. 11)-βCG-ala, Phor15-ASAAS(SEQ. ID NO. 11)-βCG-ala, Phor15-C6-βCG-ala, D-ala-Phor21-LHRH, Phor18-LHRH, Phor18-ASAAS(SEQ. ID NO. 11)-LHRH, and D-ala-Phor18-LHRH.

Example 3

This example describes in vivo studies in a mouse xenograft model of breast cancer with various types and doses of βCG- and LHRH-fusion constructs.

Female Nu/Nu mice were injected subcutaneously with a MDA-MB435S.luc/Matrigel HC suspension ($1 \times 10^6$ cells). The treatment schedule is shown in FIG. 7. In brief, treatment started on day 13 after tumor cell injection and continued on day 19 and 25. Treatments were: saline control, Phor21 (5 mg/kg), Phor18 (5 mg/kg), (KKKFAFA)$_3$ (SEQ. ID NO. 16) peptide—βCG-ala (5 mg/kg), Phor21-βCG-ala (0.01, 1 and 5 mg/kg), Phor18-βCG-ala (0.01, 1 and 5 mg/kg), D-ala-Phor21-βCG-ala (0.01, 1 and 5 mg/kg), baseline 8-12 mice per group, 14 groups. The doses for weekly injections were 5, 1 and 0.01 mg/kg body weight, given as a bolus single injection.

All groups of mice tolerated the injections well. Only one mouse died at each injection with 337476 at the 5 mg/kg dose. Death was an acute event. All mice in other treatment groups survived. No mice died as a consequence of injection later than 10 minutes post injection.

The effect of cytolytic peptide injections on the primary tumors is illustrated in FIG. 8. In brief, the FIGS. 8A-8C show tumor volume during the course of the study for each individual peptide. FIGS. 8D-8G show tumor characteristics at necropsy: tumor volume (D), tumor weight (E), live tumor cells (F), tumor conditions (G).

Figure 8C:
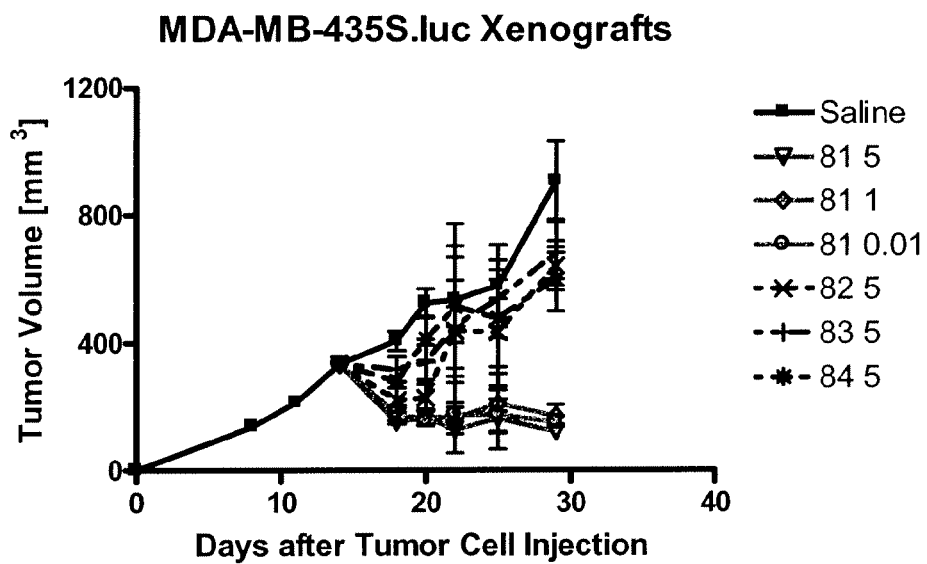
Figure 8D:
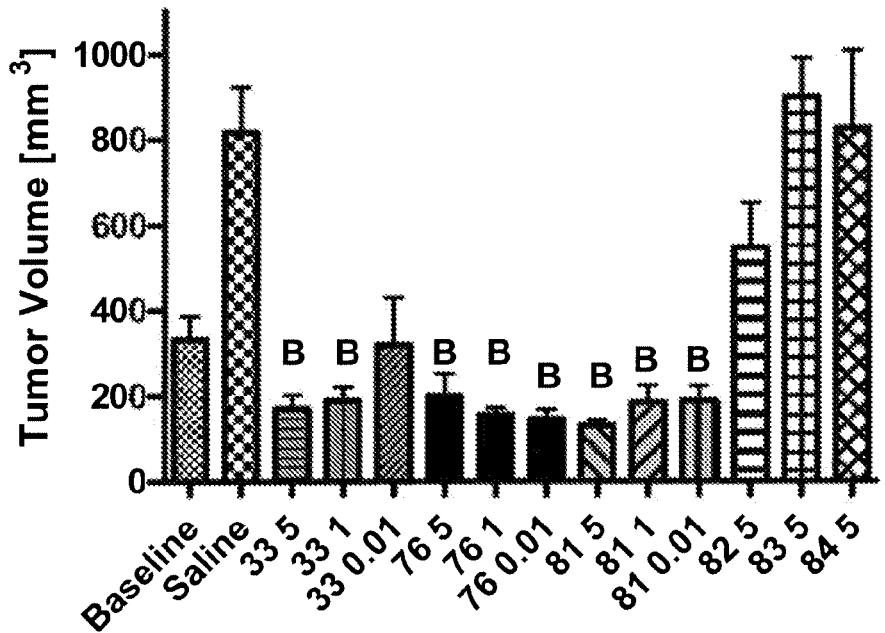
Figure 8E:
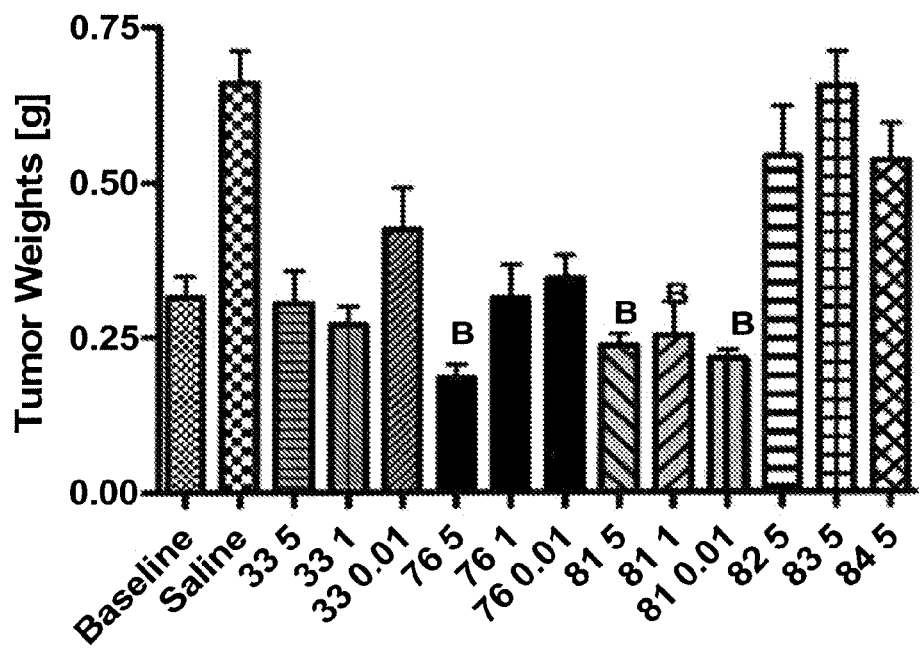
Figure 8F:
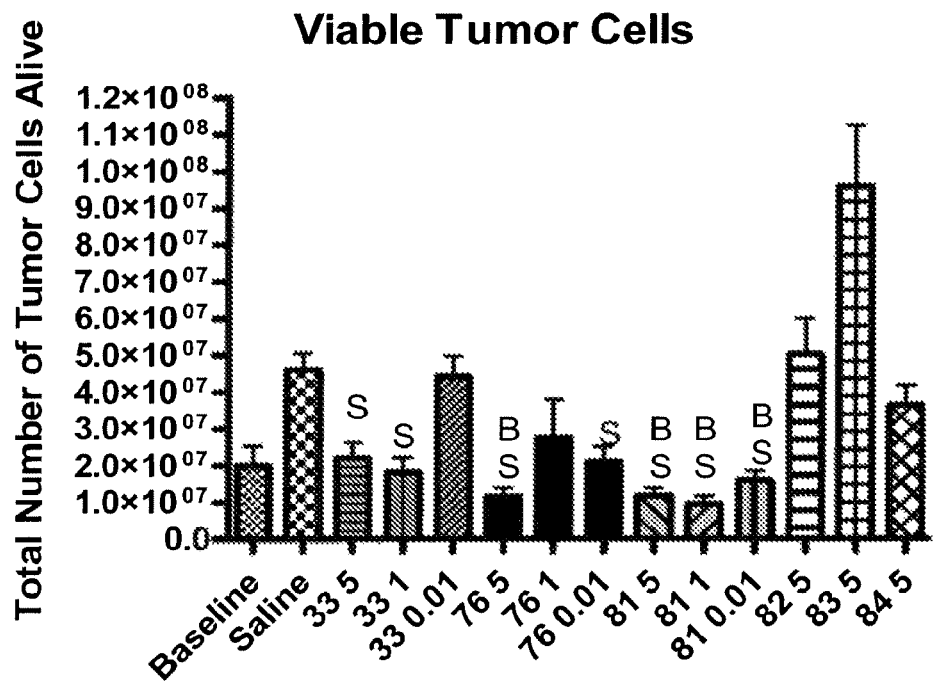
Figure 8G:
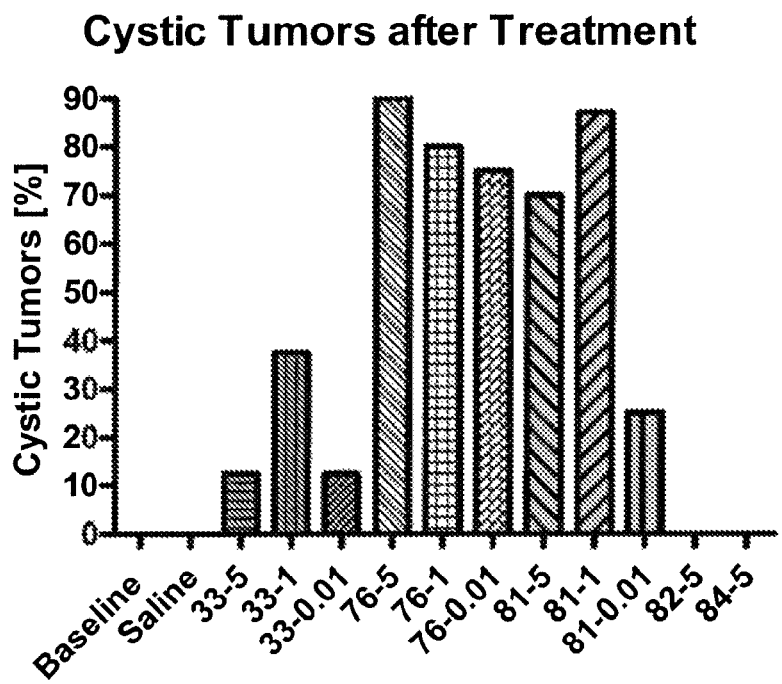
Figure 8H:
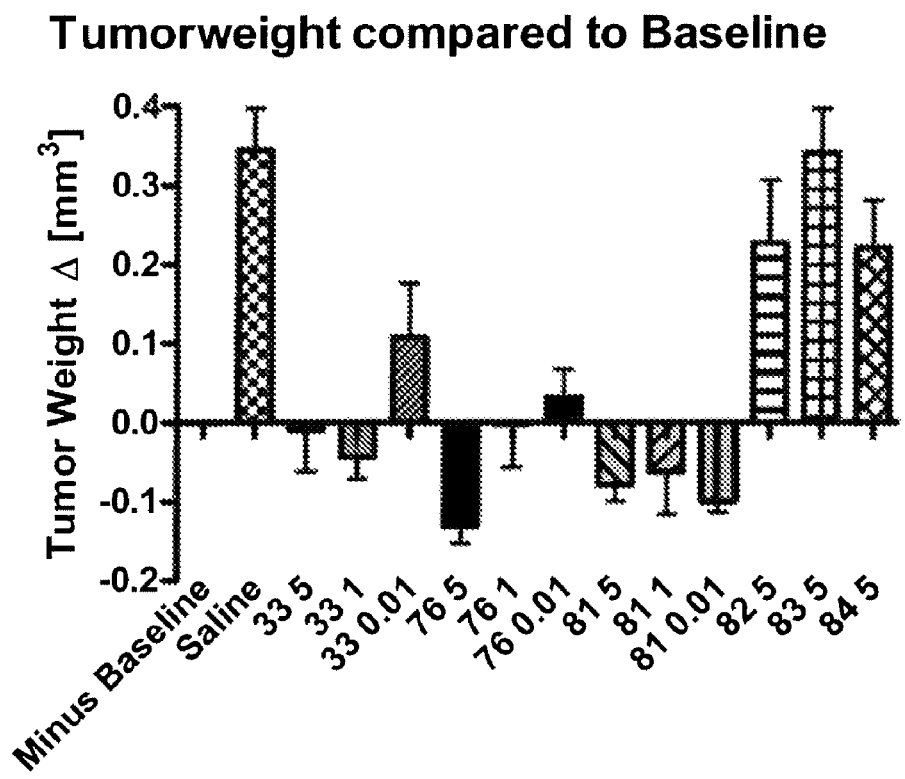
Figure 8I:
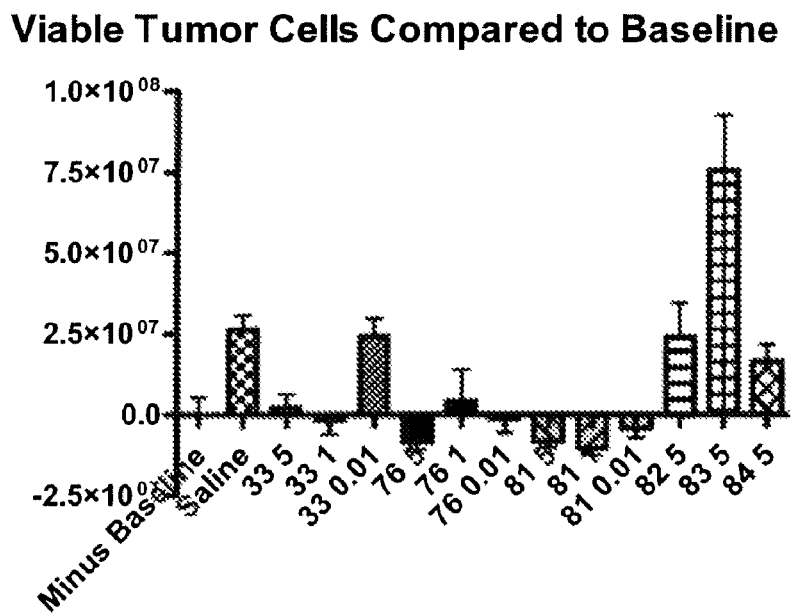
Figure 8J:
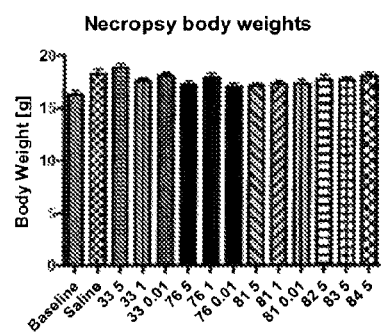
Figure 9A:
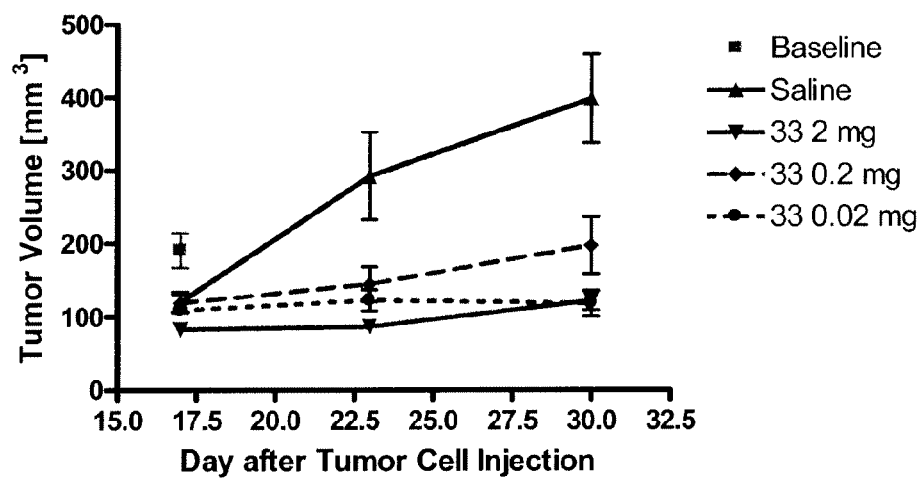
Figure 9B:
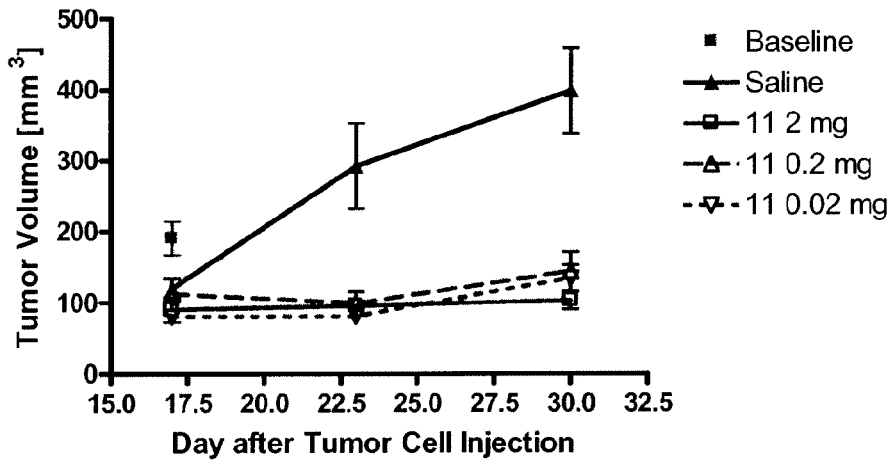
Figure 9C:
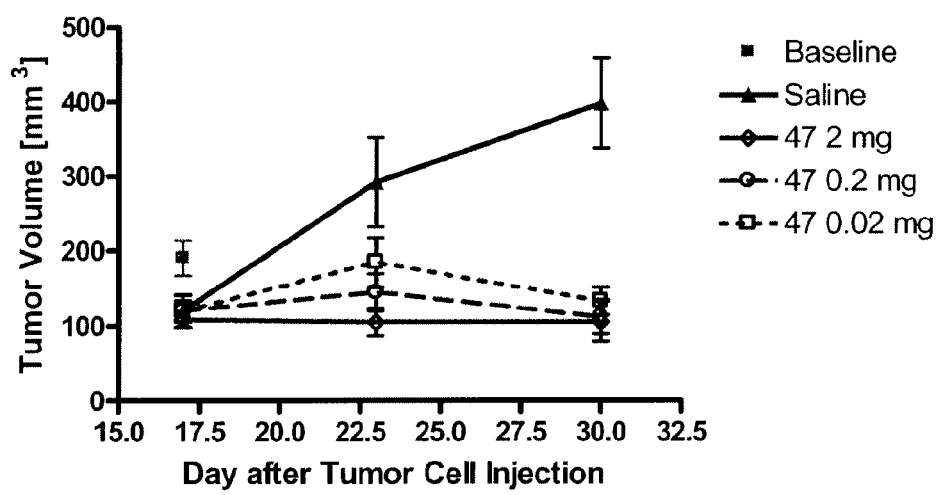
Figure 9D:
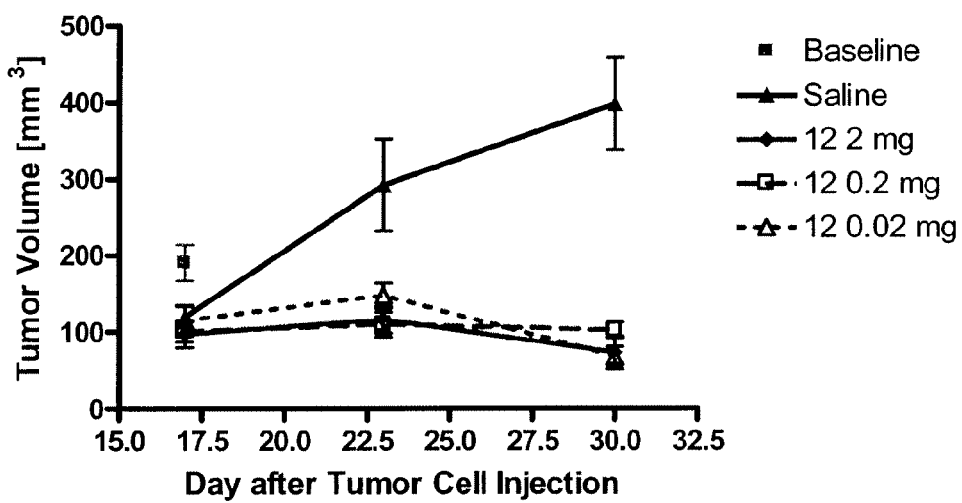
Figure 9E:
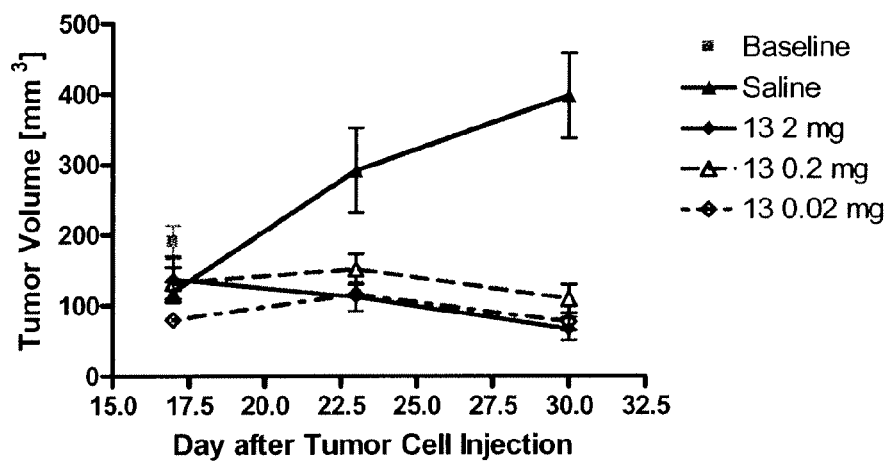
Figure 9F:
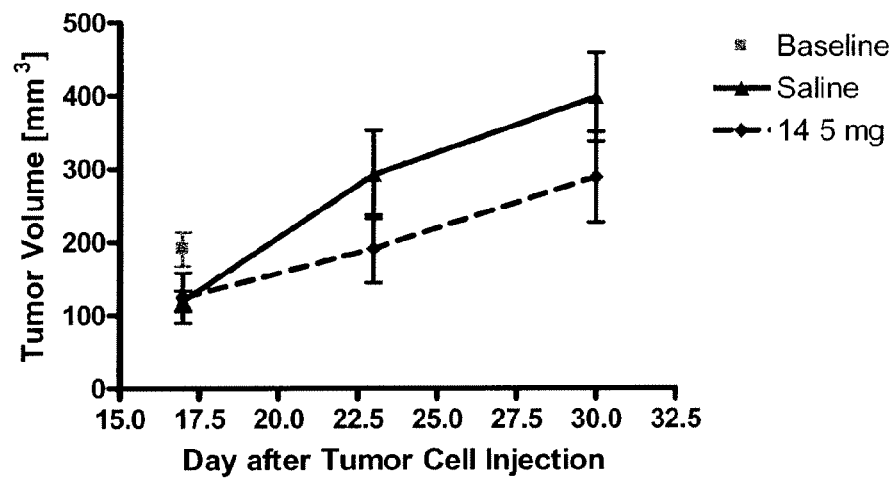
Figure 9G:
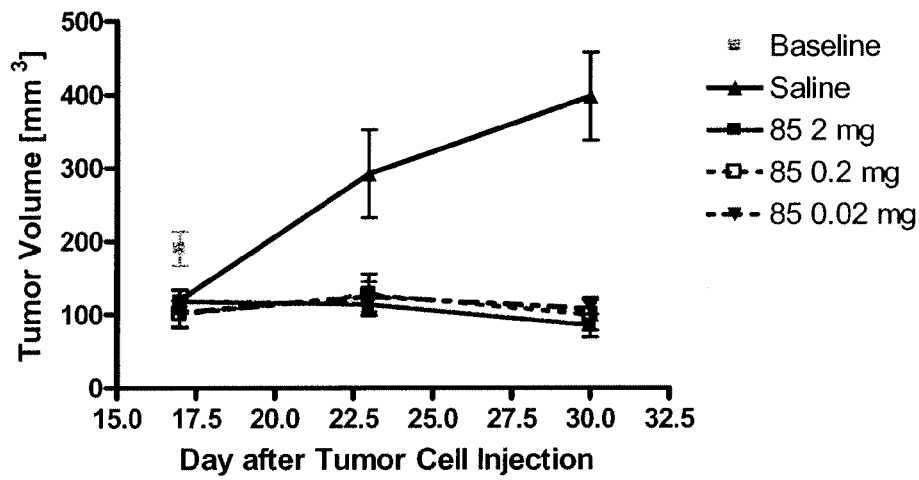
Figure 9H:
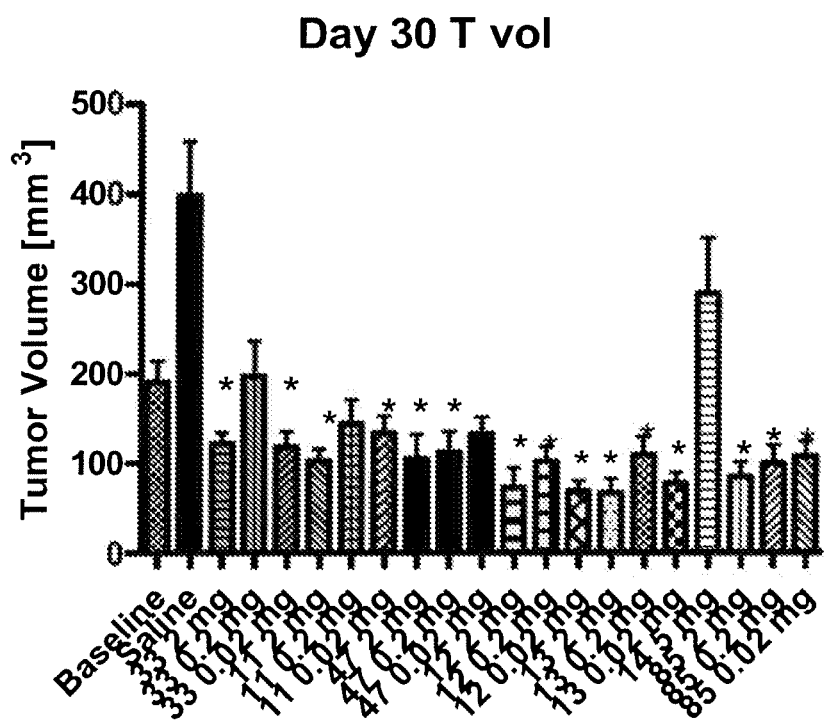

Treatment efficacy was calculated as difference between measurements at the beginning of treatment compared to the measurement at the end of study (FIG. 8H-8I). FIG. 8J shows bodyweight of mice at necropsy. Viability of cells in the tumors was determined at the end of the study when tumors were measured for luciferase activity.

Tumor volume decreased significantly in all animals treated with peptides containing βCG as a ligand (II, A), $p<0.05$ compared to baseline (except for 323033) at 0.01 mg/kg and the (KKKFAFA)$_3$ (SEQ. ID NO. 16)-βCG-ala, Phor 21 and unconjugated Phor 18=CLIP71 controls. Tumor volumes were significantly reduced compared to saline controls in all treatment groups except for (KKKFAFA)$_3$ (SEQ. ID NO. 16)-βCG-ala, Phor 21 and Phor 18, which were ineffective in reducing the xenograft volume.

Tumor weights also decreased significantly ($p<0.001$) in all treatment groups with βCG conjugated peptides when compared with animals treated with saline or (KKKFAFA)$_3$ (SEQ. ID NO. 16) peptides.

Treatment efficacy measured as reduction of tumor weight or viable tumor cells compared to baseline values showed a concentration dependent treatment response for 323033 and 337476. 337481 showed consistently reduction of tumor load and live tumor cells at 0.01, 1 and 5 mg/kg dosages. 323033 was most effective at 1 mg/kg dose compared to 5 mg/kg (we have observed this in previous experiments already), but is only significantly different to saline controls at the lowest dose applied. Fusion constructs 337476 and 337481 are significantly more effective at 5 and 0.01 mg/kg compared to 323033 ($p<0.0001$) in reducing tumor loads and viable tumor cells ($p<0.004$) below the baseline values. Fusion construct 337481 shows no concentration dependency and was the most effective of all tested constructs.

Cystic tumors were found in mice treated with fusion constructs 337476 and 337481, which occurred to 80-90%, but only to 30% in the 1 mg/kg 323033 treatment group. (Cyst formation has not been seen in this xenograft model. The cysts consisted of liquid filled capsules.) Although it is not clear, it has been postulated that cystic tumors occur when cells are killed rapidly in a fast growing tumor. Cysts were present in prostate tumor xenografts treated with Phor 21.

Blood chemistry and complete blood count results for the treatment groups revealed that in no case did treatments affect liver, kidney, heart function. Platelet count, WBC and RBC counts were within normal range, indicating that the treatment does specifically kill tumor cells, and did not cause anemia at the given concentration nor affected any other observable vital body function. The fusion constructs were well tolerated with no long term side effects.

Based upon the foregoing in vivo tumor efficacy data, Phor18-βCG-ala (337476) and D-ala-Phor21-βCG-ala (337481) are significantly more potent than reference Phor21-βCG-ala (323033) with respect to tumor weight reduction ($p<0.0001$) and destruction of viable tumor cells ($p<0.004$) compared to baseline values. Both fusion constructs did not cause hemolysis in vivo and did not show persistent side effects at the highest dose used (5 mg/kg). It is possible that tumor efficacy of Phor18-βCG-ala would be greater with multiple injections even at the lowest dose.

For LHRH fusion constructs, the mouse xenograft model for breast cancer was used. In brief, Nu/Nu female mice, outbred strain, age 5 weeks (Charles River) were injected subcutaneously with a MDA-MB-435S.luc/Matrigel suspension ($1 \times 10^6$ cells). Treatment was started on day 21 after tumor cell injection and continued on day 26 and 29. The doses for weekly fusion construct injections were 2, 0.2 and 0.02 mg/kg body weight, given as a bolus single injection. All mice were necropsied 34 days after tumor cell injection-baseline values for tumor weights were obtained by sacrificing 8 mice at treatment start. Primary tumors, liver, kidney, pancreas, heart, lung, and spleen were collected and prepared for histological evaluation in formalin. Tumor weights were recorded at necropsy, part of the tumors were frozen at −80° C. for luciferase assay determination.

Treatment groups included saline control, Phor21-βCG-ala—323033 (0.02, 0.2 and 2 mg/kg), D-ala-Phor21-LHRH—338611 (0.02, 0.2 and 2 mg/kg), (KKKFAFA)$_3$ (SEQ. ID NO. 16) LHRH—338614 (5 mg/kg), Phor18-LHRH—338613 (0.02, 0.2 and 2 mg/kg), Phor18-ASAAS (SEQ. ID NO. 11)-LHRH—338612 (0.02, 0.2 and 2 mg/kg), D-ala-Phor18-LHRH—339385 (0.02, 0.2 and 2 mg/kg), and Phor18-Lupron—339347 (0.02, 0.2 and 2 mg/kg), baseline 12 mice per group.

All groups tolerated the injections well. Only two mice died during the second and third injection with Phor18-ASAAS(SEQ. ID NO. 11)-LHRH at the 2 mg/kg dose (these mice were from the same cage). Death was an acute event. All mice in other treatment groups survived. No mice died as a consequence of injection later than 10 minutes post injection.

FIG. 9 summarizes the effects of fusion construct injections on the primary tumors as volume measures during the course of the study for each individual construct. In all groups tumor volumes decreased during treatment except for mice treated with the (KKKFAFA)$_3$ (SEQ. ID NO. 16)-LHRH conjugate or in saline control, where exponential tumor growth was observed. The tumor volume recorded after 30 days post treatment shows a reduction (p<0.01) compared to baseline for all fusion constructs with the smallest tumor volumes recorded in treatment groups with Phor18-ASAAS(SEQ. ID NO. 11)-LHRH and Phor18-LHRH.

Characteristics of tumors at necropsy are summarized in FIG. 10: (A) tumor weight, (B) changes of tumor weights compared to baseline, (C) total number of live tumor cells, (D) changes of total live tumor cells compared to baseline, and (E) body weights at baseline and necropsy. Viability of tumor cells was determined at the end of the study when tumors were measured for luciferase activity. Treatment efficacy was calculated as difference between measurements at the beginning of treatment compared to the measurement at the end of study (FIGS. 10B and 10D).

Tumor weights and total numbers of live tumor cells decreased significantly in all animals in all treatment groups even at the lowest dose of 0.02 mg/kg when LHRH conjugates were given compared to saline control and to (KKKFAFA)$_3$ (SEQ. ID NO. 16)-LHRH conjugated peptide (p<0.0001). Total tumor weights decreased compared to baseline significantly in all animals treated with 2 mg/kg peptides containing LHRH and at 0.02, 0.2 and 2 mg/kg for D-ala-Phor18-LHRH (A), (p<0.05).

The following concentrations resulted in tumor weights similar to baseline: Phor21-βCG-ala-323033) at 0.02 mg/kg (p<0.07) and 0.2 (p<0.06); Phor18-Lupron at 0.2 and 0.02 mg/kg dosage, Phor18-LHRH at 0.2 mg/kg, and D-ala-Phor21-LHRH at 0.2 mg/kg. When total tumor weights were compared to 0.02 mg/kg dose of Phor21-βCG-ala, Phor18-ASAAS(SEQ. ID NO. 11)-LHRH and D-ala Phor18-LHRH were superior at 0.02 mg/kg dosage (p<0.05).

Figure 10A:
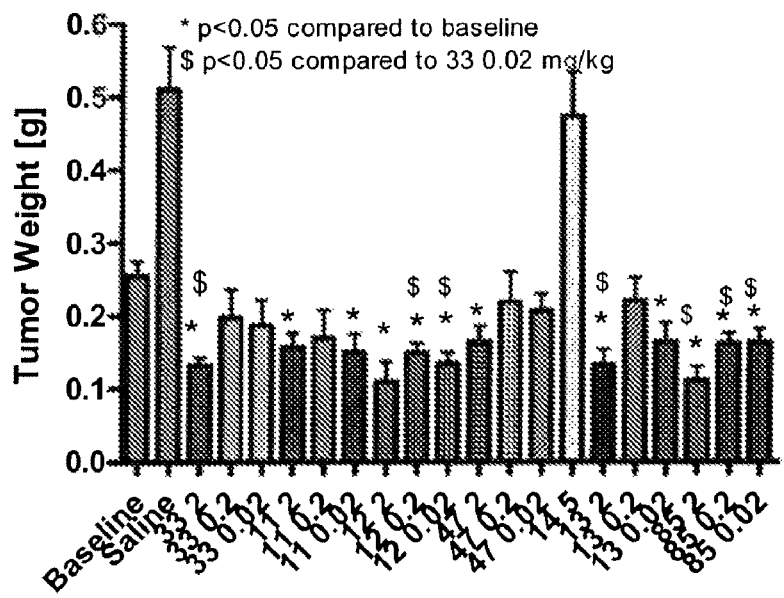
Figure 10B:
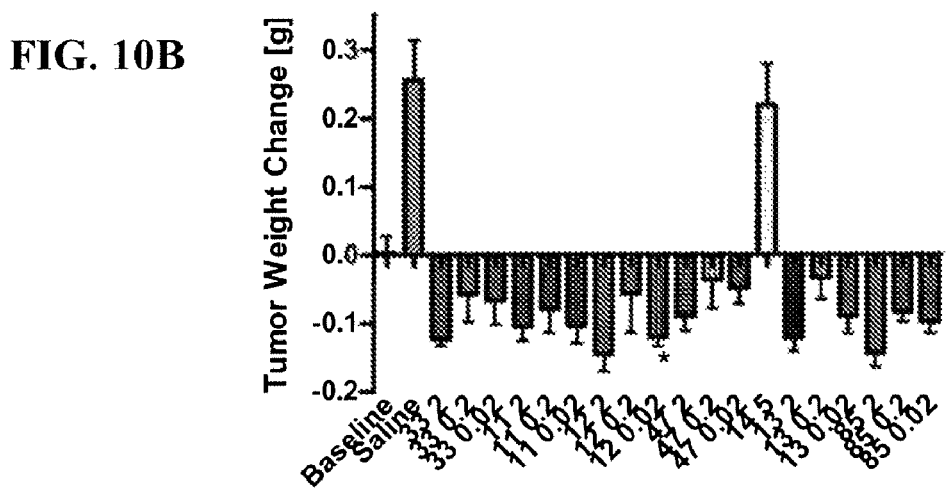
Figure 10C:
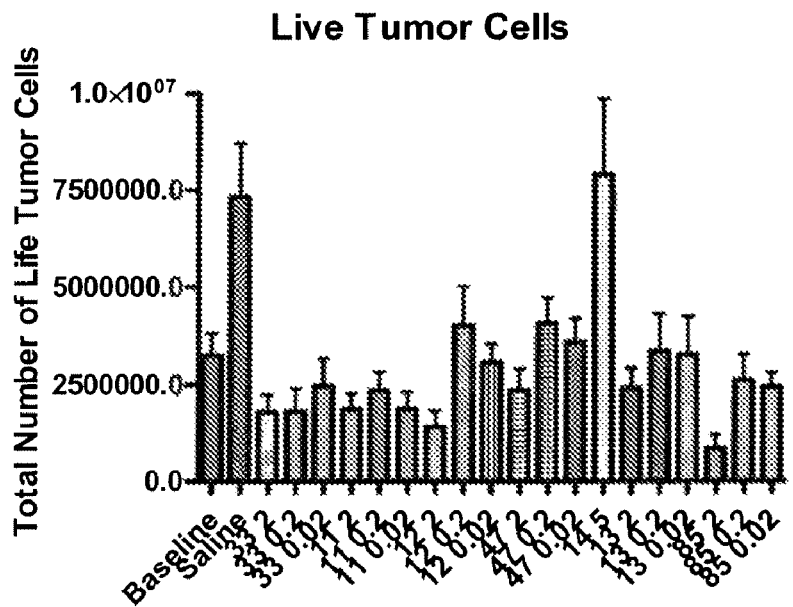
Figure 10D:
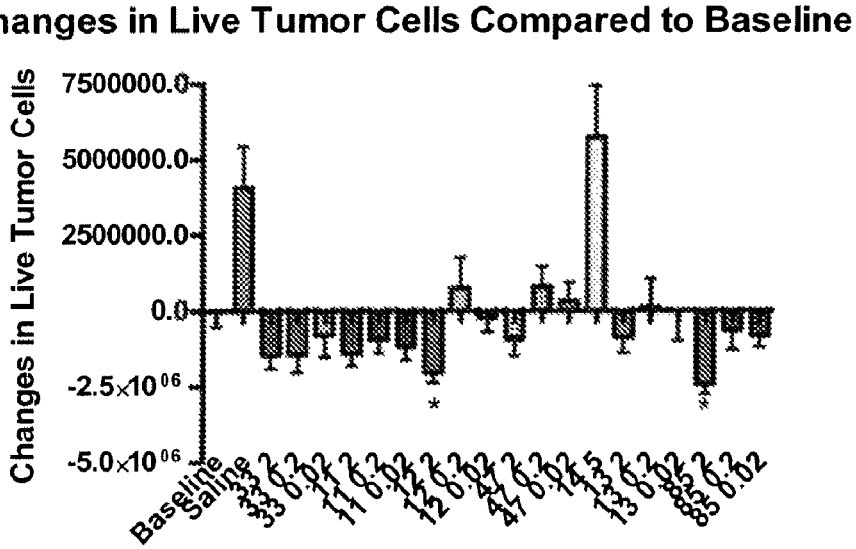
Figure 10E:
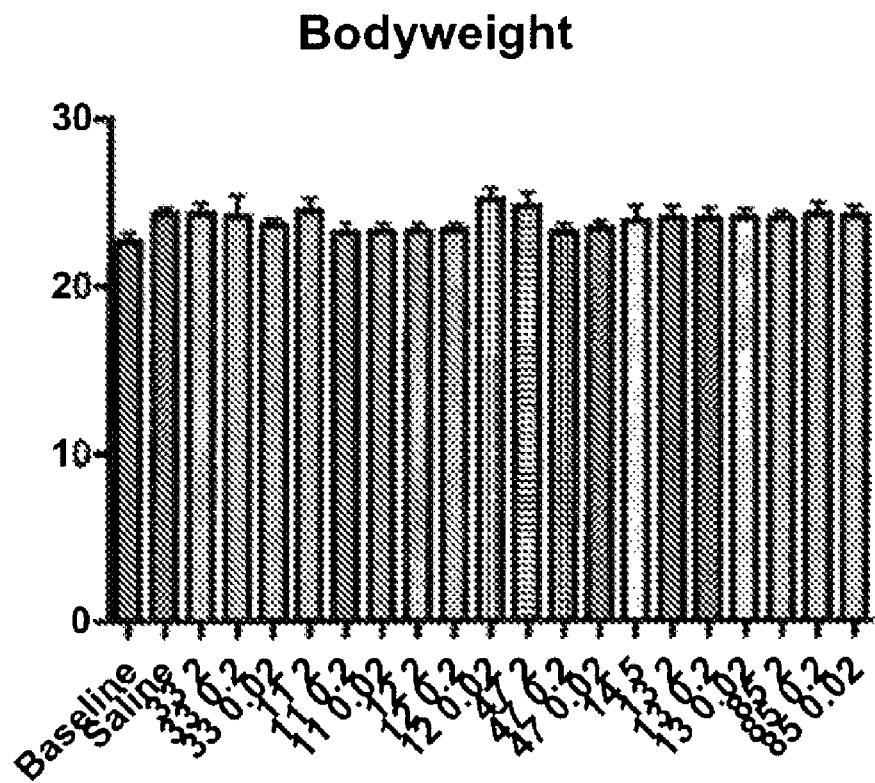

The number of live tumor cells was determined and plotted in FIG. 10C as total number of live tumor cells and in FIG. 10D as changes in live tumor cells compared to baseline. Cell viability, as measured by luciferase activity, correlated with the observed changes in tumor weight and tumor volume except for Phor18-ASAAS(SEQ. ID NO. 11)-LHRH and Phor18-LHRH, where a reduction of live tumor cells was observed. Treatment with D-ala-Phor18-LHRH (339385) and Phor18-ASAAS(SEQ. ID NO. 11)-LHRH (338612) were superior to Phor21-βCG-ala at 2 mg/kg dose (p<0.04).

Treatment efficacy measured as a reduction of tumor weight or viable tumor cells compared to baseline values showed a concentration dependent treatment response for all fusion constructs except for D-ala-Phor21-LHRH regarding tumor weights and live tumor cells. D-ala-Phor18-LHRH showed consistently reduction of tumor weights and live tumor cells at 0.02, 2 and 2 mg/kg dosages. Most effective fusion constructs in this experiment was Phor18-ASAAS (SEQ. ID NO. 11)-LHRH (338612), and D-ala-Phor18-LHRH (339385) in reducing the number of live tumor cells and tumor weights at 2 mg/kg. Phor18-ASAAS(SEQ. ID NO. 11)-LHRH and D-ala-Phor18-LHRH were superior compared to 2 and 0.02 mg/kg dose of Phor21-βCG-ala, (p<0.05). Phor18-Lupron was least effective at reducing tumor weight and live tumor cells.

Blood chemistry and complete blood count results for the treatment groups revealed that in no case did the treatments affect liver, kidney, heart function. Platelet count, WBC and RBC counts were within normal range, suggesting that the treatment does specifically destroys tumors, and did not cause anemia at the given concentration and they did not affect any other observable vital body functions. Elevated potassium levels of 1.5 fold compared to saline controls were observed in mice injected with Phor18-Lupron, Phor18-LHRH and D-ala-Phor21-LHRH. The fusion constructs were well tolerated with no long term side effects.

Based upon the foregoing in vivo tumor efficacy data, Phor18-ASAAS(SEQ. ID NO. 11)-LHRH (338612), and D-ala-Phor18-LHRH (339385) are significantly more potent than reference Phor21-βCG-ala with respect to tumor weight reduction (p<0.05) and destruction of viable tumor cells (p<0.04). Equally effective as Phor21-βCG-ala were D-ala-Phor21-LHRH, and Phor18-LHRH. Both fusion constructs did not cause hemolysis in vivo or other side effects. It is possible that the efficacy of Phor18-ASAAS-LHRH (338612), and D-ala-Phor18-LHRH (339385) would be greater with multiple injections even at the lowest dose.

Example 4

This example describes in vitro and in vivo receptor expression and specificity studies.

LH receptor expression density both before and after treatment will be analyzed to determine if treatment results in down regulation of receptor expression. Immunocytochemistry in comparison to Western Blot assays and RIA for quantification. LH and LHRH receptor determination in MDA-MB-435S.luc cells, CHO and TM4 cells using IHC with chamber slides, and Western Blot techniques. The same passage number of each cell line will be tested for sensitivity to lytic peptide CG and lytic peptide LHRH.

Specificity of LH receptor fusion constructs was analyzed in MDA-MB435S.luc (both LHRH and CG receptors), TM4 (no LHRH receptors) and CHO (no CG receptors) cells. IC$_{50}$ data show a significant reduction in sensitivity in TM4 cells for LHRH-Phor21 (10.9 μM), whereas CHO cells show low sensitivity to Phor21-βCG-ala (24.6 μM) when compared to MDA-MD-435S.luc cells (2.3 μM) (FIG. 12).

In vivo receptor expression is measured in connection with fusion construct treatment. In vivo receptor expression is measured at beginning and end of fusion construct treatment.

Example 5

This example describes combination treatment with fusion constructs and a chemotherapeutic agent.

Preliminary studies of ovarian cancer cell lines (OVCAR-3 cells, multi drug resistant) incubated for 48 h with Phor21-βCG-ala and doxorubicin were performed. Cell viability was determined as formazan reduction. A decrease of IC$_{50}$ with increasing doxorubicin treatment in simultaneous incubation with Phor21-βCG-ala. The decrease is from 10 μM to 0.9 to 0.3 to 0.05 μM at doxorubicin concentrations of 0, 0.5, 2 and 10 μg/ml. (FIG. 11). Treatment with Phor21-βCG-ala potentiated the response to doxorubicin. The data showed that Phor21-βCG-ala is more effective (13 fold) when cells are co-incubated with doxorubicin.

Pretreatment of cancer cells with doxorubicin or cisplatinum, followed by treatment with LH or LHRH fusion constructs in the presence and absence of LH or LHRH, will show if cytotoxicity of cells to the construct is altered.

In vivo efficacy of combination treatment was tested in a xenograft tumor model (MDA-MB-435S). Mice are treated with a combination of a fusion construct and a chemotherapeutic drug and compared to appropriate controls. Mice were treated according to the standard schedule used for the drug, and are treated once a week for 3 weeks with the fusion construct.

The fusion conjugates have a high safety margin considering parameters such as hemolytic activity, maximum tolerated dose (MTD) (up to 16-25 mg/kg) in comparison with the anti-tumor effective dose (0.02 or 0.01 mg/kg). The safety margin for Phor21-βCG-ala is 16 whereas a value of 800 can be reached for Phor18-βCG-ala and Phor18-LHRH. In comparison the safety margin for Phor18-Lupron is only 8.

Table 6 below is a summary of the conjugates according to various criteria.

Example 6

This example describes peptide KFAKFAKKFAK-FAKKFAKQHWSYGLRPG (SEQ. ID NO. 15) (Phor18-LHRH (338613)) in vitro kinetic studies in various cancer cell lines.

Standard chemotherapeutic drugs interact through DNA intercalation, microtubule interaction or are inhibitors of signal transduction pathways. Hence, their mechanism of action determines the time frame necessary to destroy target cells. The kinetics for doxorubicin in vitro to destroy human breast cancer cells such as MDA-MB-435S has been reported to be as rapid as 4 hours, and other standard of care treatments may even take longer. The most common mechanism of action in destroying cancer cells is apoptosis. As a reversible process and due to the occurrence of multi-drug resistance (MDR), action of Pgp pumps that export drug molecules in MDR cancer cells, standard of care treatments can be ineffective.

In contrast to chemotherapeutic drugs, direct membrane action can destroy cancer cells within minutes. Membrane

| Peptide | Increased in vitro activity fold[1] | Hemolytic Activity $[\mu M]^2$ | $IC_{50}/HA_{50}$ | In vivo Performance compared to 33[4] | MTD mg/kg[5] | Performance Rating |
|---|---|---|---|---|---|---|
| Phor21-βCG-ala(33) | 1 | 73.4 | 0.03 | 1 | 16 | |
| D-ala-Phor18-LHRH (85) | 1.5 | Not lytic | 0 | Superior | 25 | 14 |
| Phor18-βCG-ala (76) | 2.11 | 169 | 0.006 | Superior | 16 | 13 |
| Phor18-LHRH (13) | 2.65 | 297 | 0.003 | 1 | 16 | 13 |
| D-ala-Phor21-βCG-ala (81) | 1 | Not lytic | 0 | Superior | 8 | 11* |
| Phor18-ASAAS-LHRH (12) | 2.62 | 410 | 0.002 | Superior | No data | 11 |
| D-ala-Phor21-LHRH (11) | 3.08 | 672 | 0.001 | 1 | No data | 10$^a$ |
| Phor18-Lupron (47) | 1 | 21 | 0.04 | Less | 16 | 5 |
| 71 | 1.6 | 421 | 0.003 | No data | No data | |
| 74 | 1.8 | Not lytic | 0 | No data | No data | |

Rating code:
Points allocated: 1 2 3
In vitro activity 1x 2x 3x
$HA_{50}$ <50 50-100 >100
$IC_{50}/HA_{50}$ <0.03 <0.006 <0.004
In vivo efficacy Compared to 33 equal better
MTD compared To 33 equal better
[1]$IC_{50}$ of 33 was 2.31 µM, values expressed as $IC_{50}$ of 33/$IC_{50}$ peptide.
[2]Hemolytic activity expressed as $HA_{50}$ [µM].
[3]In vivo performance refers to significance in tumor weight reduction and life tumor cell reduction vs baseline values compared to the same parameters of peptide 33.
[4]Injected dose resulting in 66.6% survival (acute and 8-14 days post injection).
Peptide codes:
33 = Phor21βCG-ala
76 = Phor18-βCG-ala
81 = D ala Phor21-βCG-ala
85 = D ala Phor18-LHRH
47 = Phor18-Lupron
13 = Phor18-LHRH
11 = D ala Phor21-LHRH
12 = Phor18-ASAAS-LHRH
71 = Phor15-βCG-ala
74 = Phor15-C6-βCG-ala active compounds such as cationic lytic peptides include Phor18-LHRH (338613) (KFAKFAKKFAKFAKKFAKQH-WSYGLRPG) (SEQ. ID NO. 15).

To determine the kinetics of cytotoxicity detailed time course studies were conducted using Phor18-LHRH (338613) in comparison to the untargeted lytic peptide moiety Phor 18=CLIP71 (338983) in various cell lines expressing LHRH target receptors at various levels. Membranes of non-cancerous cell lines are neutral and are resistant to cytolytic peptides, in contrast to cancer cell lines, which have a high phosphatidic acid content in their outer membrane.

The breast cancer cell lines studied were MDA-MB435S (estrogen receptor alpha negative), MCF-7 and T47D (estrogen receptor alpha positive), ovarian cancer cell lines (OVCAR-3 and SKOV-3), prostate cancer (LNCaP), the non-malignant breast epithelial cell line MCF-10A and the mouse fibroblast cell line NIH:3T3. The role of the LHRH receptor targeting in efficacy of Phor18-LHRH (338613) was also evaluated.

Cells were seeded into 96 well plates at a density of 10,000 cells/well. Treatment was initiated after 48 h by adding Phor18-LHRH (338613) (APC 338613, Lot # P080401) or Phor18=CLIP71 (APC 338983, Lot # WO8033C1) at concentrations of 0.0001, 0.001, 0.01, 0.1, 1, 5, 10, 50 and 100 µM. Controls contained USP saline or 0.1% TritonX-100™ as reference for 0 and 100% cell death, respectively. Incubations were terminated by removing the culture media after 2 minutes, 5 minutes, 15 minutes, 30 minutes, 1 hour, 2 hours, 6 hours, 24 and 48 hours. Cell viability was assessed through formazan conversion assay (MTT assay, (CellTiter 96 Aqueous One, Promega # G3582). Formazan conversion was determined using a BioRad Benchmark Plus microplate spectrophotometer dual wavelengths at 490/630 nm at room temperature).

Data were calculated as fraction of absorption in TritonX-100™ containing wells representing 100% cell death versus 0% cell death in saline containing wells. Cytotoxicity was determined as $IC_{50}$ using GraphPad Prism version 5.01 for Windows, GraphPad Software, San Diego Calif. USA according to the program for sigmoidal dose response with variable slope using constraint values of 0 and 100%. 4 wells of each individual set of two 96 well plates were compared and analyzed. Statistical analysis for significance was determined by a two-tailed Student's T-test.

In MDA-MB 435S cells (p250) Phor18-LHRH (338613) exhibited its maximal efficacy after 1 hour of incubation whereas CLIP71 incubations resulted in $IC_{50}$ values of 100, 109, 171, 145, 148, 86, 54.5, 55.1 (24 hours), and 3 [µM] (48 hours) (p<0.005) with increasing incubation time. Phor18-LHRH (338613) is a fast acting agent (1.2 µM 0.5 hour and 0.6 µM after 1 hour) compared to the unconjugated lytic peptide CLIP71 (>100 µM).

In MCF-7 cells (p152) Phor18-LHRH (338613) exhibited its maximal efficacy after 1 hour of incubation whereas CLIP71 incubations resulted in $IC_{50}$ values of 92, 95, 50 and 22 [µM] (p<0.005) with increasing incubation time. Phor18-LHRH (338613) is a fast acting agent (3.4-1.8 µM) compared to the unconjugated CLIP71.

In OVCAR-3 cells (p47) Phor18-LHRH (338613) exhibited its maximal efficacy after 1 hour of incubation whereas unconjugated Phor18=CLIP71 (33 incubations resulted in $IC_{50}$ values of 337, 126, 85.5, 52.5, 22.9 and 23.1 [µM] (p<0.005) with increasing incubation time. Phor18-LHRH (338613) is a fast acting agent with IC50 values of 6.7, 5.6, 5.3, 1.6, 1.5, 0.5 and 0.5 [µM] (p<0.005) with increasing incubation time. The rapid kinetic data suggest that Phor18-LHRH (338613) and CLIP71 kill cells by a different mechanism of action and increases the efficacy of the drug.

In SKOV-3 cells (p40) Phor 18-LHRH (338613) exhibited its maximal efficacy (11.5 µM) after 24 hours of incubation whereas CLIP71 incubations resulted in $IC_{50}$ values of 86, 96, 53 and 50 [µM] (p<0.005) with increasing incubation time. Phor18-LHRH (338613) is not an appropriate target for SKOV-3 cells since these cells do not present functional LHRH receptors.

All cell lines presenting functional LHRH receptors such as breast cancer cells (MDA-MB435 and MCF-7) and OVCAR-3 treated with Phor 18-LHRH (338613) demonstrated the maximum effect ($IC_{50}$ in µM) within 0.5-1 hour of incubation. In contrast, 24 hours incubation was required for the maximal effect of CLIP71. Similar results were obtained for cell lines that present functional LHRH receptors such as T47D, LNCaP. In cell lines that do not present functional LHRH receptors (SKOV-3 and HEK 1A), Phor 18-LHRH (338613) and Clip71 showed similar toxicity with $IC_{50}$ values of 0.10.3 resp 11.8 µM after 24 hour incubations. Non cancerous cell line 3T3 was highly resistant to Phor 18-LHRH (338613) and CLIP71 with $IC_{50}$ values of >40 µM for CLIP-71 and >10 µM for Phor 18-LHRH (338613).

These results indicate that LHRH targeting enhances the efficacy of CLIP71 and that non-cancerous cell lines are resistant to destruction by cytolytic cationic peptides. Phor18-LHRH (338613) shows remarkable potency in destroying cancer cells through a receptor targeted mechanism within less than 1 hour. Phor18-LHRH (338613) is effective within minutes and has advantages over standard chemotherapy that depend on intracellular uptake and interference with metabolic pathways and proliferation machinery for efficacy. Furthermore, Phor18-LHRH (338613) is capable of acting on multi-drug resistant cancer cells.

Example 7

This example includes data indicating a likely mechanism of action of peptide KFAKFAKKFAKFAKKFAKQH-WSYGLRPG (SEQ. ID NO. 15) (Phor18-LHRH (338613)) on breast cancer cells in vitro.

To demonstrate a possible mechanism of action in vitro a fluorescence microscopic study was conducted in the human breast cancer cell line MDA-MB435 that over express LHRH receptors. In brief, human breast cancer cells (MDA-MB435, passage #252) were seeded onto culture dishes. The following markers were introduced prior to adding EP100: DRAQ5™ (Alexis Corporation)—blue—was used for staining of the nucleus and MitoTracker® Red CMXRos (M7512) (Molecular Probes, Inc. OR) were applied for visualizing intact mitochondria. Cell membranes were stained with wheat germ alexa fluor green conjugates (Molecular Probes, Inc. OR).

Cells were loaded first with Mitotracker dye, according to the manufacturers recommendation. Phor18-LHRH (338613) reconstituted in saline was added at a final concentration of 10 µM and incubated for 5-10 minutes. Culture dishes with saline only served as controls. The supernatant was removed and the remaining cells prepared for fluorescence microscopy imaging.

A fluorescence microscopic evaluation of MDA-MB-435 presenting functional LHRH receptors breast cancer cells in vitro following exposure to Phor18-LHRH (338613) revealed disintegration of the plasma membrane after 5 minutes exposure to Phor18-LHRH (338613) (10 µM). These observations suggested that Phor18-LHRH (338613) destroyed the plasma membrane, leading to the death of the cell within minutes.

A fluorescence microscopic evaluation of SKOV-3 (p 41) and MDA-MB435S (p 250) cells in cultures incubated for 30 minutes with 2 μM Phor18-LHRH (338613) FITC revealed that in SKOV-3 cells intracellular uptake was absent, membrane blebbing did not occur, and mitochondrial dye was retained. In contrast in MDA-MB435S cells intracellular uptake of Phor 18-LHRH (338613) FITC was visible within 30 minutes as well as extensive membrane blebbing leading to vesicle formation of the outer membrane and fading of mitochondrial dye. These observations suggest cell death occurred within minutes.

Within minutes, Phor18-LHRH (338613) destroyed cells that present functional LHRH receptors. Phor18-LHRH (338613) destroyed cancer cells through disintegrating the outer plasma membrane leading to necrosis. The mechanism of action strongly suggests a fast interaction of Phor18-LHRH (338613) with the plasma membrane of cells that present the functional target. Cells that were negative for LHRH receptors were not a target and remained intact.

These data showed high specificity and efficacy of Phor 18-LHRH (338613) as an anticancer drug. Phor18-LHRH (338613) was effective within minutes and had major advantages over standard chemotherapy that require intracellular uptake and interference with metabolic pathways and proliferation machinery for efficacy. Furthermore, Phor 18-LHRH (338613) was capable of acting on multi-drug resistant cancer cells.

Mice were sacrificed one week after the last injection and blood collected for chemistry panel, tumor weights and body weights were recorded. Part of the tumors were fixed in PBS buffered 10% formalin for histological evaluation. The various in vivo xenograft studies are summarized in Table 7.

TABLE 7

Xenograft Studies

| Xenograft Model | Treatment Regimen and Duration | Median Tumor Weight vs Baseline $p < 0.05$ | Median Tumor Weight vs Saline $P < 0.05$ | Remarks |
|---|---|---|---|---|
| OVCAR-3 | 1 × 3 wk, 20 d | 0.2 mg/kg | 0.2, 2 mg/kg | Necrosis in treated tumors, reduction of LHRH receptors |
| MDA-MB-435S.luc | 1 × 3 wk, 22 d | 0.02, 2 mg/kg | 0.02, 0.2 and 2 mg/kg | |
| MDA-MB-435S.luc | 1 × 3 wk, 22 d | 0.002 mg/kg | 0.0002 mg/kg | Necrosis and reduction of LHRH receptors |
| PC-3 | 1 × 3 wk, 21 d | 0.2 | 0.002, 0.02, 0.2 mg/kg | |
| MCF-7 | 2 × 3 wk, 19 d | | 0.02 mg/kg growth delay | Necrosis in treated tumors 0.02 and 0.2 |

Example 8

This example includes studies demonstrating that peptide KFAKFAKKFAKFAKKFAKQHWSYGLRPG (SEQ. ID NO. 15) (Phor18-LHRH (338613)) was effective against cancer in a xenograft models.

In vivo efficacy studies were conducted as monotherapy, or a combination therapy with standard of care treatments in nude mice bearing human breast cancer xenografts: MDA-MB435S.luc (s.c.), MCF-7 (estrogen receptor alpha positive), human ovarian cancer xenografts: OVCAR-3, (s.c.), human prostate cancer xenografts: PC-3 (androgen receptor negative). Phor18-LHRH (338613) dissolved in saline (0.02, 0.2 and 2 mg/kg) was injected once or twice a week for 3 weeks as a single bolus injection in into the lateral tail vein.

PHOR 18-LHRH (338613) Combination therapies were conducted in a MCF-7 breast cancer xenograft models.

To determine the minimal effective dose necessary to reduce MDA-MB-435S xenograft weights in a single dose regimen, Nu/Nu female mice, outbred strain, age 5 weeks (Charles River), were injected (s.c.) into the interscapular region with a MDA-MB435S (passage #249)/Matrigel suspension ($2.4 \times 10^6$ cells/mouse) [Leuschner 2006]. Phor18-LHRH (338613) (ID: 338613 lot# P080401) (0.00002, 0.0002, 0.002, 0.02, 0.2 and 1 mg/kg) and unconjugated Phor18=CLIP71 (APC 338983, Lot # WO8033C1) plus LHRH (0.2/0.122 mg/kg, ([D-Trp6]-LHRH; Sigma L9761, lot #037K1103) were reconstituted in USP saline prior to dosing. The doses were given as a single bolus intravenous injection via lateral tail vein once per week for 3 weeks.

Each group consisted of 16 mice, which were injected once a week for 3 weeks. A group of 16 mice was sacrificed at the time of treatment start to serve as baseline. Saline injections served as control groups. During the entire study tumor volumes were recorded twice weekly.

Treatment started on day 16 after tumor cell injection when the tumors were established and continued on days 23 and 30. All remaining mice were necropsied 37 days after tumor cell injection.

Treatment response was determined by tumor weights and tumor weight change at necropsy compared to saline controls and untargeted CLIP71 treatment. Primary tumors were collected, weighed and prepared for histological evaluation in formalin fixation with 10% PBS buffered formalin. Statistical evaluation of data sets were conducted in GraphPad Prizm 4 and significance calculated by Wilcoxon signed-rank test.

Tumor volumes and tumor weights increased in saline controls and mice treated with clip71 plus LHRH. Tumor volumes and tumor weights were reduced significantly compared to saline controls in mice treated with 0.0002 mg/kg Phor18-LHRH (338613). Treatment with doses of Phor18-LHRH (338613) as low as 0.002 mg/kg significantly reduced tumor volume and tumor weight compared to baseline ($p < 0.0002$).

Histological evaluation of tumor sections from MDA-MB435S xenografted mice stained with hematoxylin/eosin from treated mice show viable tumor cells in saline control and mice treated with CLIP71/LHRH. In contrast, significant necrosis was evident in tumors from mice treated with Phor18-LHRH (338613) at doses as low as 0.0002 mg/kg. Untargeted cationic lytic peptide CLIP71 did not decrease tumor weights or destroy tumor tissue.

Phor18-LHRH (338613) was highly effective in reducing tumor weights of MDA-MB435S xenografts as low as 0.002 mg/kg leading to necrosis in treated tumor tissues. Untargeted treatment with cytolytic peptides is ineffective.

In order to determine the minimal effective dose necessary to reduce MDA-MB435S xenograft weights in a multiple dose regimen, Nu/Nu female mice, outbred strain, age 8 weeks (Charles River), were injected (s.c.) into the interscapular region with a MDA-MB435S (passage #253)/Matrigel suspension ($2 \times 10^6$ cells/mouse) as previously described above. Phor18-LHRH (338613) (ID: 338613 lot# P080401) (0.002, and 0.2 mg/kg) were reconstituted in USP saline prior to dosing. The doses were given as a single bolus intravenous injection via lateral tail vein on days 15, 16, 17, 20, 21, 22, 23, 27, 28, 29, 30, 33, 34, 35, 36, 37, 38, 40, 41, 42 after tumor cell inoculation. Saline injections served as control groups.

Each treatment group consisted of 16 mice. During the entire study tumor volumes were recorded twice weekly. Final necropsy was conducted on day 45 after tumor cell injection. Injections were resumed due to occlusion of the tail vein in most mice. At study endpoint body weight, tumor weights were determined and fixed in phosphate buffered 10% formalin.

Treatment with hor18-LHRH (338613) using multiple intravenous injections resulted in tumor regression at both dose levels. Tumor free mice were observed in both treatment groups as 6/23 in group receiving 0.002 mg/kg and 1/20 at 0.2 mg/kg. Residual masses typically consisted of Matrigel. One mouse did not respond to treatment in group 0.2 mg/kg.

No necrosis in the tails was observed, no reddening of the tails was present. Bodyweights were not affected by treatment over the entire study period.

Survival was 100% in treated mice. In contrast, 8 mice in the saline control group were sacrificed on day 30 post tumor cell injection (prior to study endpoint) because the tumor volume exceeded 2,500 mm$^3$.

Histological examination of H&E stained tumors from mice treated with 0.002 and 0.2 mg/kg Phor18-LHRH (338613) in multiple injection regimen showed eradication of tumor cells in treated mice. In contrast, viable tumor cells were present in saline control mice.

Phor18-LHRH (338613) destroyed and reduced tumor weights significantly and extended the lifespan of treated mice. The treatments were without any visible effects on body weight or organ examination.

Example 9

This example includes a description of peptide KFAK-FAKKFAKFAKKFAKQHWSYGLRPG (SEQ. ID NO. 15) (Phor18-LHRH (338613)) efficacy studies in a breast, ovarian and prostate cancer xenograft models.

In vitro studies described herein demonstrated that Phor18-LHRH (338613) is a fast acting agent, killing cancer cells within minutes of contact. To determine the efficacy of Phor18-LHRH (338613) on breast cancer xenografts in the initial phase of targeted treatment, kinetics of cell destruction through Phor 18-LHRH (338613) in a breast cancer xenograft model after a single injection of Phor18-LHRH (338613) was studied In brief, Nu/Nu female mice, outbred strain, age 5 weeks (Charles River), were injected (s.c.) into the interscapular region with a MDA-MB-435 S (passage #249)/Matrigel suspension ($2.4 \times 10^6$ cells/mouse) as described in Example 10. Phor18-LHRH (338613) (ID: 338613 lot#f P080401) (0.2, and 2 mg/kg) were reconstituted in USP saline prior to dosing. The doses were given as a single bolus intravenous injection via lateral tail vein.

Mice were sacrificed 1, 2 and 16 hours after treatment with Phor 18-LHRH (338613) or saline. At study endpoint body weight, tumor weights were determined and tumors were fixed in phosphate buffered 10% formalin.

Histological evaluation from H&E stained sections from tumors showed viable tumor cells with multiple mitotic figures in saline treated mice. Treatment with Phor18-LHRH (338613) at both 0.2 and 2 mg/kg doses showed destruction of tumors from MDA-MB435S xenografts as rapidly as 1 hour after injection.

Phor18-LHRH (338613) destroyed tumors as early as 1 h after dosing, suggesting a fast acting mechanism that causes cell death through necrosis. These data confirm that Phor18-LHRH (338613) acts through its membrane contact to LHRH receptor presenting tumor cells.

To determine the efficacy of Phor18-LHRH (338613) on ovarian cancer xenografts that resemble the human disease, single and multiple dose studies were conducted. The xenograft model of the OVCAR-3 human ovarian cancer cell line that present functional LHRH receptors was used in this study. OVCAR-3 represents a slow growing xenograft model and secretes the tumor marker (cancer antigen 125, or CA1125). It's secretion can be used as treatment response and is a measure of drug activity.

The purpose of this xenograft study was to test Phor 18-LHRH (338613) in a ovarian cancer model, to determine if Phor18-LHRH (338613) is effective in vivo in multi-drug resistant, slow growing tumor models as single weekly injections. In brief, Nu/Nu female mice, inbred strain, age 5 weeks (Harlan-Sprague Dawley) were injected subcutaneously with a NIH:OVCAR-3 cells/Matrigel suspension ($4.6 \times 10^6$ cells/mouse). Treatment was started on day 33 after tumor cell injection when the tumors were established and continued on days 41 and 47. The doses for the 3 weekly injections were 0.02, 0.2 and 2 mg/kg body weight, given as a single bolus intravenous injection via lateral tail vein administered once a week for three weeks on days 33, 41 and 47. Necropsies were conducted on day 52. Data are presented as mean SEM. Arrows show dosing.

Treatment groups included saline control (N=10), Phor18-LHRH (338613) (338613, V09108X1) (0.02 (N=10), 0.2 (N=10), and 2 mg/kg (N=9), and unconjugated Phor18=CLIP71 (APC 338983, Lot #V04004Z1) (2 mg/kg (N=10)), Cisplatinum/CP in saline (Calbiochem, Cat 232120, D0005495,) (10 mg/kg, 3 qd (N=10), baseline (N=9).

A group of 9 tumor bearing mice was sacrificed on day 33 and served as baseline group. All mice were necropsied 51-52 days after tumor cell injection. Tumor volumes and bodyweights were recorded twice weekly during the study, as well as overall veterinarian examination of mice was conducted.

Primary tumors, liver, kidney, pancreas, heart, lung, and spleen were collected, fixed in formalin and prepared for histological evaluation. Tumor weights were measured at necropsy, part of the tumors were frozen at −80° C. for LH/CG and LHRH receptor assay determination.

As a biomarker for drug activity, CA125 was determined in serum, collected from each individual mouse at necropsy using a Enzyme Linked Immunoassay for quantitative determination of ovarian cancer antigen CA125 (Assay kit Genway, Biotech, Inc. San Diego, Calif., Catalog #40-052-115009, # BC-1013 according to the manufacturer).

LHRH receptor levels were assessed from formalin fixed tumors. Quantitative immunoperoxidase image analysis was conducted with the Ventana Image Analysis System (VIAS) adjunctive computer assisted image analysis system functionally connected to an interactive microscope (Axio Imager). The quantitative analysis was conducted with the program for quantification of Her2/neu receptor that included morphometric and colorimetric analysis. Receptor status results were reported as percentage of cells showing positive staining of the LHRH receptors under the following criteria: 0 non-immunoreactive, 1+: 1-25% positive, 2+: 26-50% positive, 3+: 51-75% positive cells.

All mice groups tolerated the injections well. One mouse died during the first injection with Phor 18-LHRH (338613) at the 2 mg/kg dose. Death was an acute event and was procedural and not related to treatment. All mice in other treatment groups survived. No mice died as a consequence of injection later than 10 minutes after injection.

Tumor volumes decreased during treatment with Phor 18-LHRH (338613). In contrast, for mice treated with the CLIP71, cisplatinum or in saline controls, tumor growth was observed. The tumor volumes recorded alter 42 days after tumor cell injection showed reductions ($p<0.001$) compared to baseline at concentrations of Phor18-LHRH (338613) as low as 0.2 mg/kg bodyweight.

Characteristics of tumors at necropsy (median tumor weights and changes of median tumor weights compared to baseline) were determined. Reduced tumor weights compared to saline controls and unconjugated Phor 18=CLIP71 ($p<0.05$) were obtained in the groups for 2 and 0.2 mg/kg dosages of Phor18-LHRH (338613). Tumor free mice were found in groups 0.2 and 2 mg/kg of Phor 18-LHRH (338613). Treatment response measured as tumor regression compared to treatment start was greatest in mice treated with Phor18-LHRH (338613) at 0.2 mg/kg ($p<0.03$ vs baseline). Cisplatinum and unconjugated Phor18=CLIP 71 were not effective in reducing tumor weights.

Saline controls, CLIP71 and cisplatinum treated mice showed steady tumor growth. Serum levels for CA125 corresponded to tumor weights ($r^2=0.66$). CA125 secretion was reduced in Phor18-LHRH (338613) treated mice and compared to saline controls was greatest in mice treated with Phor18-LHRH (338613) at 0.2 and 2 mg/kg ($p<0.0002$).

Sizes of tumor excised from OVCAR-3 xenograft bearing mice after treatment with 0.02 mg/kg Phor18-LHRH (338613) were reduced and necrotic compared to saline controls. Treated tumors showed a reduction of LHRH receptor levels by 1-2 score points. Tumor sections stained with hematoxylin/eosin showed significant necrosis in groups treated with 0.02 mg/kg Phor18-LHRH (338613). Xenograft bearing mice treated with Cisplatinum or CLIP71 has no reduction in tumor volume, LHRH receptor levels and showed viable tumor cells after histological evaluation.

Treatment with Phor18-LHRH (338613) caused tumor regression, reduction of CA125 tumor marker in plasma, reduction of LHRH receptor levels and necrosis in ovarian xenograft model. Phor18-LHRH (338613) is therefore effective in destroying multi-drug resistant ovarian cancer xenografts.

To determine the efficacy of Phor 18-LHRH (338613) on prostate cancer xenografts, the effect of Phor18-LHRH (338613) in vivo in a fast aggressive growing xenograft model was studied. PC-3 xenografts untreated cause significant weight loss in mice.

In brief, Nu/Nu male mice, outbred strain, age 6 weeks (Charles River) were injected subcutaneously with a PC-3 cells/Matrigel suspension ($1\times10^6$ cells/mouse). Treatment was started on day 15 after tumor cell injection when the tumors were established and continued on days 22 and 29. The doses for the 3 weekly injections were 2, 0.2 and 0.02 mg/kg body weight given as a bolus single intravenous injection via lateral tail vein. Treatment groups included saline control (N=12), Phor18-LHRH (338613) (APC 338613 Lot # V09108X1) (0.002 (N=12), 0.02 (N=12), 0.2 (N=12) and 2 mg/kg (N=12), and unconjugated Phor18 CLIP71 (338983, Lot # V04004X1) (5 mg/kg (N=12), baseline (N=12).

A group of 12 tumor bearing mice was sacrificed on day 15 and served as baseline group. All mice were necropsied 35 and 36 days after tumor cell injection. Tumor volumes and bodyweights were recorded twice weekly during the study, as well as overall veterinarian examination of mice was conducted.

Primary tumors, liver, kidney, pancreas, heart, lung, and spleen were collected, fixed in formalin and prepared for histological evaluation. Tumor weights were measured at necropsy, part of the tumors were frozen at −80° C. for LH/CG and LHRH receptor assay determination.

All groups tolerated the injections well and all mice in treatment groups survived. No mice died as a consequence of injection.

Tumor volumes decreased during treatment with PHor18-LHRH (338613) at doses of 0.002, 0.02, 0.2 and 2 mg/kg. For mice treated with the CLIP71 or in saline controls, tumor growth was observed. The tumor volumes recorded after 22 days after tumor cell injection showed reductions ($p<0.001$) compared to saline controls and CLIP71 at concentrations of Phor18-LHRH (338613) as low as 0.002 mg/kg bodyweight. Tumor weights were significantly reduced compared to saline controls and CLIP-71 treatment groups (0.001 in all Phor18-LHRH (338613) treated groups).

PC-3 xenografts are known to cause weight loss in nude mice. In Phor18-LHRH (338613) treated mice, tumor volumes decreased in groups treated with 0.002, 0.02, 0.2 and 2 mg/kg Phor18-LHRH (338613) compared to saline controls and CLIP71 injections. Median tumor weights at necropsy were significantly reduced compared to saline controls and CLIP71 ($p<0.001$). Mice in control groups were cachectic and suffered a weight loss of more than 10 g compared to treated mice.

Phor18-LHRH (338613) is effective in arresting tumor growth in PC-3 xenografts and preventing severe weight loss due to tumor burden. Unconjugated Phor18-LHRH (338613) is ineffective.

In sum, the foregoing studies indicate that peptide KFAK-FAKKFAKFAKKFAKQHWSYGLRPG (SEQ. ID NO.15) (Phor18-LHRH (338613)) is effective in vivo in destroying breast cancer, ovarian cancer and prostate cancer xenografts. Phor 18-LHRH (338613) causes tumor necrosis in treated mice, with necrosis being evident as early as 1 hour post injection. Phor 18-LHRH (338613) is effective as a single weekly treatment regimen inducing necrosis and causing tumor weight reduction. As a multiple weekly regimen eradication of tumors is more evident including destruction of residual tumor cells. Phor 18-LHRH (338613) causes reduction in LHRH receptor levels after treatment, consistent with target cell destruction.

What is claimed:

1. A fusion construct comprising a first lytic domain and a second domain, wherein said first lytic domain consists of peptide KFAKFAKKFAKFAKKFA (SEQ ID NO:3), or KFAKFAKKFAKFAKKFAKF (SEQ ID NO.5) or KFAKFAKKFAKFAKKFAKFA (SEQ ID NO.6); and said second domain comprises a binding moiety, wherein the binding moiety comprises a luteinizing hormone releasing hormone (LHRH), a LHRH analogue, a fragment of a LHRH, or a fragment of a LHRH analogue that binds to a LHRH receptor, or wherein the binding moiety comprises a chorionic gonadotropin beta subunit (β-CG), a β-CG analogue, a fragment of a β-CG or a β-CG analogue that binds to a luteinizing hormone (LH)/chorionic gonadotropin (CG) receptor.

2. The fusion construct of claim 1, wherein said binding moiety binds a cell.

3. The fusion construct of claim 2, wherein said cell is a hyperproliferative cell.

4. The fusion construct of claim 2, wherein said cell is a cancer cell.

5. The fusion construct of claim 1, wherein said binding moiety comprises a luteinizing hormone releasing hormone (LHRH) or a LHRH analogue that binds to a LHRH receptor.

6. The fusion construct of claim 1, wherein said binding moiety comprises a luteinizing hormone releasing hormone (LHRH), a LHRH analogue, a fragment of a LHRH, or a fragment of a LHRH analogue that binds to a LHRH receptor.

7. The fusion construct of claim 1, wherein said LHRH is the amino acid sequence set forth as: QHWSYGLRPG (SEQ. ID NO. 9).

8. The fusion construct of claim 1, wherein said LHRH analogue is zoladex, supprelin, triptorelin, buserelin, centrorelix, ganirelix, abarelix, antide, teverelix or degarelix (Fe200486).

9. The fusion construct of claim 1, wherein said binding moiety comprises a chorionic gonadotropin beta subunit (β-CG) or a β-CG analogue that binds to a LH/CG receptor.

10. The fusion construct of claim 1, wherein said binding moiety is a chorionic gonadotropin beta subunit (β-CG), a β-CG analogue, a fragment of a β-CG or a β-CG analogue that binds to a luteinizing hormone (LH)/chorionic gonadotropin (CG) receptor.

11. The fusion construct of claim 1, wherein said fragment of β-CG is the amino acid sequence set forth as: SYAVALSAQAALARR (SEQ. ID NO. 8).

12. The fusion construct of claim 1, wherein said binding moiety has a linear or cyclic structure.

13. The fusion construct of claim 1, wherein said first lytic domain is positioned at the $NH_2$-terminus relative to said second domain.

14. The fusion construct of claim 1, wherein said second domain is positioned at the $NH_2$-terminus relative to said first domain.

15. The fusion construct of claim 1, wherein said first lytic domain or said second domain has one or more D-amino acids.

16. The fusion construct of claim 1, wherein said first lytic domain has a D-amino acid at any K, F or A residue.

17. The fusion construct of claim 1, wherein said first lytic domain forms an amphipathic alpha-helix.

18. The fusion construct of claim 1, wherein said first lytic and second domains are joined by a covalent bond.

19. The fusion construct of claim 1, wherein said first lytic and second domains are joined by a peptide or a non-peptide linker.

20. The fusion construct of claim 19, wherein said non-peptide linker comprises a linear carbon chain linker.

21. The fusion construct of claim 19, wherein said non-peptide linker comprises a linear 6 carbon chain linker.

22. The fusion construct of claim 1, wherein said first lytic and second domains are joined by peptide linker sequence having from 1 to 25 amino acid residues.

23. The fusion construct of claim 1, wherein said first lytic and second domains are joined by peptide linker sequence comprising one or more A, S or G amino acid residues.

24. The fusion construct of claim 1, wherein said first lytic and second domains are joined by peptide sequence comprising or consisting of: GSGGS (SEQ ID NO:10), or ASAAS (SEQ ID NO.11).

25. The fusion construct of claim 1, further comprising a third, fourth, fifth, sixth or seventh domain.

26. The fusion construct of claim 1, wherein said fusion construct is isolated or purified.

27. The fusion construct of claim 1, wherein said fusion construct comprises a mixture.

28. The fusion construct of claim 1, wherein said fusion construct has greater anti-cell proliferative activity than Phor21-βCG-ala, Phor21-(SEQ ID NO.10)-βCG-ala, Phor21-(SEQ ID NO.11)-βCG-ala, or Phor 14-βCG-ala, as ascertained by a lower $IC_{50}$ value.

29. The fusion construct of claim 1, wherein said fusion construct has a smaller $IC_{50}/(HA_{50}$, hemolytic activity) ratio, than Phor21-βCG-ala, Phor21-(SEQ ID NO.10)-βCG-ala, Phor21-(SEQ ID NO.11)-βCG-ala, or Phor 14-βCG-ala.

30. The fusion construct of claim 1, wherein said fusion construct has an $IC_{50}/(HA_{50}$, hemolytic activity) ratio of less than about 0.02.

31. A composition comprising the fusion construct of claim 1.

32. The composition of claim 31, further comprising an alkylating agent, anti-metabolite, plant extract, plant alkaloid, nitrosourea, hormone, nucleoside or a nucleotide analog.

33. The composition of claim 31, further comprising cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), vinblastine, vincristine, doxorubicin, dibromomannitol, irinotecan, topotecan, etoposide, teniposide, gemcitabine, or pemetrexed.

34. A composition comprising the fusion construct of claim 1, and an anti-cell proliferative or immune stimulating agent.

35. A pharmaceutical composition comprising the fusion construct of claim 1.

36. The pharmaceutical composition of claim 35, further comprising an alkylating agent, anti-metabolite, plant extract, plant alkaloid, nitrosourea, hormone, nucleoside or a nucleotide analog.

37. The pharmaceutical composition of claim 35, further comprising further comprising cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), vinblastine, vincristine, doxorubicin, dibromomannitol, irinotecan, topotecan, etoposide, teniposide, gemcitabine, or pemetrexed.

38. A unit dosage, comprising the fusion construct of claim 1 in a pharmaceutical composition.

39. A kit comprising the fusion construct of claim 1 and instructions for reducing or inhibiting proliferation of a cell, reducing or inhibiting proliferation of a hyperproliferating cell, reducing or inhibiting proliferation of a neoplastic, tumor or cancer cell, treating a subject having a hyperproliferative disorder, treating a subject having a neoplasia, tumor or cancer, or reducing fertility of an animal.

40. The fusion construct of claim 1, wherein said first lytic domain consists of peptide KFAKFAKKFAKFAKKFAKF (SEQ ID NO.5).

41. The fusion construct of claim 1, wherein said first lytic domain consists of peptide KFAKFAKKFAKFAKKFA (SEQ ID NO.3).

42. The fusion construct of claim 1, wherein said first lytic domain consists of peptide KFAKFAKKFAKFAKKFAKFA (SEQ ID NO.6).

43. An isolated or purified peptide consisting of KFAKFAKKFAKFAKKFA (SEQ ID NO:3), KFAKFAKKFAKFAKKFAKF (SEQ ID NO:5) or KFAKFAKKFAKFAKKFAKFA (SEQ ID NO:6).

* * * * *